US005643781A

United States Patent [19]
Suzuki

[11] Patent Number: 5,643,781
[45] Date of Patent: Jul. 1, 1997

[54] DNA ENCODING PROTOCADHERIN-42

[75] Inventor: Shintaro Suzuki, Torrance, Calif.

[73] Assignee: Doheny Eye Institute, Los Angeles, Calif.

[21] Appl. No.: 998,003

[22] Filed: Dec. 29, 1992

[51] Int. Cl.$^6$ .................... C12N 1/21; C12N 5/10; C12N 15/70; C12N 15/85
[52] U.S. Cl. ................. 435/325; 435/252.33; 435/328.1; 536/23.4
[58] Field of Search .................. 435/69.1, 172.3, 435/320.1, 252.3; 536/23.4

[56] References Cited

U.S. PATENT DOCUMENTS 4,512,922   4/1985   Jones et al. .......................... 530/408

OTHER PUBLICATIONS

Brown et al. (1979) Methods in Enzymology, ed. Ray Wu vol. 68, Academic Press, NY, pp. 109–151.
Glover (1984) Gene Cloning: The Mechanics of DNA Manipulation, Chapman and Hall Ltd, London, pp. 1–20 and 178–219.
Amagai et al., "Autoantibodies against a Novel Epithelial Cadherin in Pemphigus Vulgaris, a Disease of Cell Adhesion", *Cell*, 67: 869–977 (Nov. 29, 1991).
Angerer et al., "Demonstration of Tissue–Specific Gene Expression by *in situ* Hybridization", *Methods in Enzymology*, 152: 649–660 (1987).
Ausubel et al., Eds., *Current Protocols in Molecular Biology*, Sections 6.6.1–6.1.4, 6.2.1–6.2.3 John Wiley & Sons, New York (1987).
Chen et al., "Cell–Cell Contacts Mediated by E–Cadherin (Uvomorulin) Restrict Invasive Behavior of L–Cells", *J. Cell Biol.*, 114(2):319–327 (Jul. 1991).
Detrick et al., "The Effects of N–Cadherin Misexpression on Morphogenesis in Xenopus Embryos", *Neuron*, 4:493–506 (Apr. 1990).
Donalies et al., "Expression of M–cadherin, a Member of the Cadherin Multigene Family, Correlates with Differentiation of Skeletal Muscle Cells", *PNAS, USA*, 88:8024–8028 (Sep. 1991).
Frixen et al., "E–Cadherin–Mediated Cell–Cell Adhesion Prevents Invasiveness of Human Carcinoma Cells", *J. Cell Biol.*, 113(1):173–185 (Apr. 1991).
Fujimori et al., "Ectopic Expression of N–cadherin Perturbs Histogenesis in Xenopus Embryos", *Development*, 110:97–103 (1990).
Gallin et al., "Sequence Analysis of a cDNA Clone Encoding the Liver Cell Adhesion Molecule, L–CAM", *PNAS, USA*, 84:2808–2812 (May 1987).
Goodwin et al., "Desmoglein Shows Extensive Homology to the Cadherin Family of Cell Adhesion Molecules", *Biochem. Biophys. Res. Commun.*, 173(3):1224–1230 (Dec. 31, 1990).
Hatta et al., "Cloning and Expression of cDNA Encoding a Neural Calcium–dependent Cell Adhesion Molecule: Its Identity in the Cadherin Gene Family", *J. Cell Biol.*, 106: 873–881 (Mar. 1988).

Holton et al., "Desmosomal Glycoproteins 2 and 3 (desmocollins) Show N Terminal Similarity to Calcium–Dependent Cell–Cell Adhesion Molecules", *J. Cell Science*, 97:239–246 (1990).
Inuzuka et al., "R–Cadherin: A Novel Ca$^{2+}$–Dependent Cell–Cell Adhesion Molecule Expressed in the Retina", *Neuron*, 69–71 (1991).
Kennett, "Cell Fusion", *Methods in Enzymol*, 58: 345–359 (1978).
Kitner et al., "Regulation of Embryonic Cell Adhesion by the Cadherin Cytoplasmic Domain", *Cell*, 69: 225–236 (Apr. 17, 1992).
Koch et al., "Identification of Desmoglein, a Constitutive Desmosomal Glycoprotein, as a Member of the Cadherin Family of Cell Adhesion Molecules", *Eur. J. Cell Biol*, 53: 1–12 (1990).
Liaw et al., "Identification and Cloning of Two Species of Cadherins in Bovine Endothelial Cells", *EMBO J.*, 9(9): 2701–2708 (1990).
Mahoney et al., "The *fat* Tumor Suppressor Gene in Drosophila Encodes a Novel Member of the Cadherin Gene Superfamily", *Cell*, 67: 853–868 (Nov. 29, 1991).
Maniatis et al., p. 196 in *Molecular Cloning: A Laboratory Manual*, Cold Spring Harbor, New York: Cold Spring Harbor Laboratory (1982).
Maruyama et al., "Detection of Calcium Binding Proteins by $^{45}$Ca Autoradiography on Nitrocellulose Membrane after Sodium Dodecyl Sulfate Gel Electrophoresis[1]", *J. Biochem.*, 95: 511–519 (1984).
Matsunaga et al., "Guidance of Optic Nerve Fibers by N–cadherin Adhesion Molecules", *Nature*, 334:62–64 (Jul. 1988).
Miyatani et al., "Neural Cadherin: Role in Selective Cell–Cell Adhesion", *Science*, 245:631–635 (Aug. 1989).
Nagafuchi et al., "Transformation of Cell Adhesion Properties by Exogenously Introduced E–cadherin cDNA", *Nature*, 329: 341–343 (Sep. 1987).
Napolitano et al., "Molecular Cloning and Characterization of B–Cadherin, a Novel Chick Cadherin", *J. Cell Biol.*, 113(4): 893–905 (May 1991).
Nose et al., "Isolation of Placental Cadherin cDNA: Identification of a Novel Gene Family of Cell–Cell Adhesion Molecules", *EMBO J.* 6(12): 3655–3661 (1987).
Porter et al., "Dystrophin Colocalizes with β–Spectrin in Distinct Subsarcolemmal Domains in Mammalian Skeletal Muscle", *J. Cell Biol.*, 117(5): 997–1005 (Jun. 1992).

(List continued on next page.)

*Primary Examiner*—Mindy Fleisher
*Assistant Examiner*—James Ketter
*Attorney, Agent, or Firm*—Marshall, O'Toole, Gerstein, Murray & Borun

[57] ABSTRACT

Polynucleotide sequences encoding novel cadherin-related polypeptides, designated protocadherins, and variants thereof are provided by the invention as well as methods and materials for the recombinant production of the same. Antibody substances specific for protocadherins are also disclosed as useful for modulating the natural binding and/or regulatory activities of the protocadherins.

9 Claims, 3 Drawing Sheets

OTHER PUBLICATIONS

Ranscht et al., "T-Cadherin, a Novel Cadherin Cell Adhesion Mol. in the Nervous System Lacks the Conserved Cytoplasmic Region", *Neuron*, 7:391–402 (Sep. 1991).

Ringwald et al., "The Structure of Cell Adhesion Molecule Uvomorulin. Insights into the Molecular Mechanism of $Ca^{2+}$-Dependent Cell Adhesion", *EMBO J.*, 6(12): 3647–3653 (1987).

Shimoyama et al., "Molecular Cloning of a Human $Ca^{2+}$-Dependent Cell–Cell Adhesion Molecule Homologous to Mouse Placental Cadherin: Its Low Expression in Human Placental Tissues", *J. Cell Biol.*, 109: 1787–1794 (Oct. 1989).

Suzuki et al., "Diversity of the Cadherin Family: Evidence for Eight New Cadherins in Nervous Tissue", *Cell Regulation*, 2: 261–270 (Apr. 1991).

Suzuki et al., "Evidence for Cadherin Superfamily," *Cell Struct. Func.*, 16:605 (Nov. 23, 1991).

Suzuki et al., "Evidence for Cadherin Superfamily", *J. Cell Biol.*, 115:72a (Abstract 416) (Dec. 9, 1991).

Takeichi, "Cadherin Cell Adhesion Receptors as a Morphogenetic Regulator", *Science*, 251: 1451–1455 (Mar. 1991).

Takeichi, "Cadherins: A Molecular Family Important in Selective Cell–Cell Adhesion", *Annu. Rev. Biochem.*, 59: 237–252 (1990).

Thomas, "Hybridization of Denatured RNA and Small DNA Fragments Transferred to Nitrocellulose", *PNAS, USA*, 77(9): 5201–5205 (Sep. 1980).

Towbin et al., "Electrophoretic Transfer of Proteins from Polyacrylamide Gels to Nitrocellulose Sheets: Procedure and Some Applications", *PNAS*, 76: 4350–4354 (Sep. 1979).

Urushihara et al., "Immunological Detection of Cell Surface Components Related with Aggregation of Chinese Hamster and Chick Embryonic Cells", *Dev. Biol.*, 70: 206–216 (1979).

Vanderbark et al., "Experimental Allergic Encephalomyelitis and Cellular Immunity in the Lewis Rat", *Cell. Immunol.*, 12: 85–93 (1974).

Vleminckx et al., "Genetic Manipulation of E–Cadherin Expression by Epithelial Tumor Cells Reveals an Invasion Suppressor Role", *Cell*, 66: 107–119 (Jul. 12, 1991).

FIGURE 1A

```
PC43   EC 1  (29)   ASTVIHYEIPEEREK------GFAVGNVVANL--GLDLGSLSA--  (63)
       EC 2  (136)  PTQEMKLEISEAVAP------GTRFPLESAH---DPDLGSNSL--  (169)
       EC 3  (245)  NQSLYRARVPGGCTS------GTRVQVLAT----DLDEGPNGE--  (278)
       EC 4  (353)  TVTSVYSPVPEDAS-------GTVIALLSVT---DLDAGENGL--  (385)
       EC 5  (457)  SQSSYDVYIEENNLP------GAPILNLSVW---DPDAPQNAR--  (490)
       EC 6  (567)  LYPRPGGSSVEMLPRGTSA--GHLVSRVVGW---DADAGHNAW--  (604)

PC42   EC 1  (42)   VPEEQPPNTLI----------GSL----------AADYGFPDVG-  (65)
       EC 2  (147)  ASPVITLAIPENTNI------GSLFPIPLAS---DRDAGPNGV--  (180)
       EC 3  (247)  ERPSYEAELSENSPI------GHSVIQVKAN---DSDQGANAE--  (280)
       EC 4  (354)  EIRGIGLVTHQDGMANISEDVAEETAVALVQVSDRDEGENAA--  (395)
       EC 5  (473)  TQSVTEVAFPENNKP------GEVIAEITAS---DADSGSNAE--  (506)
       EC 6  (579)  MLSGYNFSVMENMPA------LSPVGMVTVI---DGDKGENAQ--  (612)
       EC 7  (682)  TAPSNTSHKLLTPQTRL----GETVSQVAAE---DFDSGVNAE--  (717)

FAT    EC18  (1)    EDTVYSFDIPENAQR------GYQVGQIVAR---DADLGQNAQ--  (34)

N-CAD  EC 1  (1)    DWVIPPINLPENSRG------PFPQELVRIRS--DRDKNLSLRYT  (37)
       EC 2  (109)  LHQVWNGSVPEGSKP------GTYVMTVTAI---DADDPNALNGM  (144)
       EC 3  (224)  TAMTFYGEVPENRVD------IIVANLTVT----DKDQPHTPAWN  (258)
       EC 4  (339)  APNPKIIRQEEGLHA------GTMLTTFTAG---DPDRYMQQN--  (372)
       EC 5  (447)  LPQEAETCETPDPNSINITTAL---------------DYDIDPNAGP-  (478)

MOTIF         *****Q****v*En***-----GT*v***v*A*----D*D*G*N**--
```

```
PC43  EC 1   (64)   RRFPVVSGASRR------FFEVNRET----GEMFVNDR---   (91)
      EC 2  (170)   QTYELSRNEY--------FALRVQTREDSTKYAELVLERA--  (201)
      EC 3  (279)   IIYSFGSHNRAGVRQL--FALDLVT----GMLTIKGR---    (309)
      EC 4  (386)   VTCEVPPGLP--------FSLTSSLKNYFTLKTSAD---     (413)
      EC 5  (491)   LSFFLLEQGAETGLVGRYFTINRDN----GIVSSLVP---    (523)
      EC 6  (605)   LSYSLFGSPNQSL-----FAIGLHT-------GQISTARPV---(633)

PC42  EC 1   (66)   HLYKLEVGAP--------YLRVDGKT----GDIFTTETS---  (92)
      EC 2  (181)   ASYELQVAED--------QEEKQPQLIVMGN-----        (203)
      EC 3  (281)   IEYTFHQAPEVVRRL---LRLDRNT----GLITVQGP---    (310)
      EC 4  (396)   VTCVVAGDVP--------FQLRQASETGSDSKKYFLQTTTP   (429)
      EC 5  (507)   LVYSLEPEPAAKGL----FTISPET----GEIQVKTS---    (535)
      EC 6  (613)   VQLSVEQDNGD-------FVIQNGT----GTILSSLS---    (638)
      EC 7  (718)   LIYSIAGGNPYGL-----FQIGSHS-------GAITLEKE--- (745)

FAT   EC18   (35)   LSYGVVSDWANDV-----FSLNPQT----GMLTLTAR---    (62)

N-CAD EC 1   (38)   VTGPGADQPPTGI-----FIINPIS----GQLSVTKP---    (65)
      EC 2  (145)   LRYRILSQAPSTPSPNM-FTINNET----GDIITVAAG---   (177)
      EC 3  (259)   AVTRISGGDPTGR-----FAIQTDPNSND-GLVTVVKP---   (290)
      EC 4  (373)   IRYTKLSDPAN-------WLKIDPVN---GQITTIAV---    (399)
      EC 5  (479)   FAYDLPLSPVTIKRN---WTITRLN-------GDFAQLNLK---(509)

MOTIF               I*O*I*********O*I***T-----G*I*T***----
```

FIGURE 1B

```
PC43  EC 1  (92)   LDREELCGTLPSCTVTLELVVENP----------------LELFSVEVVIQDINDNNPAF  (135)
      EC 2  (202)  LDREREPSLQLVLTALDGGTPAL-----------------SASLPIHIKVLDANDNAPVF  (244)
      EC 3  (310)  LDFEDTKLHEIYIQAKDKGANPE-----------------GAHCKVLVEVVDVNDNAPEI  (352)
      EC 4  (414)  LDRETVPEYNLSITARDAGTPSL-----------------SALTIVRVQVSDINDNPPQS  (456)
      EC 5  (524)  LDYEDRREFELTAHISDGGTPVL-----------------ATNISVNIFVTDRNDNAPQV  (566)
      EC 6  (634)  QDTDSPRQTLTVL-IKDNGEPSLSTTATLTVSVTEDSPEARAEFPSGSAPREQKKN     (688)

PC42  EC 1  (93)   IDREGLRECQNQLPGDPCILEFEVSITDLVQNAS--PRLLEGQIEVQDINDNTPNF     (146)
      EC 2  (204)  LDRERWDSYDLTIKVQDGGSPPR-----------------ATSALLRVTVLDTNDNAPKF  (246)
      EC 3  (311)  VDREDLSTLRFSVLAKDRGTNPK-----------------SARAQVVTVKDMNDNAPTI  (353)
      EC 4  (430)  LDYEKVKDYTIEIVAVDSGNPPL-----------------SSTNSLKVQVVDVNDNAPVF  (472)
      EC 5  (536)  LDREQRESYELKVVAADRGSPSL-----------------QGTATVLVNVLDCNDNDPKF  (578)
      EC 6  (639)  FDREQQSTYTFQLKAVDGGVPPR-----------------SAYVGVTINVLDENDNAPYI  (681)
      EC 7  (746)  IERRHHGLHRLVVKVSDRGKPPRYGTALVHLYVNETLANRTLLETLLGHSLDTPLD     (801)
                                                       (802) IDIAGDPEYERSKQRGN     (818)

FAT   EC18  (63)   LDYEEVQHYILIVQAQDNGQPSL-----------------STTITVYCNVLDLNDNAPIF  (105)

N-CAD EC 1  (66)   LDREQIARFHLRAHAVDINGNQV-----------------ENPIDIVINVIDMNDNRPEF  (108)
      EC 2  (178)  LDREKVQQYTLIIQATDMEGNPTYGL---------------SNTATAVITVTDVNDNPPEF  (223)
      EC 3  (291)  IDFETNRMFVLTVAAENQVPLAKGIQHPP-----------QSTATVSVTVIDVNE-NPYF  (338)
      EC 4  (400)  LDRESPNVKNNIYNATFLASDNGIPPM--------------SGTGTLQIYLLDINDNAPQV  (446)
      EC 5  (510)  IKFLEAGIYEVPIIITDSGNPPKSNKS-------------ILRVRVCQCDFNGDCTDVDR  (557)

MOTIF             LDRE*****o*L*v*A*D*G*P**---------------**T*TV*v*V*D*NDNAP*F
```

FIGURE 1C 5,643,781

DNA ENCODING PROTOCADHERIN-42

FIELD OF THE INVENTION

The present invention relates, in general, to materials and methods relevant to cell-cell adhesion. More particularly, the invention relates to novel adhesion proteins, designated protocadherins, and to polynucleotide sequences encoding the protocadherins. The invention also relates to methods for inhibiting binding of the protocadherins to their natural ligands/antiligands.

BACKGROUND

In vivo, intercellular adhesion plays an important role in a wide range of events including morphogenesis and organ formation, leukocyte extravasion, tumor metastasis and invasion, and the formation of cell junctions. Additionally, cell-cell adhesion is crucial for the maintenance of tissue integrity.

Intercellular adhesion is mediated by specific cell surface adhesion molecules. Cell adhesion molecules have been classified into at least four families including the immunoglobulin superfamily, the integrin superfamily, the selectin family and the cadherin superfamily. All cell types that form solid tissues express some members of the cadherin superfamily suggesting that cadherins are involved in selective adhesion of most cell types.

Cadherins have been generally described as glycosylated integral membrane proteins that have an N-terminal extracellular domain (the N-terminal 113 amino acids of the domain appear to be directly involved in binding) consisting of five subdomains characterized by sequences unique to cadherins, a hydrophobic membrane-spanning domain and a C-terminal cytoplasmic domain that interacts with the cytoskeleton through catenins and other cytoskeleton-associated proteins. Some cadherins lack a cytoplasmic domain, however, and appear to function in cell-cell adhesion by a different mechanism than cadherins having a cytoplasmic domain. The cytoplasmic domain is required for the adhesive function of the extracellular domain in cadherins that do have an cytoplasmic domain. Binding between members of the cadherin family expressed on different cells is bomophilic (i.e., a member of the cadherin family binds to cadherins of its own or a closely related subclass) and $Ca^{2+}$-dependent. For recent reviews on cadherins, see Takeichi, *Annu. Rev. Biochem.*, 59: 237–252 (1990) and Takeichi, *Science*, 251: 1451–1455 (1991).

The first cadherins to be described (E-cadherin in mouse epithelial cells, L-CAM in avian liver, uvomorulin in the mouse blastocyst, and CAM 120/80 in human epithelial cells) were identified by their involvement in $Ca^{2+}$-dependent cell adhesion and their unique immunological characteristics and tissue localization. With the later immunological identification of N-cadherin, which was found to have a different tissue distribution than E-cadherin, it became apparent that a new family of $Ca^{2+}$-dependent cell-cell adhesion molecules had been discovered.

The molecular cloning of the genes encoding E-cadherin [see Nagafuchi et at., *Nature*, 329: 341–343 (1987)], N-cadherin [Hatta et at., *J. Cell. Biol.*, 106: 873–881 (1988)], and P-cadherin [Nose et al., *EMBO J.*, 6: 3655–3661 (1987)] provided structural evidence that the cadherins comprised a family of cell adhesion molecules. Cloning of L-CAM [Gallin et al., *Proc. Natl. Acad. Sci. USA*, 84: 2808–2812 (1987)] and uvomorulin [Ringwald et al., *EMBO J.*, 6: 3647–3653 (1986)] revealed that they were identical to E-cadherin. Comparisons of the amino acid sequences of E-, N-, and P-cadherins showed a level of amino acid similarity of about 45%–58% among the three subclasses. Liaw et al., *EMBO J.*, 9: 2701–2708 (1990) describes the use of PCR with degenerate oligonucleotides based on conserved regions of the E-, N- and P-cadherins to amplify N- and P-cadherin from a bovine microvascular endothelial cell cDNA.

The isolation by PCR of eight additional cadherins was reported in Suzuki et al., *Cell Regulation*, 2: 261–270 (1991). Subsequently, several other cadherins were described including R-cadherin [Inuzuka et al., *Neuron*, 7: 69–79 (1991)], M-cadherin [Donalies, *Proc. Natl. Acad. Sci. USA*, 88: 8024–8028 (1991)], B-cadherin [Napolitano, *J. Cell. Biol.*, 113: 893–905 (1991)] and T-cadherin [Ranscht, *Neuron*, 7: 391–402 (1991)].

Additionally, proteins distantly related to cadherins such as desmoglein [Goodwin et al., *Biochem. Biophys. Res. Commun.*, 173: 1224–1230 (1990) and Koch et al., *Eur. J. Cell Biol.*, 53: 1–12 (1990)] and the desmocollins [Holton et al., *J. Cell Science*, 97: 239–246 (1990)] have been described. The extracellular domains of these molecules are structurally related to the extracellular domains of typical cadherins, but each has a unique cytoplasmic domain. Mahoney et al., *Cell*, 67: 853–868 (1991) describes a tumor suppressor gene of Drosophila, called fat, that also encodes a cadherin-related protein. The fat tumor suppressor comprises 34 cadheiln-like subdomains followed by four EGF-like repeats, a transmembrane domain, and a novel cytoplasmic domain. The identification of these cadherin-related proteins is evidence that a large superfamily characterized by a cadherin extracellular domain motif exists.

Studies of the tissue expression of the various cadherin-related proteins reveal that each subclass of molecule has a unique tissue distribution pattern. For example, E-cadherin is found in epithelial cells while N-cadherin is found in neural and muscle cells. Expression of cadherin-related proteins also appears to be spatially and temporally regulated during development because individual proteins appear to be expressed by specific cells and tissues at specific developmental stages [for review see Takeichi (1991), supra]. Both the ectopic expression of cadherin-related proteins and the inhibition of native expression of cadherin-related proteins hinders the formation of normal tissue structure [Detrick et al., *Neuron*, 4: 493–506 (1990); Fujimoil et al., *Development*, 110: 97–104 (1990); Kintner, *Cell*, 69: 225–236 (1992)].

The unique temporal and tissue expression pattern of the different cadherins and cadherin-related proteins is particularly significant when the role each subclass of proteins may play in vivo in normal events (e.g., the maintenance of the intestinal epithelial barrier) and in abnormal events (e.g., tumor metastasis or inflammation) is considered. Different subclasses or combinations of subclasses of cadherin-related proteins are likely to be responsible for different cell-cell adhesion events in which therapeutic detection and/or intervention may be desirable. For example, auto-antibodies from patients with pemphigus vulgaris, an autoimmune skin disease characterized by blister formation caused by loss of cell adhesion, react with a cadherin-related protein offering direct support for adhesion function of cadherins in vivo [Amagai et al., *Cell*, 67: 869–877 (1991)]. Studies have also suggested that cadherins and cadherin-related proteins may have regulatory functions in addition to adhesive activity. Matsunaga et al., *Nature*, 334: 62–64 (1988) reports that N-cadherin has neurite outgrowth promoting activity. The Drosophila fat tumor supressor gene appears to regulate cell growth and supress tumor invasion as does mammalian E-cadherin [see Mahoney et al., supra; Frixen et al., *J. Cell. Biol.*, 113: 173–185 (1991); Chen et al., *J. Cell. Biol.*, 114: 319–327 (1991); and Vleminckx et al., *Cell*, 66: 107–119 (1991)]. Thus, therapeutic intervention in the regulatory activities of cadherin-related proteins expressed in specific tissues may be desirable.

There thus continues to exist a need in the art for the identification and characterization of additional cadherin-related proteins which participate in cell-cell adhesion and/or regulatory events. Moreover, to the extent that cadherin-related proteins might form the basis for the development of therapeutic and diagnostic agents, it is essential that the genes encoding the proteins be cloned. Information about the DNA sequences and amino acid sequences encoding the cadherin-related proteins would provide for the large scale production of the proteins by recombinant techniques and for the identification of the tissues/cells naturally producing the proteins. Such sequence information would also permit the preparation of antibody substances or other novel binding molecules specifically reactive with the cadherin-related proteins that may be useful in modulating the natural ligand/antiligand binding reactions in which the proteins are involved.

SUMMARY OF THE INVENTION

The present invention provides cadherin-related materials and methods that are relevant to cell-cell adhesion. In one of its aspects, the present invention provides purified and isolated polynucleotide sequences (e.g., DNA and RNA, both sense and antisense strands) encoding the novel cell adhesion molecules designated herein as protocadherins, including protocadherin-42 and protocadherin-43. Preferred polynucleotide sequences of the invention include genomic and cDNA sequences as well as wholly or partially synthesized DNA sequences, and biological replicas thereof. Biologically active vectors comprising the polynucleotide sequences are also contemplated.

Specifically illustrating protocadherin polynucleotide sequences of the present invention are the inserts in the plasmids pRC/RSV-pc42 and pRC/RSV-pc43 which were deposited with the American Type Culture Collection (ATCC), 12301 Parklawn Drive, Rockville, Md. 20852 on Dec. 16, 1992 and were assigned ATCC Accession Nos. 69162 and 69163, respectively.

The scientific value of the information contributed through the disclosures of the DNA and amino acid sequences of the present invention is manifest. For example, knowledge of the sequence of a partial or complete DNA encoding a protocadherin makes possible the isolation by DNA/DNA hybridization of full length cDNA or genomic DNA sequences that encode the protein and, in the case of genomic DNA sequences, that specify protocadherin-specific regulatory sequences such as promoters, enhancers and the like. DNA/DNA hybridization procedures utilizing the DNA sequences of the present invention also allow the isolation of DNAs encoding heterologous species proteins homologous to the protocadherins specifically illustrated herein.

According to another aspect of the invention, host cells, especially eucaryotic and procaryotic cells, are stably transformed or transfected with the polynucleotide sequences of the invention in a manner allowing the expression of protocadherin polypeptides in the cells. Host cells expressing protocadherin polypeptide products, when grown in a suitable culture medium, are particularly useful for the large scale production of protocadherin polypeptides, fragments and variants thereby enabling the isolation of the desired polypeptide products from the cells or from the medium in which the cells are grown.

The novel protocadherin protein products of the invention may be obtained as isolates from natural tissue sources, but are preferably produced by recombinant procedures involving the host cells of the invention. The products may be obtained in fully or partially glycosylated, partially or wholly de-glycosylated, or non-glycosylated forms depending on the host cell selected or recombinant production and/or post-isolation processing.

Protocadherin variants according to the invention may comprise polypeptide analogs wherein one or more of the specified amino acids is deleted or replaced or wherein one or more non-naturally encoded amino acids are added: (1) without loss, and preferably with enhancement, of one or more of the biological activities or immunological characteristics specific for a protocadherin; or (2) with specific disablement of a particular ligand/antiligand binding function.

Also contemplated by the present invention are antibody substances (e.g., monoclonal and polyclonal antibodies, chimeric and humanized antibodies, antibody domains including Fab, Fab', F(ab')$_2$, Fv or single variable domains, and single chain antibodies) which are specific for the protocadherins of the invention. Antibody substances can be developed using isolated natural, recombinant or synthetic protocadherin polypeptide products or host cells expressing such products on their surfaces. The antibody substances may be utilized for purifying protocadherin polypeptides of the invention, for determining tissue expression of polypeptides and as antagonists of the ligand/antiligand binding activities of the protocadherins. Specifically illustrating monoclonal antibodies of the present invention are the protocadherin-43 specific monoclonal antibodies produced by the hybridoma cell line designated 38I2C which was deposited with the ATCC on Dec. 2, 1992 and was assigned ATCC Accession No. HB 11207.

BRIEF DESCRIPTION OF THE DRAWING

Numerous other aspects and advantages of the present invention will be apparent upon consideration of the following detailed description, reference being made to the drawings wherein FIGS. 1A–C is an alignment of protocadherin amino acid sequences of the invention (SEQ ID NO: 97, the sequence of protocadherin-43, and SEQ ID NO: 95, the sequence of protocadherin-42) with the amino acid sequences of N-cadherin (SEQ ID NO:98) and of the Drosophila fat tumor suppressor (SEQ ID NO: 99). In FIGS. 1A–1C, the position at which an amino acid appears in a SEQ ID NO is indicated in parenthesis. For example, in FIG. 1A the first amino acid of the first extracellular domain (EC1) of protocadherin-43 is an alanine which appears at position 29 in SEQ ID NO: 97 and the last amino acid of the protocadherin-43 EC1 appearing in FIG. 1A is an alanine which appears at position 63 in SEQ ID NO: 97.

DETAILED DESCRIPTION

The present invention is illustrated by the following examples wherein Examples 1, 2 and 3 describe the isolation by PCR of protocadherin polynucleotide sequences of the invention. Example 4 presents the construction of expression plasmids including polynucleotides encoding protocadherin-42 or protocadherin-43 and the transfection of L cells with the plasmids. The generation of antibodies to protocadherin-42 and protocadherin-43 is described in Example 5. Example 6 presents the results of immunoassays of transfected L cells for the expression of protocadherin-42 or protocadherin-43. Example 7 describes the cell aggregation properties of transfected L cells. The calcium-binding properties of pc43 are described in Example 8. The results of assays of various tissues and cell lines for the expression of protocadherin-42 and protocadherin-43 by Northern blot, Western blot and in situ hybridization are respectively presented in Examples 9, 10 and 11.

EXAMPLE 1

The polymerase chain reaction (PCR) was used to isolate novel rat cDNA fragments encoding cadherin-related polypeptides.

Design of PCR primers

Two regions of conserved amino acid sequence, one from the middle of the third cadherin extracellular subdomain (EC-3) and the other from the C-terminus of the fourth extracellular subdomain (EC-4), were identified by comparison of the published amino acid sequences for L-CAM (Gallin et al., supra), E-cadherin (Nagafuchi et al., supra), mouse P-cadherin (Nose et al., supra), uvomorulin (Ringwald et al., supra), chicken N-cadherin (Hatta et al., supra), mouse N-cadherin [Miyatani et al., Science, 245: 631–635 (1989)] and human P-cadherin [Shimoyama et al., J. Cell. Biol., 109: 1787–1794 (1989)], and the corresponding degenerate oligonucleotides respectively set out below in IUPAC nomenclature were designed for use as PCR primers.

Primer 1 (SEQ ID NO: 1)

5' AARSSNNTNGAYTRYGA 3'

Primer 2 (SEQ ID NO: 2)

3' TTRCTRTTRCGNGGNNN 5'

The degenerate oligonucleotides were synthesized using an Applied Biosystems model 380B DNA synthesizer (Foster City, Calif.).

Cloning of cDNA sequences by PCR

PCR was carried out in a manner similar to that described in Suzuki et al., Cell Regulation, 2: 261–270 (1991) on a rat brain cDNA preparation. Total RNA was prepared from rat brain by the guanidium isothiocyanate/cesium chloride method described in Maniatis et al., pp. 196 in Molecular Cloning: A Laboratory Manual, Cold Spring Harbor, N.Y.: Cold Spring Harbor Laboratory (1982). Brain poly(A)$^+$ RNAs were then isolated using a FastTrack® kit (Invitrogen, San Diego, Calif.) and cDNA was prepared using a cDNA synthesis kit (Boehringer Mannheim Biochemicals, Indianapolis, Ind.). The PCR reaction was initiated by adding 2.5 units of Taq DNA polymerase (Boehringer Mannheim Biochemicals) to 100 ng template cDNA and 10 µg of each primer, after which 35 reaction cycles of denaturation at 94° C. for 1.5 minutes, annealing at 45° C. for 2 minutes, and polymerization at 72° C. for 3 minutes were carried out. Two major bands of about 450 base pairs (bp) and 130 bp in size were found when the products of the PCR reaction were subjected to agarose gel electrophoresis. The 450 bp band corresponded to the expected length between the two primer sites corresponding to the middle of the third cadherin extracellular subdomain (EC-3) and the carboxyl terminus of the fourth cadherin extracellular subdomain (EC-4), but the 130 bp band could not be predicted from any of the previously identified cadherin sequences. The 450 bp and 130 bp bands were extracted by a freezing and thawing method. The resulting fragments were phosphorylated at the 5' end with T4 poly- nucleotide kinase and subcloned by a blunt-end ligation into the Sma I site of M13mp18 (Boehringer Mannheim Biochemicals) in a blunt end ligation for sequence analysis. Sequencing of the fragments was carried out by the dideoxy-nucleotide chain termination method using a Sequenase kit (United States Biochemicals, Cleveland, Ohio). DNA and amino acid sequence were analyzed using the Beckman Microgenie program (Fullerton, Calif.).

Analysis of cDNA sequences

Nineteen novel partial cDNA clones were isolated. The DNA and deduced amino acid sequences of the clones (including sequences corresponding to the PCR primers) are set out as follows: RAT-123 (SEQ ID NOs: 3 and 4, respectively), RAT-212 (SEQ ID NOs: 5 and 6), RAT-214 (SEQ ID NOs: 7 and 8), RAT-216 (SEQ ID NOs: 9 and 10), RAT-218 (SEQ ID NOs: 11 and 12), RAT-224 (SEQ ID NOs: 13 and 14), RAT-312 (SEQ ID NOs: 15 and 16), RAT-313 (SEQ ID NOs: 17 and 18), RAT-314 (SEQ ID NOs: 19 and 20), RAT-315 (SEQ ID NOs: 21 and 22), RAT-316 (SEQ ID NOs: 23 and 24), RAT-317 (SEQ ID NOs: 25 and 26), RAT-321 (SEQ ID NOs: 27 and 28), RAT-323 (SEQ ID NOs: 29 and 30), RAT-336 (SEQ ID NOs: 31 and 32), RAT-352 (SEQ ID NOs: 33 and 34), RAT-411 (SEQ ID NOs: 35 and 36), RAT-413 (SEQ ID NOs: 37 and 38), and RAT-551 (SEQ ID NOs: 39 and 40).

The deduced amino acid sequences of the cDNA clones are homologous to, but distinct from the known cadherins. The cadherins described thus far have highly conserved, short amino acid sequences in the third extracellular subdomain (EC-3) including the consensus sequence D-Y-E or D-F-E located at the middle region of the subdomain and the consensus sequence D-X-N-E-X-P-X-F (SEQ ID NO: 41) or D-X-D-E-X-P-X-F (SEQ ID NO: 42) at its end (Hatta et al., supra), while the corresponding sequences of other subdomains, except for the fifth extracellular subdomain (EC-5), are D-R-E and D-X-N-D-N-X-P-X-F (SEQ ID NO: 43), respectively. In contrast, the deduced amino acid sequences of the new clones that correspond to cadherin extracellular subdomains include the sequence D-Y-E or D-F-E at one end, but have the sequence D-X-N-D-N-X-P-X-F (SEQ ID NO: 43) instead of D-X-N-E-X-P-X-F (SEQ ID NO: 41) or D-X-D-E-X-P-X-F (SEQ ID NO: 42), at the other end. The polypeptides encoded by the partial clones are homologous to previously identified cadherins but did not show significant homology to any other sequences in Genbank. Therefore, the partial cDNAs appear to comprise a new subclass of cadherin-related molecules.

EXAMPLE 2

Various cDNA fragments structurally similar to the rat cDNAs described in Example 1 were isolated from human, mouse, and Xenopus brain cDNA preparations and from Drosophila and C. elegans whole body cDNA preparations by PCR using Primers 1 and 2 as described in Example 1. The DNA and deduced amino acid sequences of the resulting PCR fragments (including sequences corresponding to the PCR primers) are set out as follows: MOUSE-321 (SEQ ID NOs: 44 and 45), MOUSE-322 (SEQ ID NOs: 46 and 47), MOUSE-324 (SEQ ID NOs: 48 and 49), MOUSE-326 (SEQ ID NOs: 50 and 51), HUMAN-11 (SEQ ID NOs: 52 and 53), HUMAN-13 (SEQ ID NOs: 54 and 55), HUMAN-21 (SEQ ID NOs: 56 and 57), HUMAN-24 (SEQ ID NOs: 58 and 59), HUMAN-32 (SEQ ID NOs: 60 and 61), HUMAN-42 (SEQ ID NOs: 62 and 63), HUMAN-43 (SEQ ID NOs: 64 and 65), HUMAN-212 (SEQ ID NOs: 66 and 67), HUMAN-213 (SEQ ID NOs: 68 and 69), HUMAN-215 (SEQ ID NOs: 70 and 71), HUMAN-223 (SEQ ID NOs: 72 and 73), HUMAN-410 (SEQ ID NOs: 74 and 75), HUMAN-443 (SEQ ID NOs: 76 and 77), XENOPUS-21 (SEQ ID NOs: 78 and 79), XENOPUS-23 (SEQ ID NOs: 80 and 81), XENOPUS-25 (SEQ ID NOs: 82 and 83), XENOPUS-31 (SEQ ID NOs: 84 and 85), DROSOPHILA-12 (SEQ ID NOs: 86 and 87), DROSOPHILA-13 (SEQ ID NOs: 88 and 89), DROSOPHILA-14 (SEQ ID NOs: 90 and 91) and C.ELEGANS-41 (SEQ ID NOs: 92 and 93). Comparison of the deduced amino acid sequences indicates significant similarity between sets of these clones. In particular, there are three sets of clones that appear to be cross-species homologues: RAT-218, MOUSE-322 and HUMAN-43; RAT-314, MOUSE-321 and HUMAN-11; and MOUSE-326 and HUMAN-42.

EXAMPLE 3

To ascertain the complete structure of the new proteins defined by the PCR products, two full length human cDNAs corresponding to the partial cDNAs HUMAN-42 and HUMAN-43 were isolated.

Isolation of full-length human cDNAs

A human fetal brain cDNA library (Stratagene, La Jolla, Calif.) in the λZapII vector was screened by the plaque hybridization method [described in Ausubel et al., Eds., *Current Protocols in Molecular Biology*, Sections 6.1.1 to 6.1.4 and 6.2.1 to 6.2.3, John Wiley & Sons, New York (1987)] with $^{32}$P-labelled HUMAN-42 and HUMAN-43 DNA fragments. The positive clones were plaque-purified and, using a helper virus, the inserts were cut out by an in vivo excision method in the form of a Bluescript SK(+) plasmid. The insert sequences were then subcloned into the M13 vector (Boehringer Mannheim, Biochemicals) for sequencing. Several overlapping cDNA clones were isolated with each probe including two cDNAs which contained the putative entire coding sequences of two novel proteins designated protocadherin-42 (pc42) and protocadherin-43 (pc43). The DNA and deduced amino acid sequences of pc42 are set out in SEQ ID NOs: 94 and 95, respectively, while the DNA and deduced amino acid sequences of pc43 are set out in SEQ ID NOs: 96 and 97, respectively.

Analysis of full-length human clones

Comparison of the full length cDNA sequences of pc42 and pc43 to the sequences of the various DNA fragments originally obtained by PCR reveals that MOUSE-326 and HUMAN-42 correspond to a portion of the fourth extracellular subdomain (EC-4) of pc42, and RAT-314, MOUSE-321, and HUMAN-11 correspond to a portion of the third extracellular subdomain (EC-3) of pc43 and RAT-218, MOUSE-322 and HUMAN-43 correspond to a portion of the fifth extracellular domain (EC-5) of pc43.

The overall structures of pc42 and pc43 are similar to that of typical cadherins but also have distinct features. Both protocadherin cDNA sequences contain putative translation initiation sites and translated amino acid sequences start with typical signal sequences, but the clones lack the prosequences that are present in all known cadherin precursors. The cDNAs encode proteins having a large N-terminal extracellular domain and a relatively short C-terminal cytoplasmic domain connected by a transmembrane sequence. The extracellular domains of pc42 and pc43 are different in length and pc42 contains seven subdomains that closely resemble the typical cadherin extracellular subdomain while pc43 has six such subdomains. The sizes of the protocadherin cytoplasmic domains are similar to those of typical cadherins, but the sequences do not show any significant homology with those of known cadherins or cadherin-related proteins.

Amino acid identity determinations between extracellular subdomains of human pc42 and pc43, and of mouse N-cadherin (SEQ ID NO: 98) (presented as an example of a "typical" cadherin) and the eighteenth extracellular subdomain of Drosophila fat tumor suppressor (EC-18, SEQ ID NO: 99) (the eighteenth extracellular subdomain of fat is a prototypical fat subdomain) are presented in Table 1 below, wherein, for example, "N-EC-1×pc42" indicates that the first extracellular subdomain of N-cadherin was compared to the extracellular subdomain of pc42 indicated on the horizonal axis.

TABLE 1

|  | EC-1 | EC-2 | EC-3 | EC-4 | EC-5 | EC-6 | EC-7 |
|---|---|---|---|---|---|---|---|
| N-EC-1 × pc42 | 20 | 27 | 26 | 26 | 31 | 29 | 17 |
| N-EC-1 × pc43 | 31 | 23 | 23 | 26 | 31 | 24 |  |
| N-EC-2 × pc42 | 28 | 30 | 32 | 30 | 37 | 31 | 19 |
| N-EC-2 × pc43 | 30 | 28 | 30 | 36 | 29 | 30 |  |
| N-EC-3 × pc42 | 21 | 26 | 30 | 29 | 31 | 30 | 22 |
| N-EC-3 × pc43 | 25 | 18 | 26 | 28 | 28 | 25 |  |
| N-EC-4 × pc42 | 28 | 28 | 26 | 25 | 29 | 27 | 17 |
| N-EC-4 × pc43 | 21 | 25 | 28 | 28 | 29 | 24 |  |
| N-EC-5 × pc42 | 24 | 21 | 25 | 24 | 24 | 19 | 12 |
| N-EC-5 × pc43 | 15 | 21 | 20 | 20 | 25 | 16 |  |
| fat EC-18 × pc42 | 22 | 35 | 32 | 34 | 42 | 35 | 19 |
| fat EC-18 × pc43 | 32 | 30 | 36 | 36 | 33 | 29 |  |

The amino acid identity values between the extracellular subdomains of pc42 and pc43, and N-cadherin EC-1 through EC-5 and Drosophila fat EC-18 are mostly less than 40%. These identity values are comparable to the values between the subdomains of other cadherin subclasses. However, higher identity values indicate that pc42 and pc43 are more closely related to fat than to N-cadherin.

Amino acid identity determinations between extracellular subdomains of human pc42 and pc43 are presented in Table 2 below.

TABLE 2

|  | pc42 | | | | | | |
|---|---|---|---|---|---|---|---|
| pc43 | EC-1 | EC-2 | EC-3 | EC-4 | EC-5 | EC-6 | EC-7 |
| EC-1 | 33 | 27 | 29 | 26 | 25 | 26 | 25 |
| EC-2 | 26 | 38 | 29 | 33 | 34 | 28 | 21 |
| EC-3 | 26 | 32 | 41 | 30 | 32 | 31 | 22 |
| EC-4 | 25 | 34 | 30 | 41 | 39 | 31 | 18 |
| EC-5 | 23 | 32 | 29 | 27 | 36 | 34 | 16 |
| EC-6 | 25 | 25 | 26 | 25 | 28 | 23 | 26 |

The identity values between respective EC-1, EC-2, EC-3, EC-4, EC-5 subdomains and the last subdomains of pc42 and pc43 are generally higher values than values obtained for comparisons of the protocadherins to N-cadherin. These results suggest that pc42 and pc43 are more closely related to one another than they are to classic cadherins.

FIGS. 1A–C presents an alignment of the deduced amino acid sequences of the extracellular subdomains of pc42 (EC-1 through EC-7) (amino acids 42–818 of SEQ ID NO: 95), pc43 (EC-1 through EC-6) (amino acids 29–688 of SEQ ID NO: 97), mouse N-cadherin (EC-1 through EC-5) (amino acids 1–557 of SEQ ID NO: 98) and Drosophila fat EC-18 (SEQ ID NO: 99). A sequence on a line in FIG. 1A continues on the same line in FIGS. 1B and 1C. Gaps were introduced to maximize homology. In FIGS. 1A–1C, the position at which an amino acid appears in a SEQ ID NO is indicated in parenthesis. For example, in FIG. 1A the first amino acid of EC1 of protocadherin-43 is an alanine which appears at position 29 in SEQ ID NO: 97 and the last amino acid of the protocadherin-43 EC1 appearing in FIG. 1A is an alanine which appears at position 63 in SEQ ID NO: 97. The amino acid residues described by capital letters in the "motif" line are present in more than half of the subdomains of N-cadherin, pc42, pc43 and Drosophila fat. The amino acid residues described by small letters in the motif line are less well conserved in human pc42, pc43, and Drosophila fat. FIGS. 1A–C shows that many amino acids characteristic of other cadherin extracellular domain repeats are conserved in the pc42 and pc43 sequences, including the cadherin sequence motifs DXD, DRE and DXNDNXPXF (SEQ ID NO: 43), two glycine residues, and one glutamic acid residue. Additionally, pc42 and pc43 share unique features in comparison to N-cadherin. More amino acids at specific sites are conserved between pc42 and pc43, such as the DXDXGXN (SEQ ID NO: 100) protocadherin sequence motif near the amino terminus of the pc42 and pc43 subdomains and the AXDXGXP (SEQ ID NO: 101) sequence motif near the carboxyl terminus of the subdomains. Additionally, both protocadherins share regions that do not show significant homology with the typical cadherin motif (of N-cadherin) near the carboxyl terminus of EC-1, in the middle of EC-2 and EC-4, and at the carboxyl terminus of the last repeat. A cysteine residue is located at a similar position in the middle of EC-4 of pc42 and pc43. In general, the extracellular subdomains of pc42 and pc43 are more similar to EC-18 of fat than the extracellular subdomains of N-cadherin.

Possible alternative splicing

Sequence analysis of various overlapping protocadherin cDNA clones revealed that some clones contained unique sequences at the 3' end, although the 5' end sequences were identical to other clones. The sequences forming the boundaries of the 3' end regions are consistent with the consensus sequence of mRNA splicing, suggesting that these clones may correspond to alternatively spliced mRNAs. The DNA and deduced amino acid sequences of one possible product of alternative splicing of pc42 mRNA are set out in SEQ ID NOs: 102 and 103. The DNA and deduced amino acid sequences of two possible products of alternative splicing of pc43 mRNA are respectively presented in SEQ ID NO: 104 and 105, and SEQ ID NOs: 106 and 107.

EXAMPLE 4

The full length human cDNAs encoding pc42 and pc43 were expressed in L cells (ATCC CCL 1) using the pRC/RSV expression vector (Invitrogen, San Diego, Calif.). The cDNAs were isolated from the Bluescript SK(+) clones described in Example 2 by digestion with SspI followed by blunt-ending with DNA polymerase and digestion with XbaI (for pc42), or by double digestion with SpeI and EcoRV (for pc43). The pRC/RSV expression vector was digested with HindIII, followed by blunt-ending and re-digestion with XbaI for insertion of pc42 sequences, or by digested with XbaI followed by blunt-ending and re-digestion with SpeI for insertion of pc43 sequences. The isolated protocadherin DNAs were ligated into the linearized pRC/RSV vector. The resulting pc42 expression plasmid designated pRC/RSV-pc42 (ATCC 69162) and pc43 expression plasmid designated pRC/RSV-pc43 (ATCC 69163) were purified by CsCl gradient centrifugation and transfected into L cells by a Ca-phosphate method.

The pc42 and pc43 transfectants were morphologically similar to the parental cells. Northern blot analysis of L cells transfected with pc42 or pc43 DNA sequences showed that the transfected cells expressed mRNAs of a size expected to encode the particular protocadherin.

EXAMPLE 5

Rabbit polyclonal antibodies specific for pc42 and pc43 were generated as well as a mouse monoclonal antibody specific for pc43.

Preparation of polyclonal antibodies specific for pc42 and pc43

DNA sequences encoding portions of the extracellular domain of pc42 and pc43 were each fused to a maltose binding protein-encoding sequence and expressed in bacteria. Specifically, DNAs corresponding to EC-4 through EC-7 of pc42 and EC-3 through EC-5 of pc43 were prepared by PCR and subcloned in the correct reading frame into the multicloning site of the pMAL expression vector (New England Biolabs, Beverly, Mass.) which contains sequences encoding maltose binding protein immediately upstream of the multicloning site. The resulting plasmids were then introduced into $E.$ $coli$ NM522 cells (Invitrogen, San Diego, Calif.) by a single step transformation method. Expression of the fusion proteins was induced by the addition of IPTG and the fusion proteins were purified from cell extracts by amylose resin affinity chromatography (New England Biolabs) as described by the manufacturer. The fusion proteins were used for the immunization of rabbits without further purification.

Polyclonal antibodies were prepared in rabbits by immunization at four subcutaneous sites with 500 µg of purified fusion protein in Freund's complete adjuvant. Subsequent immunizations with 100 µg of the fusion protein were in Freund's incomplete adjuvant. Immune sera was passed through sepharose coupled to maltose binding protein (New England Biolabs) and polyclonal antibodies were purified from immune sera using Sepharose affinity columns prepared by reaction of the purified fusion protein with CNBr Sepharose (Pharmacia). Reactivity of the polyclonal sera with purified pc42 fusion protein and pc42 transfected cell extracts (described in Example 4) was confirmed.

Preparation of monoclonal antibodies to pc43

The pc43 fusion protein (containing the EC-3 through EC-5 subdomains of pc43) was used to generate monoclonal antibodies in mice according to the method of Kennett, Methods in Enzymol., 58: 345–359 (1978). Briefly, mice were immunized with the pc43 fusion protein (100 µg) at two subcutaneous sites. The spleen from the highest titer mouse was fused to the NS1 myeloma cell line. The resulting hybridoma supernatants were screened in a ELISA assay for reactivity with the pc43 fusion protein and with maltose binding protein. The fusion wells with the highest reactivity to the pc43 extracellular domains were subcloned. The hybridoma cell line designated 3812C (ATCC HB 11207) produced a $IgG_1$ subtype monoclonal antibody specific for pc43. Reactivity of the monoclonal antibody produced by hybridoma cell line 3812C to pc43 was confirmed by immunoblotting the pc43 L cell transfectants described in Example 4. The 3812C monoclonal antibody is specific for human pc43.

EXAMPLE 6

L cells transfected with DNA sequences encoding pc42 and pc43 as prepared in Example 4 were assayed for expression of the protocadherins by immunoblot and by immunofluorescence microscopy.

Immunoblot analysis of protocadherin transfectants

Cell extracts of pc42 and pc43 transfectants were subjected to SDS-PAGE and then blotted electrophoretically onto a PVDF membrane (Millipore, Bedford, Mass.). The membranes were incubated with 5% skim milk in Tris-buffered saline (TBS) for two hours and then respectively with either pc42 polyclonal sera or pc43 monoclonal antibody for one hour. The membranes were washed three times (for 5 minutes each wash) with TBS containing 0.05% Tween 20 and respectively incubated with alkaline phosphatase-conjugated anti-rabbit IgG antibody or anti-mouse IgG antibody (Promega, Madison, Wis.) in the same buffer for one hour. After washing the membranes with TBS containing 0.05% Tween 20, reactive bands were visualized by using Western Blue solution (Promega).

Anti-pc42 polyclonal antibodies stained a band of about 170 kDa molecular weight in pc42 transfected cells, but not parental L cells. The pc43-specific monoclonal antibody (3812C) and polyclonal antibodies stained two adjacent bands of about 150 kDa molecular weight in pc43 transfected cells. The pc43 antibodies did not stain bands in parental L-cells. The molecular weights indicated by the staining of bands by the pc42 and pc43 antibodies are significantly larger than the molecular weights predicted from the deduced amino acid sequences. This discrepancy in molecular weight is common among various cadherin-related proteins and may be attributable to the glycosylation and/or cadherin specific structural properties. The pc42 antibody also stained smaller bands, which may be proteolytic degradation products.

When transfected cells were trypsinized and cell extracts were prepared, run on SDS/PAGE and immunoblotted with the appropriate antibody, the pc42 and pc43 polypeptides expressed by the transfected cells were found to be highly sensitive to proteolysis and were easily digested by 0.01% trypsin treatment. In contrast to the classic cadherins, however, these proteins were not protected from the digestion in the presence of 1–5 mM $Ca^{2+}$.

Immunofluorescence microscopy

Transfected cells were grown on a cover slip precoated with fibronectin and were fixed with 4% paraformaldehyde for 5 minutes at room temperature or with cold methanol on ice for 10 minutes followed by 4% paraformaldehyde fixation. After washing with TBS, the cells were incubated with TBS containing 1% BSA for 30 minutes and then with anti-pc42 polyclonal antibody or anti-pc43 monoclonal antibody in TBS containing 1% BSA for 1 hour at room temperature. Cover slips were then washed with TBS containing 0.01% BSA and respectively incubated with FITC-conjugated anti-rabbit antibody or anti-mouse antibody (Cappel, Durham, N.C.) for 60 minutes at room temperature. The cells were washed again with TBS containing 0.01% BSA and subjected to fluorescence microscopy. Both pc42-specific and pc43-specific polyclonal antibodies stained the cell periphery of transfected cells expressing the protocadherin proteins, mainly at the cell-cell contact sites. The antibodies did not stain the parent L cells, nor did rabbit preimmune sera stain the pc42 and pc43 transfectants.

EXAMPLE 7

The cell aggregation properties of the transfected L cells expressing protocadherin proteins were examined. Transfected L cells were cultured in Dulbecco's Modified Eagles Medium (DMEM) (Gibco, Grand Island, N.Y.) supplemented with 10% fetal bovine serum at 37° C. in 5% $CO_2$. Cells grown near confluence were treated with 0.01% trypsin in the presence of 1 mM EGTA for 25 minutes on a rotary shaker at 37° C. and collected by centrifugation. The cells were washed three times with $Ca^{2+}$ free HEPES-buffered saline (HBS) after adding soybean trypsin inhibitor, and were resuspended in HBS containing 1% BSA. The cell aggregation assay [Urushihara et al., *Dev. Biol.*, 70: 206–216 (1979)] was performed by incubating the resuspended cells in a 1:1 mixture of DMEM and HBS containing 1% BSA, 2 mM $CaCl_2$ and 20 µg/ml of deoxyribonucelease on a rotary shaker at 37° C. for 30 minutes to 6 hours.

The pc42 and pc43 transfectants did not show any significant cell aggregation activity during periods of incubation less than 1 hour. This is in contrast to the cell aggregation that occurs with classic cadherins in similar experiments (Nagafuchi et al., supra, and Hatta et al., supra). However, prolonged incubation of transfected cells (more than 1–2 hours) resulted in gradual re-aggregation of the cells into small aggregates. Similar results were obtained when single cell suspensions of transfected cells were prepared by trypsin treatment in the presence of $Ca^{2+}$. No re-aggregation was observed under the same conditions when untransfected L cells or L cells transfected with pRC/RSV vector alone were tested.

EXAMPLE 8

The procedures of Maruyama et al., *J. Biochem.*, 95: 511–519 (1984) were used to determine the calcium binding properties of pc43 by Western blot analysis in the presence or absence of calcium-45. The pc43 fusion protein described in Example 5 containing pc43 subdomains EC-3 through EC-5 was compared to the calcium binding protein calmodulin. Samples of purified pc43 fusion protein were run on SDS/PAGE and electrophoretically transferred to PVDF membrane. Binding of the $^{45}Ca^{2+}$ to the pc43 fusion protein was detected by autoradiography and was determined to be nearly as efficient as binding of $^{45}Ca^{2+}$ to calmodulin. In contrast, there was no binding of calcium to purified maltose binding protein lacking the pc43 extracellular domain. The pc43 subdomains EC-3 through EC-5 contain sequences highly homologous to the putative $Ca^{2+}$ binding motifs found in E-cadherin. [See, Ringwald et al., *EMBO J.*, 6: 3647–3653.]

EXAMPLE 9

The expression of mRNA encoding pc42 and pc43 was assayed in various tissues and cell lines by Northern blot.

Total RNAs were prepared by the guanidium isothiocyanate method and poly(A)+ RNAs were isolated using a FastTrack kit (Invitrogen). RNA preparations were electrophoresed in a 0.8% agarose gel under denaturing conditions and transferred onto a nitrocellulose filter using a capillary method. Northern blot analyses were performed according to the method of Thomas, *Proc. Natl. Acad. Sci. USA*, 77: 5201–5205 (1980). The final wash was in 0.2× standard saline titrate containing 0.1% sodium dodecyl sulfate at 65° C. for 10 minutes.

Protocadherin mRNA expression in adult rat tissues

Total mRNA preparations of rat tissues including brain, heart, liver, lung, skin, kidney and muscle were separated electrophoretically under denaturing conditions (10 µg mRNA/lane) and transferred onto nitrocellulose filters. The filters were hybridized with $^{32}P$-labelled cDNA fragments MOUSE-326 (which corresponds to EC-4 of human pc42) and RAT-218 (which corresponds to EC-5 of human pc43). The mRNAs of both protocadherins were highly expressed in brain. The pc42 probe detected a major band of 7 kb and a minor band of 4 kb in size, possibly representing the products of alternative splicing. The pc43 probe hybridized to a major band of 5 kb in size and with minor bands of smaller sizes.

Developmental expression of protocadherin mRNA in rat brain

To examine the developmental regulation of mRNA expression of the protocadherins, brain mRNA from rats at embryonic days 17 and 20, neonatal days 5 and 11 and from adult rats was prepared and subjected to Northern blot analysis as described above for other rat tissues. β-actin was used as an internal standard. mRNA levels for pc42 and pc43 proteins increased during embryonic development of the brain as compared with β-actin expression.

Protocadherin mRNA expression in human cell lines

Several neuronal and glial cell lines (including human SK-N-SH neuroblastoma, human U251 glioma, and mouse Neuro-2a neuroblastoma cell lines) were assayed by Northern blot using $^{32}$P-labelled for expression of pc42 and pc43 mRNA. Human cell lines were probed with HUMAN-42 (which corresponds to EC-4 of human pc42) and HUMAN-43 (which corresponds to EC-5 of human pc43) cDNA fragments while the mouse cell line was probed with MOUSE-326 (which corresponds to EC-4 of human pc42) and RAT-322 (which corresponds to EC-5 of human pc43) cDNA fragments. SK-N-SH human neuroblastoma cells and U251 human glioma cells were found to express pc43 mRNA and Neuro-2a mouse neuroblastoma cells were found to express pc42 mRNA.

EXAMPLE 10

Expression of pc43 protein in various human and rat tissues was assayed by Western blot.

Analysis of rat cardiac muscle extracts for pc43 protein expression

A rat heart non-ionic detergent extract was prepared by freezing a heart in liquid nitrogen after removal, powdering in a mortar and pestle, grinding briefly in a polytron in 0.5% Nonidet P40 in [10 mM PIPES (pH 6.8), 50 mM NaCl, 250 mM $NH_4SO_4$, 300 mM sucrose, 3 mM $MgCl_2$] and microfuging for 15 minutes. Samples were separated by SDS/PAGE and electrophoretically transferred to nitrocellulose (Towbin et al., PNAS 76: 4350–4354, 1979). Two pc43 protein bands with molecular weights of 150 KDa and 140 KDa were detected with rabbit polyclonal antibodies to pc43 by the immunoblot method described in Example 6.

Analysis of tissue sections for pc43 protein expression

To determine the localization of the protocadherins in various tissues, human and rat adult tissues were removed, incubated in 30% sucrose in PBS for 30 minutes at 4° C., embedded in OCT compound (Tissue-Tek, Elkhart, Ind.) in cryomolds and quickly frozen. Six micron sections were cut and placed on glass slides. The slides were washed with PBS and fixed in 3% p-formaldehyde for 5 minutes. To permeablize the tissue sections, the slides were immersed in –20° C. acetone for 10 minutes and air dried. The sections were blocked with 2% goat serum and 1% BSA in PBS for 30 minutes and then incubated with the rabbit anti-pc43 polyclonal antisera for 1 hour at room temperature. The sections were rinsed 3 times in PBS containing 0.1% BSA and incubated with a biotinylated anti-rabbit (Vector Laboratories, Burlingame, Calif.) in 1% BSA in PBS for 30 minutes. After rinsing 3 times, strepavidin-conjugated with FITC (Vector Laboratories) was added for 30 minutes and again washed 3 times. For co-localization studies, an appropriate primary antibody was used with a TRITC-conjugated secondary antibody.

Immunolocalization of pc43 in cardiac muscle shows that pc43 is localized in a repeating pattern which is consistent with pc43 being associated with the sarcomeres. Sarcomeres are repetitive contractile units between the fascia adherens in skeletal and cardiac muscle. Co-localization with cytoskeletal proteins shows that pc43 is present at the ends of the sarcomeres in the Z lines which are associated with desmin and the actin-binding protein vinculin, and alpha-actinin. The thin microfilaments of F-actin are associated with the thick myosin filaments between the Z lines. In contrast, N-cadherin is localized at the ends of cardiac myocytes at the fascia adherens junctions at sites of mycocyte:myocyte contact. The localization of pc43 in cardiac muscle suggests that pc43 may play a role in muscle contraction in the anchoring of the contractile apparatus to the plasma membrane.

Similar localization for pc43 was observed in rat skeletal muscle. Ultrastructural studies have shown that dystrophin, the gene product lacking in Duchenne muscular dystrophy, is a component of the sarcolemma [Porter et al., J. Cell. Biol., 117: 997–1005 (1992)]. The sarcolemma is connected to the contractile apparatus at the M and Z lines where pc43 is localized.

Reactivity of anti-pc43 polyclonal antibody and monoclonal antibody 38I2C on frozen sections of rat and human cerebellum, respectively, shows that the major sites of pc43 expression are located in Purkinje cells and the granule cell layer which contains numerous small neurons.

Analysis of pc43 protein expression in human cell lines

Immunocytochemical localization of pc43 in Sk-N-SH neuroblastoma cells and UW28 astrocytoma cells using anti-pc43 antibodies reveals a punctate cell surface distribution of pc43 and in some cells there is a localization at the tips of extensions of neuronal foot processes. At sites of cell-cell contact of UW28 astrocytoma cells, pc43 is organized in a series of parallel lines. The lines start at the contact site and extend approximately 5 micron. F-actin microfilaments were identified with rhodamine-phalloidin (Molecular Probes, Eugene, Oreg., as described by the manufacturer) showing that the microfilaments in the cell appear to end in the pc43 linear structures which extend from the edge of the cell at sites of cell contact.

Immunoblotting studies with pc43 specific antibodies show that a protein with a molecular weight of 140 kDa is recognized in human Sk-N-SH neuroblastoma cells and in UW28 astrocytoma cells.

EXAMPLE 11

In situ hybridization experiments using protocadherin specific RNA probes were preformed on cryosections of rat tissue.

Sense and antisense $^{35}$S-riboprobes were made using the standard procedure described by Promega (Madison, Wis.). An approximately 400 bp EcoRI-XbaI fragment of the MOUSE-326 cDNA clone was used as a pc42 specific probe. This fragment encodes the middle of EC-3 to the end of EC-4 of pc42. An approximately 700 bp SmaI fragment of the RAT-218 cDNA clone was used as a pc43 specific probe. The fragment encodes the end of EC-3 to the end of EC-5 of pc43.

Rat adult tissues were harvested and immediately embedded with OCT Compound (Tissue-Tek) in cryomolds and quickly frozen in a bath of 95% ethanol/dry ice. The frozen blocks were stored at –80° C. until cut. Six micron tissue sections were cut using a cryostat (Reichert-Jung, Model #2800 Frigocut N, Leica, Inc., Gilroy, Calif.). Cut tissue sections were stored at –80° C.

The in situ protocol used was a variation of that described by Angerer et al., Methods in Enzymology, 152: 649–660, 1987. All solutions were treated with diethylpyrocarbonate (DEPC, Sigma, St. Louis, Mo.) to remove RNase contamination. The tissue sections were first fixed in 4% paraformaldehyde at 4° C. for 20 minutes. To remove excess paraformaldehyde and stop the tissue fixation, the slides were washed in PBS (phosphate buffered saline), denatured in a graded series of alcohols (70, 95, 100%) and then dried. To prevent the tissue from detaching from the glass slide during the in situ procedure, the tissue sections were treated in a poly-L-lysine solution (Sigma) at room temperature for 10 minutes. To denature all RNA in the tissue, the sections were placed in a solution of 70% formamide/2× SSC [0.15M NaCl/0.3M Na citrate, pH 7.0] at 70° C. for 2 minutes after which they were rinsed in chilled 2× SSC, dehydrated in a graded series of alcohols and then dried. Once dried, the sections were prehybridized in hybridization buffer (50% formamide/50 mM DTT (dithiothrietol)/0.3M NaCl/20 mM Tris, pH 8.0/5 mM EDTA/1× Denhardt's (0.02% Ficoll Type 400/0.02% polyvinylpyrrolidone/0.02% BSA)/10% Dextran Sulfate) at the final hybridization temperature for approximately 4 hours. After prehybridization, approximately $1 \times 10^6$ cpm of the appropriate riboprobe was added to each section. The sections were generally hybridized at 45° C. overnight (12–16 hours). To insure that the hybridization seen was specific, in some experiments the hybridization stringency was increased by raising the hybridization temperature to 50° C. As both the 45° C. and 50° C. experiments gave comparable results, the standard hybridization temperature used was 45° C.

To remove excess, nonhybridized probe, the sections were put through a series of washes. The sections were first rinsed in 4× SSC to remove the bulk of the hybridization solution and probe. Next a 15 minute wash in 4× SSC/50 mM DTT was carried out at room temperature. Washes at increased stringencies were also utilized. A 40 minute wash in 50% formamide/2× SSC/50 mM DTT was performed at 60° C. Four final room temperature washes were carried out for 10 minutes each: two in 2× SSC and two in 0.1× SSC. The washed slides were dehydrated in a graded series of alcohols and dried.

To visualize the hybridized probe, the slides were dipped in Kodak NTB2 nuclear emulsion (International Biotechnology, New Haven, Conn.) which had been diluted 1:1 in $dH_2O$. Once dry, the slides were stored at 4° C. in light-tight boxes for the appropriate exposure time. The in situ slides were independently viewed by two persons and scored positive or negative for hybridization signal.

All in situ hybridization studies were performed on rat tissue. Because results from Northern blot experiments (see Example 9) indicated that both pc42 and pc43 are expressed in adult brain, in situ hybridization studies were carried out to localize the expression of these molecules to specific brain cell types. Hybridization seen in the normal adult rat brian was specific (no background hybridization was seen with the sense probes) and was localized to specific regions in the brain. The overall pattern of expression seen for pc42 and pc43 was very similar, with the major difference being in the level of expression. pc43 appears to be expressed at a lower level than pc42. Both molecules are expressed in the germinal and pyramidal cells of the hippocampus, Purkinje cells of the cerebellum and neurons in grey matter. In addition, pc42 is expressed in glial cells in the white matter but, in contrast to the expression of pc43 in glioma cell lines (as described in Example 9), expression of pc43 in normal glial cells was not observed. In the spinal chord, both protocadherins are expressed in the motor neurons in the gray matter and pc42 is expressed in the glial cells in the white matter.

When expression of both protocadherin molecules was determined in brains and spinal chords from rats having EAE (experimental allergic encephaiomyelitis) [Vandenbark et al., Cell. Immunol., 12: 85–93 (1974)], the same structures as described above were found to be positive. In addition, expression of pc42 was observed in the leukocytic infiltrates in the EAE tissues. Expression of pc42 in leukocytes was confirmed by in situ hybridization analysis of two leukocytic cell lines, RBL-1 and y3.

While the present invention has been described in terms of specific methods and compositions, it is understood that variations and modifications will occur to those skilled in the art. Therefore, only such limitations as appear in the claims should be placed on the invention.

---

What is claimed is:

1. A purified and isolated polynucleotide encoding the amino acid sequence of protocadherin-42 set out in SEQ ID NO: 95.

2. The polynucleotide of claim 1 which is a DNA.

3. The DNA of claim 2 which is a cDNA.

4. The cDNA of claim 3 which comprises the protein-coding portion of the protocadherin-42 sequence set out in SEQ ID NO: 94.

5. The DNA of claim 2 which is a genomic DNA.

6. The DNA of claim 2 which is a wholly or partially chemically synthesized DNA.

7. A biologically functional DNA vector comprising a DNA according to claim 2.

8. A host cell stably transformed or transfected with a DNA sequence according to claim 2 in a manner allowing the expression in said host cell of protocadherin-42 polypeptide.

9. A method for producing protocadherin-42 polypeptide comprising the steps of growing a host cell according to claim 8 in a suitable nutrient medium and isolating protocadherin-42 polypeptide from said cell or from the medium of its growth.

* * * * *

UNITED STATES PATENT AND TRADEMARK OFFICE
CERTIFICATE OF CORRECTION

PATENT NO. : 5,643,781
DATED : July 1, 1997
INVENTOR(S) : Shintaro Suzuki

It is certified that error appears in the above-identified patent and that said Letters Patent is hereby corrected as shown below:

Column 1, line 35 replace "eatinins" with --catenins--;

Column 1, line 40 replace "an" with --a--;

Column 1, line 43 replace "bomophillic" with --homophilic--;

Column 9, line 54 replace "digested" with --digestion--;

Column 10, line 46 replace "a" with --an--;

Column 10, line 50 replace "1" with --I--;

Column 10, line 53 replace "1" with --I--;

Column 10, line 55 replace "1" with --I--;

Column 11, line 14 replace "1" with --I--;

Column 12, line 50 replace "titrate" with --citrate--;

Column 14, line 24 replace "sk" with --SK--;

UNITED STATES PATENT AND TRADEMARK OFFICE
CERTIFICATE OF CORRECTION

PATENT NO. : 5,643,781
DATED : July 1, 1997
INVENTOR(S) : Shintaro Suzuki

It is certified that error appears in the above-identified patent and that said Letters Patent is hereby corrected as shown below:

Column 14, line 31 replace "micron" with --microns--;

Column 14, line 39 replace "sk" with --SK--;

Column 16, line 29 replace "encephaimyelitis" with --encephalomyelitis--.

Signed and Sealed this

Twenty-eighth Day of March, 2000

Q. TODD DICKINSON

*Attest:*

*Attesting Officer*  *Commissioner of Patents and Trademarks*

SEQUENCE LISTING ( 1 ) GENERAL INFORMATION:

( i i i ) NUMBER OF SEQUENCES: 107

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

A A R S N N T N G A Y T R Y G A         1 7

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:2:

TTRCTRTTRC GNGGNNN                                                                                                    17

( 2 ) INFORMATION FOR SEQ ID NO:3:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

AAGGGAGTGG ACTTTGAGGA GCAGCCTGAG CTTAGTCTCA TCCTCACGGC TTTGGATGGA    60
GGGACTCCAT CCAGGTCTGG GACTGCATTG GTTCAAGTGG AAGTCATAGA TGCCAATGAC   120
AACGCACCGT A                                                       131

( 2 ) INFORMATION FOR SEQ ID NO:4:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

Lys Gly Val Asp Phe Glu Glu Gln Pro Glu Leu Ser Leu Ile Leu Thr
 1               5                  10                  15

Ala Leu Asp Gly Gly Thr Pro Ser Arg Ser Gly Thr Ala Leu Val Gln
                20                  25                  30

Val Glu Val Ile Asp Ala Asn Asp Asn Ala Pro
                35                  40

( 2 ) INFORMATION FOR SEQ ID NO:5:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AAACGCATGG ATTTCGAGGA GTCTTCCTCC TACCAGATCT ATGTGCAAGC TACTGACCGG    60
GGACCAGTAC CCATGGCGGG TCATTGCAAG GTGTTGGTGG ACATTATAGA TGTGAACGAC   120
AACGCACCTA A                                                       131

( 2 ) INFORMATION FOR SEQ ID NO:6:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Lys Ala Met Asp Phe Glu Glu Ser Ser Ser Tyr Gln Ile Tyr Val Gln
1               5                   10                  15

Ala Thr Asp Arg Gly Pro Val Pro Met Ala Gly His Cys Lys Val Leu
            20              25                  30

Val Asp Ile Ile Asp Val Asn Asp Asn Ala Pro
            35              40
```

(2) INFORMATION FOR SEQ ID NO:7:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
AAGCGACTGG ACTTTGAGAC CCTGCAGACC TTCGAGTTCA GCGTGGGTGC CACAGACCAT        60
GGCTCCCCCT CGCTCCGCAG TCAGGCTCTG GTGCGCGTGG TGGTGCTGGA CCACAATGAC       120
AATGCCCCCA A                                                            131
```

(2) INFORMATION FOR SEQ ID NO:8:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Lys Arg Leu Asp Phe Glu Thr Leu Gln Thr Phe Glu Phe Ser Val Gly
1               5                   10                  15

Ala Thr Asp His Gly Ser Pro Ser Leu Arg Ser Gln Ala Leu Val Arg
            20              25                  30

Val Val Val Leu Asp His Asn Asp Asn Ala Pro
            35              40
```

(2) INFORMATION FOR SEQ ID NO:9:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
AAGGGCCTGG ATTACGAGGC ACTGCAGTCC TTCGAGTTCT ACGTGGGCGC TACAGATGGA        60
GGCTCACCCG CGCTCAGCAG CCAGACTCTG GTGCGGATGG TGGTGCTGGA TGACAACGAC       120
AACGCCCCTA A                                                            131
```

(2) INFORMATION FOR SEQ ID NO:10:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein ( x i ) SEQUENCE DESCRIPTION: SEQ ID NO:10:

```
Lys Gly Leu Asp Tyr Glu Ala Leu Gln Ser Phe Glu Phe Tyr Val Gly
1               5                   10                  15

Ala Thr Asp Gly Gly Ser Pro Ala Leu Ser Ser Gln Thr Leu Val Arg
            20                  25                  30

Met Val Val Leu Asp Asp Asn Asp Asn Ala Pro
        35                  40
```

( 2 ) INFORMATION FOR SEQ ID NO:11:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
AAGGCGTTTG ATTTGAGGA TCAGAGAGAG TTCCAGCTAA CCGCTCATAT AAACGACGGA        60
GGTACCCCGG TTTTGGCCAC CAACATCAGC GTGAACATAT TTGTTACTGA CCGCAATGAC      120
AACGCCCCGC A                                                           131
```

( 2 ) INFORMATION FOR SEQ ID NO:12:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Lys Ala Phe Asp Phe Glu Asp Gln Arg Glu Phe Gln Leu Thr Ala His
1               5                   10                  15

Ile Asn Asp Gly Gly Thr Pro Val Leu Ala Thr Asn Ile Ser Val Asn
            20                  25                  30

Ile Phe Val Thr Asp Arg Asn Asp Asn Ala Pro
        35                  40
```

( 2 ) INFORMATION FOR SEQ ID NO:13:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

```
AAGGCGGTGG ATTACGAAAT CACCAAGTCC TATGAGATAG ATGTTCAAGC CCAAGATCTG        60
GGTCCCAATT CTATTCCTGC TCATTGCAAA ATTATAATTA AGGTCGTGGA TGTCAACGAC      120
AACGCTCCCA A                                                           131
```

( 2 ) INFORMATION FOR SEQ ID NO:14:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear (i i) MOLECULE TYPE: protein (x i) SEQUENCE DESCRIPTION: SEQ ID NO:14:

```
Lys Ala Val Asp Tyr Glu Ile Thr Lys Ser Tyr Glu Ile Asp Val Gln
1               5                   10                  15

Ala Gln Asp Leu Gly Pro Asn Ser Ile Pro Ala His Cys Lys Ile Ile
            20                  25                  30

Ile Lys Val Val Asp Val Asn Asp Asn Ala Pro
            35                  40
```

(2) INFORMATION FOR SEQ ID NO:15:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:15:

```
TATGACCATG ATTACGAGAC AACCAAAGAA TATACACTGC GGATCCGGGC CCAGGATGGT      60

GGCCGGACTC CACTTTCCAA CGTCTCCGGT CTAGTAACCG TGCAGGTCCT AGACATCAAC     120

GACAATGCCC CCCCA                                                      135
```

(2) INFORMATION FOR SEQ ID NO:16:

(i) SEQUENCE CHARACTERISTICS:
        (A) LENGTH: 44 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:16:

```
Tyr Asp His Asp Tyr Glu Thr Thr Lys Glu Tyr Thr Leu Arg Ile Arg
1               5                   10                  15

Ala Gln Asp Gly Gly Arg Thr Pro Leu Ser Asn Val Ser Gly Leu Val
            20                  25                  30

Thr Val Gln Val Leu Asp Ile Asn Asp Asn Ala Pro
            35                  40
```

(2) INFORMATION FOR SEQ ID NO:17:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:17:

```
GGGGGGTCGA TTACGAGGAG AACGGCATGT TAGAGATCGA CGTGCAGGCC AGAGACCTAG      60

GACCTAACCC AATTCCAGCC CATTGCAAGG TCACAGTCAA GCTCATCGAC CGCAATGATA     120

ACGCCCCCA                                                             129
```

(2) INFORMATION FOR SEQ ID NO:18:

(i) SEQUENCE CHARACTERISTICS:
        (A) LENGTH: 43 amino acids
        (B) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:18:

```
Arg Gly Val Asp Tyr Glu Glu Asn Gly Met Leu Glu Ile Asp Val Gln
1               5                   10                  15

Ala Arg Asp Leu Gly Pro Asn Pro Ile Pro Ala His Cys Lys Val Thr
            20                  25                  30

Val Lys Leu Ile Asp Arg Asn Asp Asn Ala Pro
        35                  40
```

( 2 ) INFORMATION FOR SEQ ID NO:19:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

```
AAGGGGTTGG ACTACGAAGA CACCAAACTC CATGAGATTT ACATCCAGGC CAAAGACAAA      60
GGTGCCAATC CGGAAGGAGC GCATTGCAAA GTACTGGTAG AGGTTGTGGA CGTTAACGAC     120
AATGCCCCTC A                                                          131
```

( 2 ) INFORMATION FOR SEQ ID NO:20:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

```
Lys Gly Leu Asp Tyr Glu Asp Thr Lys Leu His Glu Ile Tyr Ile Gln
1               5                   10                  15

Ala Lys Asp Lys Gly Ala Asn Pro Glu Gly Ala His Cys Lys Val Leu
            20                  25                  30

Val Glu Val Val Asp Val Asn Asp Asn Ala Pro
        35                  40
```

( 2 ) INFORMATION FOR SEQ ID NO:21:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
AAGGGTTTGG ACTTTGAGCA AGTAGATGTC TACAAAATCC GCGTTGACGC GACGGACAAA      60
GGACACCCTC CGATGGCAGG CCATTGCACT GTTTAGTGA GGGTATTGGA TGAAAACGAC     120
AATGCGCCTC T                                                          131
```

( 2 ) INFORMATION FOR SEQ ID NO:22:

( i ) SEQUENCE CHARACTERISTICS:

(A) LENGTH: 43 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:22:

```
Lys Gly Leu Asp Phe Glu Gln Val Asp Val Tyr Lys Ile Arg Val Asp
1               5                   10                  15
Ala Thr Asp Lys Gly His Pro Pro Met Ala Gly His Cys Thr Val Leu
                20                  25                  30
Val Arg Val Leu Asp Glu Asn Asp Asn Ala Pro
                35                  40
```

(2) INFORMATION FOR SEQ ID NO:23:

(i) SEQUENCE CHARACTERISTICS:
(A) LENGTH: 134 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:23:

```
AAGGGTATAG ACTTCGAGCA GATCAAGGAC TTCAGCTTTC AAGTGGAAGC CCGGGACGCC      60
GGCAGTCCCC AGGCGCTGTC CGGCAACTGC ACTGTCAACA TCTTGATAGT GGATCAGAAC     120
GACAACGCCC CTAA                                                       134
```

(2) INFORMATION FOR SEQ ID NO:24:

(i) SEQUENCE CHARACTERISTICS:
(A) LENGTH: 44 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:24:

```
Lys Gly Ile Asp Phe Glu Gln Ile Lys Asp Phe Ser Phe Gln Val Glu
1               5                   10                  15
Ala Arg Asp Ala Gly Ser Pro Gln Ala Leu Ala Gly Asn Thr Thr Val
                20                  25                  30
Asn Ile Leu Ile Val Asp Gln Asn Asp Asn Ala Pro
                35                  40
```

(2) INFORMATION FOR SEQ ID NO:25:

(i) SEQUENCE CHARACTERISTICS:
(A) LENGTH: 134 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:25:

```
AAGCCGTTCG ACTATGAGCA AACCGCCAAC ACGCTGGCAC AGATTGACGC CGTGCTGGAA      60
AAACAGGGCA GCAATAAATC GAGCATTCTG GATGCCACCA TTTTCCTGGC CGATAAAAAC     120
GACAATGCGC CAGA                                                       134
```

(2) INFORMATION FOR SEQ ID NO:26:

( i ) SEQUENCE CHARACTERISTICS:
   ( A ) LENGTH: 44 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:26:

```
Lys Pro Phe Asp Tyr Glu Gln Thr Ala Asn Thr Leu Ala Gln Ile Asp
 1               5                  10                  15

Ala Val Leu Glu Lys Gln Gly Ser Asn Lys Ser Ser Ile Leu Asp Ala
             20                  25                  30

Thr Ile Phe Leu Ala Asp Lys Asn Asp Asn Ala Pro
             35                  40
```

( 2 ) INFORMATION FOR SEQ ID NO:27:

( i ) SEQUENCE CHARACTERISTICS:
   ( A ) LENGTH: 131 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:27:

```
AAGCGGCTGG ATTTCGAACA GTTCCAGCAG CACAAGCTGC TCGTAAGGGC TGTTGATGGA     60
GGAATGCCGC CACTGAGCAG CGATGTGGTC GTCACTGTGG ATGTCACCGA CCTCAACGAT    120
AACGCGCCCT A                                                         131
```

( 2 ) INFORMATION FOR SEQ ID NO:28:

( i ) SEQUENCE CHARACTERISTICS:
   ( A ) LENGTH: 43 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:28:

```
Lys Arg Leu Asp Phe Glu Gln Phe Gln Gln His Lys Leu Leu Val Arg
 1               5                  10                  15

Ala Val Asp Gly Gly Met Pro Pro Leu Ser Ser Asp Val Val Val Thr
             20                  25                  30

Val Asp Val Thr Asp Leu Asn Asp Asn Ala Pro
             35                  40
```

( 2 ) INFORMATION FOR SEQ ID NO:29:

( i ) SEQUENCE CHARACTERISTICS:
   ( A ) LENGTH: 131 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:29:

```
AAGGGGATAG ACTTTGAGAG TGAGAATTAC TATGAATTTG ATGTGCGGGC TCGCGATGGG     60
GGTTCTCCAG CCATGGAGCA ACATTGCAGC CTTCGAGTGG ATCTGCTGGA CGTAAATGAC    120
AACGCCCCAC T                                                         131
```

( 2 ) INFORMATION FOR SEQ ID NO:30:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:30:

```
Lys Gly Ile Asp Phe Glu Ser Glu Asn Tyr Tyr Glu Phe Asp Val Arg
 1               5                  10                 15
Ala Arg Asp Gly Gly Ser Pro Ala Met Glu Gln His Cys Ser Leu Arg
             20                  25                 30
Val Asp Leu Leu Asp Val Asn Asp Asn Ala Pro
             35              40
```

( 2 ) INFORMATION FOR SEQ ID NO:31:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

```
AAGGCATTGG ACTTTGAGGC CCGGCGACTG TATTCGCTGA CAGTTCAGGC CACGGACCGA        60
GGCGTGCCCT CGCTCACCGG GCGTGCCGAA GCGCTTATCC AGCTGCTAGA TGTCAACGAC       120
AACGCACCCA T                                                            131
```

( 2 ) INFORMATION FOR SEQ ID NO:32:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

```
Lys Ala Leu Asp Phe Glu Ala Arg Arg Leu Tyr Ser Leu Thr Val Gln
 1               5                  10                 15
Ala Thr Asp Arg Gly Val Pro Ser Leu Thr Gly Arg Ala Glu Ala Leu
             20                  25                 30
Ile Gln Leu Leu Asp Val Asn Asp Asn Ala Pro
             35              40
```

( 2 ) INFORMATION FOR SEQ ID NO:33:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

```
AAGCCAATTG ATTACGAGGC AACTCCATAC TATAACATGG AAATTGTAGC CACAGACAGC        60
GGAGGTCTTT CGGGAAAATG CACTGTGTCT ATACAGGTGG TGGATGTGAA CGACAACGCC       120
```

CCCAA                                                                                                    125

( 2 ) INFORMATION FOR SEQ ID NO:34:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

```
Lys Pro Ile Asp Tyr Glu Ala Thr Pro Tyr Tyr Asn Met Glu Ile Val
 1               5                  10                      15

Ala Thr Asp Ser Gly Gly Leu Ser Gly Lys Cys Thr Val Ser Ile Gln
            20              25                  30

Val Val Asp Val Asn Asp Asn Ala Pro
            35              40
```

( 2 ) INFORMATION FOR SEQ ID NO:35:

( i ) SEQUENCE CHARACTERISTICS:
        ( A ) LENGTH: 446 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

```
AAGCGGGTAG ACTTCGAAAT GTGCAAAAGA TTTTACCTTG TGGTGGAAGC TAAAGACGGA      60
GGCACCCCAG CCCTCAGCAC GGCAGCCACT GTCAGCATCG ACCTCACAGA TGTGAATGAT     120
AACCCTCCTC GGTTCAGCCA AGATGTCTAC AGTGCTGTCA TCAGTGAGGA TGCCTTAGAG     180
GGGGACTCTG TCATTCTGCT GATAGCAGAA GATGTGGATA GCAAGCCTAA TGGACAGATT     240
CGGTTTTCCA TCGTGGGTGG AGATAGGGAC AATGAATTTG CTGTCGATCC AATCTTGGGA     300
CTTGTGAAAG TTAAGAAGAA ACTGGACCGG GAGCGGGTGT CAGGATACTC CCTGCTCATC     360
CAGGCAGTAG ATAGTGGCAT TCCTGCAATG TCCTCAACGA CAACTGTCAA CATTGATATT     420
TCTGATGTGA ACGACAACGC CCCCCT                                         446
```

( 2 ) INFORMATION FOR SEQ ID NO:36:

( i ) SEQUENCE CHARACTERISTICS:
        ( A ) LENGTH: 148 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:36:

```
Lys Arg Val Asp Phe Glu Met Cys Lys Arg Phe Tyr Leu Val Val Glu
 1               5                  10                      15

Ala Lys Asp Gly Gly Thr Pro Ala Leu Ser Thr Ala Thr Val Ser
            20              25                  30

Ile Asp Leu Thr Asp Val Asn Asp Asn Pro Pro Arg Phe Ser Gln Asp
            35              40              45

Val Tyr Asp Ala Val Ile Ser Glu Asp Ala Leu Glu Gly Asp Ser Val
            50              55              60

Ile Leu Leu Ile Ala Glu Asp Val Asp Ser Lys Pro Asn Gly Gln Ile
65              70                  75                      80
```

|     |     |     |     |     |     |     |     |     |     |     |     |     |     |     |     |
|-----|-----|-----|-----|-----|-----|-----|-----|-----|-----|-----|-----|-----|-----|-----|-----|
| Arg | Phe | Ser | Ile | Val<br>85 | Gly | Gly | Asp | Arg | Asp<br>90 | Asn | Glu | Phe | Ala | Val<br>95 | Asp |
| Pro | Ile | Leu | Gly<br>100 | Leu | Val | Lys | Val | Lys<br>105 | Lys | Lys | Leu | Asp | Arg<br>110 | Glu | Arg |
| Val | Ser | Gly<br>115 | Tyr | Ser | Leu | Leu | Ile<br>120 | Gln | Ala | Val | Asp | Ser<br>125 | Gly | Ile | Pro |
| Ala | Met<br>130 | Ser | Ser | Thr | Thr<br>135 | Thr | Val | Asn | Ile | Asp<br>140 | Ile | Ser | Asp | Val | Asn |
| Asp<br>145 | Asn | Ala | Pro |     |     |     |     |     |     |     |     |     |     |     |     |

( 2 ) INFORMATION FOR SEQ ID NO:37:

( i ) SEQUENCE CHARACTERISTICS:
        ( A ) LENGTH: 440 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

```
AAGGGGGTTG ATTATGAGAC AAACCCACGG CTACGACTGG TGCTACAGGC AGAGAGTGGA      60
GGAGCCTTTG CTTTCTCGGT GCTGACCCTG ACCCTTCAAG ATGCCAATGA CAATGCTCCC     120
CGTTTCCTGC AGCCTCACTA CGTGGCTTTC CTGCCAGAGT CCCGACCCTT GGAAGGGCCC     180
CTGCTGCAGG TGGAAGCAGA CGACCTGGAT CAAGGCTCTG GAGGACAGAT CTCCTACAGT     240
CTGGCTGCAT CCCAGCCAGC ACGGGGCTTG TTCCATGTAG ACCCAGCCAC AGGCACTATC     300
ACTACCACAG CCATCCTGGA CCGGGAAATC TGGGCTGAAA CACGGCTGGT ACTGATGGCC     360
ACAGACAGAG GAAGCCCAGC ATTGGTGGGC TCAGCTACCC TGACAGTGAT GGTCATCGAT     420
ACCAACGACA ATGCTCCCCT                                                 440
```

( 2 ) INFORMATION FOR SEQ ID NO:38:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:38:

|     |     |     |     |     |     |     |     |     |     |     |     |     |     |     |     |
|-----|-----|-----|-----|-----|-----|-----|-----|-----|-----|-----|-----|-----|-----|-----|-----|
| Lys<br>1 | Gly | Val | Asp | Tyr<br>5 | Glu | Thr | Asn | Pro | Arg<br>10 | Leu | Arg | Leu | Val | Leu<br>15 | Gln |
| Ala | Glu | Ser | Gly<br>20 | Gly | Ala | Phe | Ala | Phe<br>25 | Ser | Val | Leu | Thr | Leu<br>30 | Thr | Leu |
| Gln | Asp | Ala<br>35 | Asn | Asp | Asn | Ala | Pro<br>40 | Arg | Phe | Leu | Gln | Pro<br>45 | His | Tyr | Val |
| Ala | Phe<br>50 | Leu | Pro | Glu | Ser | Arg<br>55 | Pro | Leu | Glu | Gly | Pro<br>60 | Leu | Leu | Gln | Val |
| Glu<br>65 | Ala | Asn | Asp | Leu | Asp<br>70 | Gln | Gly | Ser | Gly | Gln<br>75 | Ile | Ser | Tyr | Ser<br>80 |     |
| Leu | Ala | Ala | Ser | Gln<br>85 | Pro | Ala | Arg | Gly | Leu<br>90 | Phe | His | Val | Asp | Pro<br>95 | Ala |
| Thr | Gly | Thr | Ile<br>100 | Thr | Thr | Thr | Ala | Ile<br>105 | Leu | Asp | Arg | Glu | Ile<br>110 | Trp | Ala |
| Glu | Thr | Arg | Leu | Val | Leu | Met | Ala | Thr | Asp | Arg | Gly | Ser | Pro | Ala | Leu |

5,643,781

115                      120                         125
    Val Gly Ser Ala Thr Leu Thr Val Met Val Ile Asp Thr Asn Asp Asn
        130                 135                 140

Ala Pro
    145

( 2 ) INFORMATION FOR SEQ ID NO:39:

( i ) SEQUENCE CHARACTERISTICS:
        ( A ) LENGTH: 124 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

AAGGTCTCGA TTATGAGGCA ACTCCATATT ATAACGTGGA AATTGTAGCC ACAGATGGTG      60

GGGGCCTTTC AGGAAAATGC ACTGTGGCTA TAGAAGTGGT GGATGTGAAC GACGGCGCTC     120

CAAT                                                                  124

( 2 ) INFORMATION FOR SEQ ID NO:40:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:40:

Lys Gly Leu Asp Tyr Glu Ala Thr Pro Tyr Tyr Asn Val Glu Ile Val
    1               5                   10                  15

Ala Thr Asp Gly Gly Ala Phe Asp Glu Asn Cys Thr Val Ala Ile Glu
                20                  25                  30

Val Val Asp Val Asn Asp Asn Ala Pro
                35                  40

( 2 ) INFORMATION FOR SEQ ID NO:41:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

Asp Xaa Asn Glu Xaa Pro Xaa Phe
    1               5

( 2 ) INFORMATION FOR SEQ ID NO:42:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

Asp Xaa Asp Glu Xaa Pro Xaa Phe
    1               5

(2) INFORMATION FOR SEQ ID NO:43:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: DNA (xi) SEQUENCE DESCRIPTION: SEQ ID NO:43:

Asp Xaa Asn Asp Asn Xaa Pro Xaa Phe
   1               5

(2) INFORMATION FOR SEQ ID NO:44:

(i) SEQUENCE CHARACTERISTICS:
       (A) LENGTH: 131 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:44:

```
AAGCGGATGG ATTTTGAAGA CACCAAACTC CATGAGATTT ACATCCAGGC CAAAGACAAA        60
GGTGCCAATC CCGAAGGAGC GCATTGCAAA GTACTTGTAG AGGTTGTAGA CGTAAACGAC       120
AACGCCCCAG T                                                            131
```

(2) INFORMATION FOR SEQ ID NO:45:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:45:

Leu Arg Met Asp Phe Glu Asp Thr Lys Leu His Glu Ile Tyr Ile Gln
   1               5                   10                  15

Ala Lys Asp Lys Gly Ala Asn Pro Glu Gly Ala His Cys Lys Val Leu
                   20                  25                  30

Val Glu Val Val Asp Val Asn Asp Asn Ala Pro
                   35                  40

(2) INFORMATION FOR SEQ ID NO:46:

(i) SEQUENCE CHARACTERISTICS:
       (A) LENGTH: 131 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:46:

```
AAGGCTTTGG ATTACGAGGA TCAGAGAGAG TTCCAACTAA CAGCTCATAT AAACGACGGA        60
GGTACCCCAG TCTTAGCCAC CAACATCAGC GTGAACGTAT TTGTTACTGA CCGCAATGAT       120
AACGCCCCCT A                                                            131
```

(2) INFORMATION FOR SEQ ID NO:47:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:47:

| Lys | Ala | Leu | Asp | Tyr | Glu | Asp | Gln | Arg | Glu | Phe | Gln | Leu | Thr | Ala | His |
| 1 | | | | 5 | | | | | 10 | | | | | 15 | |
| Ile | Asn | Asp | Gly | Gly | Thr | Pro | Val | Leu | Ala | Thr | Asn | Ile | Ser | Val | Asn |
| | | | 20 | | | | | 25 | | | | | 30 | | |
| Val | Phe | Val | Thr | Asp | Arg | Asn | Asp | Asn | Ala | Pro | | | | | |
| | | 35 | | | | 40 | | | | | | | | | |

( 2 ) INFORMATION FOR SEQ ID NO:48:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:48:

```
AAGCGCTTGG ACTACGAGGA GAGTAACAAT TATGAAATTC ACGTGGATGC TACAGATAAA      60
GGATACCCAC CTATGGTTGC TCACTGCACC GTACTCGTGG GAATCTTGGA TGAAAATGAC     120
AACGCACCCA T                                                           131
```

( 2 ) INFORMATION FOR SEQ ID NO:49:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:49:

| Lys | Arg | Leu | Asp | Tyr | Glu | Glu | Ser | Asn | Asn | Tyr | Glu | Ile | His | Val | Asp |
| 1 | | | | 5 | | | | | 10 | | | | | 15 | |
| Ala | Thr | Asp | Lys | Gly | Tyr | Pro | Pro | Met | Val | Ala | His | Cys | Thr | Val | Leu |
| | | | 20 | | | | | 25 | | | | | 30 | | |
| Val | Gly | Ile | Leu | Asp | Glu | Asn | Asp | Asn | Ala | Pro | | | | | |
| | | 35 | | | | 40 | | | | | | | | | |

( 2 ) INFORMATION FOR SEQ ID NO:50:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:50:

```
AAACCGGTGG ACTACGAGAA AGTCAAAGAC TATACCATCG AGATCGTGGC TGTGGATTCC      60
GGCAACCCTC CACTCTCTAG CACCAACTCC CTCAAGGTGC AGGTGGTAGA CGTCAACGAT     120
AACGCCCCTC T                                                           131
```

( 2 ) INFORMATION FOR SEQ ID NO:51:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:51:

```
Lys Pro Val Asp Tyr Glu Lys Val Lys Asp Tyr Thr Ile Glu Ile Val
 1               5                  10                  15

Ala Val Asp Ser Gly Asn Pro Pro Leu Ser Ser Thr Asn Ser Leu Lys
            20                  25                  30

Val Gln Val Val Asp Val Asn Asp Asn Ala Pro
            35                  40
```

( 2 ) INFORMATION FOR SEQ ID NO:52:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

```
AAGCCTTTTG ATTTCGAGGA CACCAAACTC CATGAGATTT ACATCCAGGC CAAAGACAAG      60
GGCGCCAATC CCGAAGGAGC ACATTGCAAA GTGTTGGTGG AGGTTGTGGA TGTGAACGAC     120
AATGCCCCTC A                                                          131
```

( 2 ) INFORMATION FOR SEQ ID NO:53:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:53:

```
Lys Pro Phe Asp Phe Glu Asp Thr Lys Leu His Glu Ile Tyr Ile Gln
 1               5                  10                  15

Ala Lys Asp Lys Gly Ala Asn Pro Glu Gly Ala His Cys Lys Val Leu
            20                  25                  30

Val Glu Val Val Asp Val Asn Asp Asn Ala Pro
            35                  40
```

( 2 ) INFORMATION FOR SEQ ID NO:54:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:54:

```
AAAGGTGTCG ATTACGAGGT GAGTCCACGG CTGCGACTGG TGCTGCAGGC AGAGAGTCGA      60
GGAGCCTTTG CCTTCACTGT GCTGACCCTG ACCCTGCAAG ATGCCAACGA CAACGCCCCG     120
AG                                                                    122
```

( 2 ) INFORMATION FOR SEQ ID NO:55:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:55:

```
Lys Gly Val Asp Tyr Glu Val Ser Pro Arg Leu Arg Leu Val Leu Gln
 1               5                  10                  15

Ala Glu Ser Arg Gly Ala Phe Ala Phe Thr Val Leu Thr Leu Thr Leu
            20                  25                  30

Gln Asp Ala Asn Asp Asn Ala Pro
            35                  40
```

( 2 ) INFORMATION FOR SEQ ID NO:56:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:56:

```
AAAGGGATTG ATTACGAGCA GTTGAGAGAC CTACAGCTGT GGGTGACAGC CAGCGACAGC        60
GGGGACCCGC CTCTTAGCAG CAACGTGTCA CTGAGCCTGT TTGTGCTGGA CCAGAACGAC       120
AACGCCCCCC T                                                             131
```

( 2 ) INFORMATION FOR SEQ ID NO:57:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:57:

```
Lys Gly Ile Asp Tyr Glu Gln Leu Arg Asp Leu Gln Leu Trp Val Thr
 1               5                  10                  15

Ala Ser Asp Ser Gly Asp Pro Pro Leu Ser Ser Asn Val Ser Leu Ser
            20                  25                  30

Leu Phe Val Leu Asp Gln Asn Asp Asn Ala Pro
            35                  40
```

( 2 ) INFORMATION FOR SEQ ID NO:58:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:58:

```
AAGGCGGTCG ATTTTGAGCG CACATCCTCT TATCAACTCA TCATTCAGGC CACCAATATG        60
GCAGGAATGG CTTCCAATGC TACAGTCAAT ATTCAGATTG TTGATGAAAA CGACAACGCC       120
```

CCCCA                                                                                                    125

( 2 ) INFORMATION FOR SEQ ID NO:59:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:59:

```
Lys Ala Val Asp Phe Glu Arg Thr Ser Ser Tyr Gln Leu Ile Ile Gln
 1               5                  10                  15
Ala Thr Asn Met Ala Gly Met Ala Ser Asn Ala Thr Val Asn Ile Gln
             20                  25                  30
Ile Val Asp Glu Asn Asp Asn Ala Pro
             35                  40
```

( 2 ) INFORMATION FOR SEQ ID NO:60:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

AAACGGCTAG ACTTTGAAAA GATACAAAAA TATGTTGTAT GGATAGAGGC CAGAGATGGT      60

GGTTTCCCTC CTTTCTCCTC TTACGAGAAA CTTGATATAA CAGTATTAGA TGTCAACGAT     120

AACGCGCCTA A                                                          131

( 2 ) INFORMATION FOR SEQ ID NO:61:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:61:

```
Lys Arg Leu Asp Phe Glu Lys Ile Gln Lys Tyr Val Val Trp Ile Glu
 1               5                  10                  15
Ala Arg Asp Gly Gly Phe Pro Pro Phe Ser Ser Tyr Glu Lys Leu Asp
             20                  25                  30
Ile Thr Val Leu Asp Val Asn Asp Asn Ala Pro
             35                  40
```

( 2 ) INFORMATION FOR SEQ ID NO:62:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

AAGGGGATCG ATTATGAGAA GGTCAAAGAC TACACCATTG AGATTGTGGC TGTGGACTCT      60

GGCAACCCCC CACTCTCCAG CACTAACTCC CTCAAGGTGC AGGTGGTGGA CGTCAATGAC        120

AACGCACCGT G        131

( 2 ) INFORMATION FOR SEQ ID NO:63:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:63:

```
Lys Gly Ile Asp Tyr Glu Lys Val Lys Asp Tyr Thr Ile Glu Ile Val
 1               5                  10                     15

Ala Val Asp Ser Gly Asn Pro Pro Leu Ser Ser Thr Asn Ser Leu Lys
            20                  25                  30

Val Gln Val Val Asp Val Asn Asp Asn Ala Pro
            35                  40
```

( 2 ) INFORMATION FOR SEQ ID NO:64:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:64:

AAGGGACTCG ACTACGAGGA TCGGCGGGAA TTTGAATTAA CAGCTCATAT CAGCGATGGG        60

GGCACCCCGG TCCTAGCCAC CAACATCAGC GTGAACATAT TGTCACTGA TCGCAACGAT        120

AATGCCCCCG T        131

( 2 ) INFORMATION FOR SEQ ID NO:65:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:65:

```
Lys Gly Leu Asp Tyr Glu Asp Arg Arg Glu Phe Glu Leu Thr Ala His
 1               5                  10                     15

Ile Ser Asp Gly Gly Thr Pro Val Leu Ala Thr Asn Ile Ser Val Asn
            20                  25                  30

Ile Phe Val Thr Asp Arg Asn Asp Asn Ala Pro
            35                  40
```

( 2 ) INFORMATION FOR SEQ ID NO:66:

( i ) SEQUENCE CHARACTERISTICS:
        ( A ) LENGTH: 470 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:66:

| AAGGGTTTGG | ACTACGAGAC | CACACAGGCC | TACCAGCTCA | CGGTCAACGC | CACAGATCAA | 60 |
| GACAACACCA | GGCCTCTGTC | CACCCTGGCC | AACTTGGCCA | TCATCATCAC | AGATGTCCAG | 120 |
| GACATGGACC | CCATCTTCAT | CAACCTGCCT | TACAGCACCA | ACATCTACGA | GCATTCTCCT | 180 |
| CCGGGCACGA | CGGTGCGCAT | CATCACCGCC | ATAGACCAGG | ATCAAGGACG | TCCCCGGGGC | 240 |
| ATTGGCTACA | CCATCGTTTC | AGGGAATACC | AACAGCATCT | TTGCCCTGGA | CTACATCAGC | 300 |
| GGAGTGCTGA | CCTTGAATGG | CCTGCTGGAC | CGGGAGAACC | CCCTGTACAG | CCATGGCTTC | 360 |
| ATCCTGACTG | TGAAGGGCAC | GGAGCTGAAC | GATGACCGCA | CCCCATCTGA | CGCTACAGTC | 420 |
| ACCACGACCT | TCAATATCCT | GGTTATTGAC | ATCAACGACA | ACGCCCACT | | 470 |

(2) INFORMATION FOR SEQ ID NO:67:

(i) SEQUENCE CHARACTERISTICS:
  (A) LENGTH: 156 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:67:

```
Lys Gly Leu Asp Tyr Glu Thr Thr Gln Ala Tyr Gln Leu Thr Val Asn
 1               5                  10                  15
Ala Thr Asp Gln Asp Asn Thr Arg Pro Leu Ser Thr Leu Ala Asn Leu
            20                  25                  30
Ala Ile Ile Ile Thr Asp Val Gln Asp Met Asp Pro Ile Phe Ile Asn
        35                  40                  45
Leu Pro Tyr Ser Thr Asn Ile Tyr Glu His Ser Pro Pro Gly Thr Thr
    50                  55                  60
Val Arg Ile Ile Thr Ala Ile Asp Gln Asp Gln Gly Arg Pro Arg Gly
65                  70                  75                  80
Ile Gly Tyr Thr Ile Val Ser Gly Asn Thr Asn Ser Ile Phe Ala Leu
                85                  90                  95
Asp Tyr Ile Ser Gly Val Leu Thr Leu Asn Gly Leu Leu Asp Arg Glu
               100                 105                 110
Asn Pro Leu Tyr Ser Gly Gly Phe Ile Leu Thr Val Lys Gly Thr Glu
           115                 120                 125
Leu Asn Asp Asp Arg Thr Pro Ser Asp Ala Thr Val Thr Thr Thr Phe
       130                 135                 140
Asn Ile Leu Val Ile Asp Ile Asn Asp Asn Ala Pro
145                 150                 155
```

(2) INFORMATION FOR SEQ ID NO:68:

(i) SEQUENCE CHARACTERISTICS:
  (A) LENGTH: 131 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:68:

| AAGGGGGTCG | ATTACGAGGT | ACTACAGGCC | TTTGAGTTCC | ACGTGAGCGC | CACAGACCGA | 60 |
| GGCTCACCGG | GGCTCAGCAG | CCAGGCTCTG | GTGCGCGTGG | TGGTGCTGGA | CGACAATGAC | 120 |
| AACGCTCCCG | T | | | | | 131 |

( 2 ) INFORMATION FOR SEQ ID NO:69:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:69:

```
Lys Gly Val Asp Tyr Glu Val Leu Gln Ala Phe Glu Phe His Val Ser
 1               5                  10                  15

Ala Thr Asp Arg Gly Ser Pro Gly Leu Ser Ser Gln Ala Leu Val Arg
            20                  25                  30

Val Val Val Leu Asp Asp Asn Asp Asn Ala Pro
            35                  40
```

( 2 ) INFORMATION FOR SEQ ID NO:70:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:70:

```
AAGGGGCTGG ATTATGAGCA GTTCCAGACC CTACAACTGG GAGTGACCGC TAGTGACAGT      60

GGAAACCCAC CATTAAGAAG CAATATTTCA CTGACCCTTT TCGTGCTGGA CCAGAATGAT     120

AACGCCCCAA A                                                          131
```

( 2 ) INFORMATION FOR SEQ ID NO:71:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:71:

```
Lys Gly Leu Asp Tyr Glu Gln Phe Gln Thr Leu Gln Leu Gly Val Thr
 1               5                  10                  15

Ala Ser Asp Ser Gly Asn Pro Pro Leu Arg Ser Asn Ile Ser Leu Thr
            20                  25                  30

Leu Phe Val Leu Asp Gln Asn Asp Asn Ala Pro
            35                  40
```

( 2 ) INFORMATION FOR SEQ ID NO:72:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:72:

```
AAGCGGGTTG ATTACGAGGA TGTCCAGAAA TACTCGCTGA GCATTAAGGC CAGGATGGG       60

CGGCCCCCGC TCATCAATTC TTCAGGGGTG GTGTCTGTGC AGGTGCTGGA TGTCAACGAC     120

AATGCCCCGG A                                                          131
```

( 2 ) INFORMATION FOR SEQ ID NO:73:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:73:

```
Lys Arg Val Asp Tyr Glu Asp Val Gln Lys Tyr Ser Leu Ser Ile Lys
 1               5                  10                  15

Ala Gln Asp Gly Arg Pro Pro Leu Ile Asn Ser Ser Gly Val Val Ser
            20                  25                  30

Val Gln Val Leu Asp Val Asn Asp Asn Ala Pro
        35                  40
```

( 2 ) INFORMATION FOR SEQ ID NO:74:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:74:

```
AAACCGGTAG ACTTTGAGCT ACAGCAGTTC TATGAAGTAG CTGTGGTGGC TTGGAACTCT      60
GAGGGATTTC ATGTCAAAAG GGTCATTAAA GTGCAACTTT TAGATGACAA CGACAATGCC     120
CCGAT                                                                 125
```

( 2 ) INFORMATION FOR SEQ ID NO:75:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:75:

```
Lys Pro Val Asp Phe Glu Leu Gln Gln Phe Tyr Glu Val Ala Val Val
 1               5                  10                  15

Ala Trp Asn Ser Glu Gly Phe His Val Lys Arg Val Ile Lys Val Gln
            20                  25                  30

Leu Leu Asp Asp Asn Asp Asn Ala Pro
        35                  40
```

( 2 ) INFORMATION FOR SEQ ID NO:76:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:76:

```
AAGGGATTAG ATTTTGAAAC TTTGCCCATT TACACATTGA TAATACAAGG AACTAACATG      60
GCTGGTTTGT CCACTAATAC AACGGTTCTA GTTCACTTGC AGGATGAGAA TGATAACGCC     120
```

```
CCAAA                                                                                  125
```

( 2 ) INFORMATION FOR SEQ ID NO:77:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:77:

```
Lys Gly Leu Asp Phe Glu Thr Leu Pro Ile Tyr Thr Leu Ile Ile Gln
 1               5                  10                  15
Gly Thr Asn Met Ala Gly Leu Ser Thr Asn Thr Thr Val Leu Val His
             20                  25                  30
Leu Gln Asp Glu Asn Asp Asn Ala Pro
             35                  40
```

( 2 ) INFORMATION FOR SEQ ID NO:78:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:78:

```
AAGCGGGCGG ATTTCGAGGC GATCCGGGAG TACAGTCTGA GGATCAAAGC GCAGGACGGG      60
GGGCGGCCTC CCTCAGCAA CACCACGGGC ATGGTCACAG TGCAGGTCGT GGACGTCAAT     120
GACAACGCAC CCCT                                                      134
```

( 2 ) INFORMATION FOR SEQ ID NO:79:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:79:

```
Lys Arg Ala Asp Phe Glu Ala Ile Arg Glu Tyr Ser Leu Arg Ile Lys
 1               5                  10                  15
Ala Gln Asp Gly Gly Arg Pro Pro Leu Ser Asn Thr Thr Gly Met Val
             20                  25                  30
Thr Val Gln Val Val Asp Val Asn Asp Asn Ala Pro
             35                  40
```

( 2 ) INFORMATION FOR SEQ ID NO:80:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:80:

```
AAGCGGTTGG ATTACGAAAA GGCATCGGAA TATGAAATCT ATGTTCAAGC CGCTGACAAA      60
```

```
GGCGCTGTCC CTATGGCTGG CCATTGCAAA GTGTTGCTGG AGATCGTGGA TGTCAACGAC    120

AACGCCCCT T                                                         131
```

(2) INFORMATION FOR SEQ ID NO:81:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:81:

```
Lys Arg Leu Asp Tyr Glu Lys Ala Ser Glu Tyr Glu Ile Tyr Val Gln
 1               5                  10                  15

Ala Ala Asp Lys Gly Ala Val Pro Met Ala Gly His Cys Lys Val Leu
            20                  25                  30

Leu Glu Ile Val Asp Val Asn Asp Asn Ala Pro
            35                  40
```

(2) INFORMATION FOR SEQ ID NO:82:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:82:

```
AAGGGGATCG ATTATGAGGA TCAGGTCTCT TACACATTAG CAGTAACAGC ACATGACTAT    60

GGCATCCCTC AAAAATCAGA CACTACCTAT TTGGAAATCT TAGTAATTGA TGTTAACGAC   120

AACGCGCCCC A                                                       131
```

(2) INFORMATION FOR SEQ ID NO:83:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:83:

```
Lys Gly Ile Asp Tyr Glu Asp Gln Val Ser Tyr Thr Leu Ala Val Thr
 1               5                  10                  15

Ala His Asp Tyr Gly Ile Pro Gln Lys Ser Asp Thr Thr Tyr Leu Glu
            20                  25                  30

Ile Leu Val Ile Asp Val Asn Asp Asn Ala Pro
            35                  40
```

(2) INFORMATION FOR SEQ ID NO:84:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:84:

```
AAAGGGTTAG ATTTCGAGGG CACTAAAGAT TCAGCGTTTA AAATAGTGGC AGCTGACACA        60

GGGAAGCCCA GCCTCAACCA GACAGCCCTG GTGAGAGTAG AGCTGGAGGA TGAGAACGAC       120

AACGCCCCAA T                                                            131
```

( 2 ) INFORMATION FOR SEQ ID NO:85:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:85:

```
Lys Gly Leu Asp Phe Glu Gly Thr Lys Asp Ser Ala Phe Lys Ile Val
 1               5                  10                  15

Ala Ala Asp Thr Gly Lys Pro Ser Leu Asn Gln Thr Ala Leu Val Arg
            20                  25                  30

Val Glu Leu Glu Asp Glu Asn Asp Asn Ala Pro
                35                  40
```

( 2 ) INFORMATION FOR SEQ ID NO:86:

( i ) SEQUENCE CHARACTERISTICS:
        ( A ) LENGTH: 130 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:86:

```
AAGGGTGTGG ATTTTGAAAG TGTGCGTAGC TACAGGCTGG TTATTCGTGC TCAAGATGGA        60

GGCAGCCCCT CCAGAAGTAA CACCACCCAG CTCTTGGTCA ACGTCATCGA TCGAATGACA       120

ATGCGCCGCT                                                              130
```

( 2 ) INFORMATION FOR SEQ ID NO:87:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:87:

```
Lys Gly Val Asp Phe Glu Ser Val Arg Ser Tyr Arg Leu Val Ile Arg
 1               5                  10                  15

Ala Gln Asp Gly Gly Ser Pro Ser Arg Ser Asn Thr Thr Gln Leu Leu
            20                  25                  30

Val Asn Val Ile Asp Val Asn Asp Asn Ala Pro
                35                  40
```

( 2 ) INFORMATION FOR SEQ ID NO:88:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:88:

| | | | | | |
|---|---|---|---|---|---|
| AAGGGTGTGG | ACTTCGAGCT | GACACATCTG | TATGAGATTT | GGATTGAGGC | TGCCGATGGA | 60
| GACACGCCAA | GTCTGCGTAG | TGTAACTCTT | ATAACGCTCA | ACGTAACGGA | TGCCAATGAC | 120
| AATGCTCCCA | A | | | | | 131

( 2 ) INFORMATION FOR SEQ ID NO:89:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:89:

Lys Gly Val Asp Phe Glu Leu Thr His Leu Tyr Glu Ile Trp Ile Glu
1               5                   10                  15

Ala Ala Asp Gly Asp Thr Pro Ser Leu Arg Ser Val Thr Leu Ile Thr
                20                  25                  30

Leu Asn Val Thr Asp Ala Asn Asp Asn Ala Pro
            35                  40

( 2 ) INFORMATION FOR SEQ ID NO:90:

( i ) SEQUENCE CHARACTERISTICS:
        ( A ) LENGTH: 441 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:90:

| | | | | | |
|---|---|---|---|---|---|
| CAAGGCGTTT | GATTTGAAG | AGACAAGTAG | ATATGTGTTG | AGTGTGGAAG | CTAAGGATGG | 60
| AGGAGTACAC | ACAGCTCACT | GTAATGTTCA | AATAGAAATT | GTTGACGAGA | ATGACAATGC | 120
| CCCAGAGGTG | ACATTCATGT | CCTTCTCTAA | CCAGATTCCA | GAGGATTCAG | ACCTTGGAAC | 180
| TGTAATAGCC | CTCATAAAAG | TGCGAGACAA | GGATTCTGGG | CAAAATGGCA | TGGTGACATG | 240
| CTATACTCAG | GAAGAAGTTC | CTTTCAAATT | AGAATCCACC | TCGAAGAATT | ATTACAAGCT | 300
| GGTGATTGCT | GGAGCCCTAA | ACCGGGAGCA | GACAGCAGAC | TACAACGTCA | CAATCATAGC | 360
| CACCGACAAG | GGCAAACCAG | CCCTTTCCTC | CAGGACAAGC | ATCACCCTGC | ACATCTCCGA | 420
| CATCAACGAT | AATGCCCCCG | T | | | | 441

( 2 ) INFORMATION FOR SEQ ID NO:91:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:91:

Lys Ala Phe Asp Phe Glu Glu Thr Ser Arg Tyr Val Leu Ser Val Glu
1               5                   10                  15

Ala Lys Asp Gly Gly Val His Thr Ala His Cys Asn Val Gln Ile Glu
                20                  25                  30

Ile Val Asp Glu Asn Asp Asn Ala Pro Glu Val Thr Phe Met Ser Phe

-continued

```
                  35                          40                          45
    Ser  Asn  Gln  Ile  Pro  Glu  Asp  Ser  Asp  Leu  Gly  Thr  Val  Ile  Ala  Leu
         50                          55                     60
    Ile  Lys  Val  Arg  Asp  Lys  Asp  Ser  Gly  Gln  Asn  Gly  Met  Val  Thr  Cys
    65                          70                     75                          80
    Tyr  Thr  Gln  Glu  Glu  Val  Pro  Phe  Lys  Leu  Glu  Ser  Thr  Ser  Lys  Asn
                        85                          90                     95
    Tyr  Tyr  Lys  Leu  Val  Ile  Ala  Gly  Ala  Leu  Asn  Arg  Glu  Gln  Thr  Ala
                   100                         105                         110
    Asp  Tyr  Asn  Val  Thr  Ile  Ile  Ala  Thr  Asp  Lys  Gly  Lys  Pro  Ala  Leu
              115                         120                    125
    Ser  Ser  Arg  Thr  Ser  Ile  Thr  Leu  His  Ile  Ser  Asp  Ile  Asn  Asp  Asn
         130                         135                    140
    Ala  Pro
    145
```

( 2 ) INFORMATION FOR SEQ ID NO:92:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:92:

```
AAGCGAGTGG  ATTACGAGGC  CACTCGGAAT  TATAAGCTGA  GAGTTAAGGC  TACTGATCTT    60
GGGATTCCAC  CGAGATCTTC  TAACATGACA  CTGTTCATTC  ATGTCCTTGA  TGTTAACGAC   120
AACGCTCCCT  T                                                            131
```

( 2 ) INFORMATION FOR SEQ ID NO:93:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:93:

```
    Lys  Arg  Val  Asp  Tyr  Glu  Ala  Thr  Arg  Asn  Tyr  Lys  Leu  Arg  Val  Lys
    1                   5                          10                          15
    Ala  Thr  Asp  Leu  Gly  Ile  Pro  Pro  Arg  Ser  Ser  Asn  Met  Thr  Leu  Phe
                   20                         25                     30
    Ile  His  Val  Leu  Asp  Val  Asn  Asp  Asn  Ala  Pro
                   35                         40
```

( 2 ) INFORMATION FOR SEQ ID NO:94:

( i ) SEQUENCE CHARACTERISTICS:
        ( A ) LENGTH: 4104 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 495..3572

( x i ) SEQUENCE DESCRIPTION: SEQ ID NO:94:

| | | | | | |
|---|---|---|---|---|---|
| CCTCTATTCG | ACATTCTCTT | TGGATTGTTT | TGCTATAACT | TGAAATTTGG | GATGTCACAA | 60 |
| ACGAAACTGT | CATCTGTTTC | CGCCAAACTG | TGGTTCTGCT | AATCTCCCAG | GCTGGCAGCA | 120 |
| TTGGAGACTT | GCTGACTTCT | TTCATCCCCC | ACTCTTTTCA | CCTGAAATTC | CTTTCCTTGG | 180 |
| TTTTGCTCTA | AGTCCTATGC | TTCAGTCAGG | GGCCAACCAA | ATCTCACTGC | CTCCTTTTA | 240 |
| TCATGAAGCC | TTTGATCACT | GATAGTTCTT | TTTATATCTT | GAAAATCAC | CCTTCCCAGT | 300 |
| ACAGTTAATA | TTTAGTATCT | CTACTCATCT | TGGCACTTAC | TCACAGCTCC | ATAATTCAGT | 360 |
| CGTTTTCGTA | CCTCTTCATG | GTGATGGGGA | GCCCTTTGGA | GGTGGTGACT | GTGCTTTATA | 420 |
| CTCCTCATGA | TGCTTCACAT | GTGGCAGGCG | TGGAGTGCCC | GGAGGCGGCC | CTCCTGATTC | 480 |

```
TGGGGCCTCC CAGG ATG GAG CCC CTG AGG CAC AGC CCA GGC CCT GGG GGG                530
              Met Glu Pro Leu Arg His Ser Pro Gly Pro Gly Gly
               1           5                  10

CAA CGG CTA CTG CTG CCC TCC ATG CTG CTA GCA CTG CTC CTG CTG          578
Gln Arg Leu Leu Leu Pro Ser Met Leu Leu Ala Leu Leu Leu Leu
        15                  20                  25

GCT CCA TCC CCA GGC CAC GCC ACT CGG GTA GTG TAC AAG GTG CCG GAG      626
Ala Pro Ser Pro Gly His Ala Thr Arg Val Val Tyr Lys Val Pro Glu
        30                  35                  40

GAA CAG CCA CCC AAC ACC CTC ATT GGG AGC CTC GCA GCC GAC TAT GGT      674
Glu Gln Pro Pro Asn Thr Leu Ile Gly Ser Leu Ala Ala Asp Tyr Gly
 45                 50                  55                  60

TTT CCA GAT GTG GGG CAC CTG TAC AAG CTA GAG GTG GGT GCC CCG TAC      722
Phe Pro Asp Val Gly His Leu Tyr Lys Leu Glu Val Gly Ala Pro Tyr
            65                  70                  75

CTT CGC GTG GAT GGC AAG ACA GGT GAC ATT TTC ACC ACC GAG ACC TCC      770
Leu Arg Val Asp Gly Lys Thr Gly Asp Ile Phe Thr Thr Glu Thr Ser
        80                  85                  90

ATC GAC CGT GAG GGG CTC CGT GAA TGC CAG AAC CAG CTC CCT GGT GAT      818
Ile Asp Arg Glu Gly Leu Arg Glu Cys Gln Asn Gln Leu Pro Gly Asp
        95                  100                 105

CCC TGC ATC CTG GAG TTT GAG GTA TCT ATC ACA GAC CTC GTG CAG AAT      866
Pro Cys Ile Leu Glu Phe Glu Val Ser Ile Thr Asp Leu Val Gln Asn
    110                 115                 120

GCG AGC CCC CGG CTG CTA GAG GGC CAG ATA GAA GTA CAA GAC ATC AAT      914
Ala Ser Pro Arg Leu Leu Glu Gly Gln Ile Glu Val Gln Asp Ile Asn
125                 130                 135                 140

GAC AAC ACA CCC AAC TTC GCC TCA CCA GTC ATC ACT CTG GCC ATC CCT      962
Asp Asn Thr Pro Asn Phe Ala Ser Pro Val Ile Thr Leu Ala Ile Pro
                145                 150                 155

GAG AAC ACC AAC ATC GGC TCA CTC TTC CCC ATC CCG CTG GCT TCA GAC      1010
Glu Asn Thr Asn Ile Gly Ser Leu Phe Pro Ile Pro Leu Ala Ser Asp
            160                 165                 170

CGT GAT GCT GGT CCC AAC GGT GTG GCA TCC TAT GAG CTG CAG GTG GCA      1058
Arg Asp Ala Gly Pro Asn Gly Val Ala Ser Tyr Glu Leu Gln Val Ala
        175                 180                 185

GAG GAC CAG GAG GAG AAG CAA CCA CAG CTC ATT GTG ATG GGC AAC CTG      1106
Glu Asp Gln Glu Glu Lys Gln Pro Gln Leu Ile Val Met Gly Asn Leu
        190                 195                 200

GAC CGT GAG CGC TGG GAC TCC TAT GAC CTC ACC ATC AAG GTG CAG GAT      1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG      1202
Gly Gly Ser Pro Pro Arg Ala Thr Ser Ala Leu Leu Arg Val Thr Val
                225                 230                 235

CTT GAC ACC AAT GAC AAC GCC CCC AAG TTT GAG CGG CCC TCC TAT GAG      1250
Leu Asp Thr Asn Asp Asn Ala Pro Lys Phe Glu Arg Pro Ser Tyr Glu
            240                 245                 250
```

| | | | | | | | | | | | | | | | | |
|---|---|---|---|---|---|---|---|---|---|---|---|---|---|---|---|---|
| GCC | GAA | CTA | TCT | GAG | AAT | AGC | CCC | ATA | GGC | CAC | TCG | GTC | ATC | CAG | GTG | 1298 |
| Ala | Glu | Leu | Ser | Glu | Asn | Ser | Pro | Ile | Gly | His | Ser | Val | Ile | Gln | Val | |
| | | 255 | | | | | 260 | | | | | 265 | | | | |
| AAG | GCC | AAT | GAC | TCA | GAC | CAA | GGT | GCC | AAT | GCA | GAA | ATC | GAA | TAC | ACA | 1346 |
| Lys | Ala | Asn | Asp | Ser | Asp | Gln | Gly | Ala | Asn | Ala | Glu | Ile | Glu | Tyr | Thr | |
| | 270 | | | | | 275 | | | | | 280 | | | | | |
| TTC | CAC | CAG | GCG | CCC | GAA | GTT | GTG | AGG | CGT | CTT | CTT | CGA | CTG | GAC | AGG | 1394 |
| Phe | His | Gln | Ala | Pro | Glu | Val | Val | Arg | Arg | Leu | Leu | Arg | Leu | Asp | Arg | |
| 285 | | | | | 290 | | | | | 295 | | | | | 300 | |
| AAC | ACT | GGA | CTT | ATC | ACT | GTT | CAG | GGC | CCG | GTG | GAC | CGT | GAG | GAC | CTA | 1442 |
| Asn | Thr | Gly | Leu | Ile | Thr | Val | Gln | Gly | Pro | Val | Asp | Arg | Glu | Asp | Leu | |
| | | | | 305 | | | | | 310 | | | | | 315 | | |
| AGC | ACC | CTG | CGC | TTC | TCA | GTG | CTT | GCT | AAG | GAC | CGA | GGC | ACC | AAC | CCC | 1490 |
| Ser | Thr | Leu | Arg | Phe | Ser | Val | Leu | Ala | Lys | Asp | Arg | Gly | Thr | Asn | Pro | |
| | | | 320 | | | | | 325 | | | | | 330 | | | |
| AAG | AGT | GCC | CGT | GCC | CAG | GTG | GTT | GTG | ACC | GTG | AAG | GAC | ATG | AAT | GAC | 1538 |
| Lys | Ser | Ala | Arg | Ala | Gln | Val | Val | Val | Thr | Val | Lys | Asp | Met | Asn | Asp | |
| | | 335 | | | | | 340 | | | | | 345 | | | | |
| AAT | GCC | CCC | ACC | ATT | GAG | ATC | CGG | GGC | ATA | GGG | CTA | GTG | ACT | CAT | CAA | 1586 |
| Asn | Ala | Pro | Thr | Ile | Glu | Ile | Arg | Gly | Ile | Gly | Leu | Val | Thr | His | Gln | |
| | 350 | | | | | 355 | | | | | 360 | | | | | |
| GAT | GGG | ATG | GCT | AAC | ATC | TCA | GAG | GAT | GTG | GCA | GAG | GAG | ACA | GCT | GTG | 1634 |
| Asp | Gly | Met | Ala | Asn | Ile | Ser | Glu | Asp | Val | Ala | Glu | Glu | Thr | Ala | Val | |
| 365 | | | | | 370 | | | | | 375 | | | | | 380 | |
| GCC | CTG | GTG | CAG | GTG | TCT | GAC | CGA | GAT | GAG | GGA | GAG | AAT | GCA | GCT | GTC | 1682 |
| Ala | Leu | Val | Gln | Val | Ser | Asp | Arg | Asp | Glu | Gly | Glu | Asn | Ala | Ala | Val | |
| | | | | 385 | | | | | 390 | | | | | 395 | | |
| ACC | TGT | GTG | GTG | GCA | GGT | GAT | GTG | CCC | TTC | CAG | CTG | CGC | CAG | GCC | AGT | 1730 |
| Thr | Cys | Val | Val | Ala | Gly | Asp | Val | Pro | Phe | Gln | Leu | Arg | Gln | Ala | Ser | |
| | | | 400 | | | | | 405 | | | | | 410 | | | |
| GAG | ACA | GGC | AGT | GAC | AGC | AAG | AAG | AAG | TAT | TTC | CTG | CAG | ACT | ACC | ACC | 1778 |
| Glu | Thr | Gly | Ser | Asp | Ser | Lys | Lys | Lys | Tyr | Phe | Leu | Gln | Thr | Thr | Thr | |
| | | 415 | | | | | 420 | | | | | 425 | | | | |
| CCG | CTA | GAC | TAC | GAG | AAG | GTC | AAA | GAC | TAC | ACC | ATT | GAG | ATT | GTG | GCT | 1826 |
| Pro | Leu | Asp | Tyr | Glu | Lys | Val | Lys | Asp | Tyr | Thr | Ile | Glu | Ile | Val | Ala | |
| | 430 | | | | | 435 | | | | | 440 | | | | | |
| GTG | GAC | TCT | GGC | AAC | CCC | CCA | CTC | TCC | AGC | ACT | AAC | TCC | CTC | AAG | GTG | 1874 |
| Val | Asp | Ser | Gly | Asn | Pro | Pro | Leu | Ser | Ser | Thr | Asn | Ser | Leu | Lys | Val | |
| 445 | | | | | 450 | | | | | 455 | | | | | 460 | |
| CAG | GTG | GTG | GAC | GTC | AAT | GAC | AAC | GCA | CCT | GTC | TTC | ACT | CAG | AGT | GTC | 1922 |
| Gln | Val | Val | Asp | Val | Asn | Asp | Asn | Ala | Pro | Val | Phe | Thr | Gln | Ser | Val | |
| | | | | 465 | | | | | 470 | | | | | 475 | | |
| ACT | GAG | GTC | GCC | TTC | CCG | GAA | AAC | AAC | AAG | CCT | GGT | GAA | GTG | ATT | GCT | 1970 |
| Thr | Glu | Val | Ala | Phe | Pro | Glu | Asn | Asn | Lys | Pro | Gly | Glu | Val | Ile | Ala | |
| | | | 480 | | | | | 485 | | | | | 490 | | | |
| GAG | ATC | ACT | GCC | AGT | GAT | GCT | GAC | TCT | GGC | TCT | AAT | GCT | GAG | CTG | GTT | 2018 |
| Glu | Ile | Thr | Ala | Ser | Asp | Ala | Asp | Ser | Gly | Ser | Asn | Ala | Glu | Leu | Val | |
| | | 495 | | | | | 500 | | | | | 505 | | | | |
| TAC | TCT | CTG | GAG | CCT | GAG | CCG | GCT | GCT | AAG | GGC | CTC | TTC | ACC | ATC | TCA | 2066 |
| Tyr | Ser | Leu | Glu | Pro | Glu | Pro | Ala | Ala | Lys | Gly | Leu | Phe | Thr | Ile | Ser | |
| | 510 | | | | | 515 | | | | | 520 | | | | | |
| CCC | GAG | ACT | GGA | GAG | ATC | CAG | GTG | AAG | ACA | TCT | CTG | GAT | CGG | GAA | CAG | 2114 |
| Pro | Glu | Thr | Gly | Glu | Ile | Gln | Val | Lys | Thr | Ser | Leu | Asp | Arg | Glu | Gln | |
| 525 | | | | | 530 | | | | | 535 | | | | | 540 | |
| CGG | GAG | AGC | TAT | GAG | TTG | AAG | GTG | GTG | GCA | GCT | GAC | CGG | GGC | AGT | CCT | 2162 |
| Arg | Glu | Ser | Tyr | Glu | Leu | Lys | Val | Val | Ala | Ala | Asp | Arg | Gly | Ser | Pro | |
| | | | | 545 | | | | | 550 | | | | | 555 | | |
| AGC | CTC | CAG | GGC | ACA | GCC | ACT | GTC | CTT | GTC | AAT | GTG | CTG | GAC | TGC | AAT | 2210 |
| Ser | Leu | Gln | Gly | Thr | Ala | Thr | Val | Leu | Val | Asn | Val | Leu | Asp | Cys | Asn | |
| | | | | 560 | | | | | 565 | | | | | 570 | | |

```
GAC AAT GAC CCC AAA TTT ATG CTG AGT GGC TAC AAC TTC TCA GTG ATG         2258
Asp Asn Asp Pro Lys Phe Met Leu Ser Gly Tyr Asn Phe Ser Val Met
            575             580                 585

GAG AAC ATG CCA GCA CTG AGT CCA GTG GGC ATG GTG ACT GTC ATT GAT         2306
Glu Asn Met Pro Ala Leu Ser Pro Val Gly Met Val Thr Val Ile Asp
            590             595                 600

GGA GAC AAG GGG GAG AAT GCC CAG GTG CAG CTC TCA GTG GAG CAG GAC         2354
Gly Asp Lys Gly Glu Asn Ala Gln Val Gln Leu Ser Val Glu Gln Asp
605             610             615                 620

AAC GGT GAC TTT GTT ATC CAG AAT GGC ACA GGC ACC ATC CTA TCC AGC         2402
Asn Gly Asp Phe Val Ile Gln Asn Gly Thr Gly Thr Ile Leu Ser Ser
                    625             630             635

CTG AGC TTT GAT CGA GAG CAA CAA AGC ACC TAC ACC TTC CAG CTG AAG         2450
Leu Ser Phe Asp Arg Glu Gln Gln Ser Thr Tyr Thr Phe Gln Leu Lys
                640             645                 650

GCA GTG GAT GGT GGC GTC CCA CCT CGC TCA GCT TAC GTT GGT GTC ACC         2498
Ala Val Asp Gly Gly Val Pro Pro Arg Ser Ala Tyr Val Gly Val Thr
            655             660                 665

ATC AAT GTG CTG GAC GAG AAT GAC AAC GCA CCC TAT ATC ACT GCC CCT         2546
Ile Asn Val Leu Asp Glu Asn Asp Asn Ala Pro Tyr Ile Thr Ala Pro
670             675             680

TCT AAC ACC TCT CAC AAG CTG CTG ACC CCC CAG ACA CGT CTT GGT GAG         2594
Ser Asn Thr Ser His Lys Leu Leu Thr Pro Gln Thr Arg Leu Gly Glu
685             690             695                 700

ACG GTC AGC CAG GTG GCA GCC GAG GAC TTT GAC TCT GGT GTC AAT GCC         2642
Thr Val Ser Gln Val Ala Ala Glu Asp Phe Asp Ser Gly Val Asn Ala
                    705             710             715

GAG CTG ATC TAC AGC ATT GCA GGT GGC AAC CCT TAT GGA CTC TTC CAG         2690
Glu Leu Ile Tyr Ser Ile Ala Gly Gly Asn Pro Tyr Gly Leu Phe Gln
                720             725             730

ATT GGG TCA CAT TCA GGT GCC ATC ACC CTG GAG AAG GAG ATT GAG CGG         2738
Ile Gly Ser His Ser Gly Ala Ile Thr Leu Glu Lys Glu Ile Glu Arg
            735             740                 745

CGC CAC CAT GGG CTA CAC CGC CTG GTG GTG AAG GTC AGT GAC CGC GGC         2786
Arg His His Gly Leu His Arg Leu Val Val Lys Val Ser Asp Arg Gly
            750             755                 760

AAG CCC CCA CGC TAT GGC ACA GCC TTG GTC CAT CTT TAT GTC AAT GAG         2834
Lys Pro Pro Arg Tyr Gly Thr Ala Leu Val His Leu Tyr Val Asn Glu
765             770             775                 780

ACT CTG GCC AAC CGC ACG CTG CTG GAG ACC CTC CTG GGC CAC AGC CTG         2882
Thr Leu Ala Asn Arg Thr Leu Leu Glu Thr Leu Leu Gly His Ser Leu
                785             790             795

GAC ACG CCG CTG GAT ATT GAC ATT GCT GGG GAT CCA GAA TAT GAG CGC         2930
Asp Thr Pro Leu Asp Ile Asp Ile Ala Gly Asp Pro Glu Tyr Glu Arg
            800             805                 810

TCC AAG CAG CGT GGC AAC ATT CTC TTT GGT GTG GTG GCT GGT GTG GTG         2978
Ser Lys Gln Arg Gly Asn Ile Leu Phe Gly Val Val Ala Gly Val Val
            815             820                 825

GCC GTG GCC TTG CTC ATC GCC CTG GCG GTT CTT GTG CGC TAC TGC AGA         3026
Ala Val Ala Leu Leu Ile Ala Leu Ala Val Leu Val Arg Tyr Cys Arg
            830             835                 840

CAG CGG GAG GCC AAA AGT GGT TAC CAG GCT GGT AAG AAG GAG ACC AAG         3074
Gln Arg Glu Ala Lys Ser Gly Tyr Gln Ala Gly Lys Lys Glu Thr Lys
845             850             855                 860

GAC CTG TAT GCC CCC AAG CCC AGT GGC AAG GCC TCC AAG GGA AAC AAA         3122
Asp Leu Tyr Ala Pro Lys Pro Ser Gly Lys Ala Ser Lys Gly Asn Lys
                865             870             875

AGC AAA GGC AAG AAG AGC AAG TCC CCA AAG CCC GTG AAG CCA GTG GAG         3170
Ser Lys Gly Lys Lys Ser Lys Ser Pro Lys Pro Val Lys Pro Val Glu
            880             885                 890
```

| | | | | | | | | | | | | | | | | |
|---|---|---|---|---|---|---|---|---|---|---|---|---|---|---|---|---|
| GAC | GAG | GAT | GAG | GCC | GGG | CTG | CAG | AAG | TCC | CTC | AAG | TTC | AAC | CTG | ATG | 3218 |
| Asp | Glu | Asp | Glu | Ala | Gly | Leu | Gln | Lys | Ser | Leu | Lys | Phe | Asn | Leu | Met | |
| | | 895 | | | | 900 | | | | | | 905 | | | | |
| AGC | GAT | GCC | CCT | GGG | GAC | AGT | CCC | CGC | ATC | CAC | CTG | CCC | CTC | AAC | TAC | 3266 |
| Ser | Asp | Ala | Pro | Gly | Asp | Ser | Pro | Arg | Ile | His | Leu | Pro | Leu | Asn | Tyr | |
| | | 910 | | | | | 915 | | | | 920 | | | | | |
| CCA | CCA | GGC | AGC | CCT | GAC | CTG | GGC | CGC | CAC | TAT | CGC | TCT | AAC | TCC | CCA | 3314 |
| Pro | Pro | Gly | Ser | Pro | Asp | Leu | Gly | Arg | His | Tyr | Arg | Ser | Asn | Ser | Pro | |
| 925 | | | | | 930 | | | | | 935 | | | | | 940 | |
| CTG | CCT | TCC | ATC | CAG | CTG | CAG | CCC | CAG | TCA | CCC | TCA | GCC | TCC | AAG | AAG | 3362 |
| Leu | Pro | Ser | Ile | Gln | Leu | Gln | Pro | Gln | Ser | Pro | Ser | Ala | Ser | Lys | Lys | |
| | | | | 945 | | | | | 950 | | | | | 955 | | |
| CAC | CAG | GTG | GTA | CAG | GAC | CTG | CCA | CCT | GCA | AAC | ACA | TTC | GTG | GGC | ACC | 3410 |
| His | Gln | Val | Val | Gln | Asp | Leu | Pro | Pro | Ala | Asn | Thr | Phe | Val | Gly | Thr | |
| | | | 960 | | | | | 965 | | | | | 970 | | | |
| GGG | GAC | ACC | ACG | TCC | ACG | GGC | TCT | GAG | CAG | TAC | TCC | GAC | TAC | AGC | TAC | 3458 |
| Gly | Asp | Thr | Thr | Ser | Thr | Gly | Ser | Glu | Gln | Tyr | Ser | Asp | Tyr | Ser | Tyr | |
| | | 975 | | | | | 980 | | | | | 985 | | | | |
| CGC | ACC | AAC | CCC | CCC | AAA | TAC | CCC | AGC | AAG | CAG | GTA | GGC | CAG | CCC | TTT | 3506 |
| Arg | Thr | Asn | Pro | Pro | Lys | Tyr | Pro | Ser | Lys | Gln | Val | Gly | Gln | Pro | Phe | |
| | | 990 | | | | | 995 | | | | | 1000 | | | | |
| CAG | CTC | AGC | ACA | CCC | CAG | CCC | CTA | CCC | CAC | CCC | TAC | CAC | GGA | GCC | ATC | 3554 |
| Gln | Leu | Ser | Thr | Pro | Gln | Pro | Leu | Pro | His | Pro | Tyr | His | Gly | Ala | Ile | |
| 1005 | | | | | 1010 | | | | 1015 | | | | | 1020 | | |
| TGG | ACC | GAG | GTG | TGG | GAG | TGATGGAGCA | | GGTTACTGT | | GCCTGCCCGT | | | | | | 3602 |
| Trp | Thr | Glu | Val | Trp | Glu | | | | | | | | | | | |
| | | | | 1025 | | | | | | | | | | | | |

| | | | | |
|---|---|---|---|---|
| GTTGGGGGCC | AGCCTGAGCC | AGCAGTGGGA | GGTGGGGCCT | TAGTGCCTCA | CCGGGCACAC | 3662 |
| GGATTAGGCT | GAGTGAAGAT | TAAGGGAGGG | TGTGCTCTGT | GGTCTCCTCC | CTGCCCTCTC | 3722 |
| CCCACTGGGG | AGAGACCTGT | GATTTGCCAA | GTCCCTGGAC | CCTGGACCAG | CTACTGGGCC | 3782 |
| TTATGGGTTG | GGGGTGGTAG | GCAGGTGAGC | GTAAGTGGGG | AGGGAAATGG | GTAAGAAGTC | 3842 |
| TACTCCAAAC | CTAGGTCTCT | ATGTCAGACC | AGACCTAGGT | GCTTCTCTAG | GAGGGAAACA | 3902 |
| GGGAGACCTG | GGGTCCTGTG | GATAACTGAG | TGGGGAGTCT | GCCAGGGGAG | GGCACCTTCC | 3962 |
| CATTGTGCCT | TCTGTGTGTA | TTGTGCATTA | ACCTCTTCCT | CACCACTAGG | CTTCTGGGGC | 4022 |
| TGGGTCCCAC | ATGCCCTTGA | CCCTGACAAT | AAAGTTCTCT | ATTTTGGAA | AAAAAAAAA | 4082 |
| AAAAAAAAAA | AAAAAAAAAA | AA | | | | 4104 |

( 2 ) INFORMATION FOR SEQ ID NO:95:

( i ) SEQUENCE CHARACTERISTICS:
        ( A ) LENGTH: 1026 amino acids
        ( B ) TYPE: amino acid
        ( D ) TOPOLOGY: linear ( i i ) MOLECULE TYPE: protein ( x i ) SEQUENCE DESCRIPTION: SEQ ID NO:95:

| | | | | | | | | | | | | | |
|---|---|---|---|---|---|---|---|---|---|---|---|---|---|
| Met | Glu | Pro | Leu | Arg | His | Ser | Pro | Gly | Pro | Gly | Gln | Arg | Leu | Leu |
| 1 | | | | 5 | | | | | 10 | | | | | 15 |
| Leu | Pro | Ser | Met | Leu | Leu | Ala | Leu | Leu | Leu | Leu | Ala | Pro | Ser | Pro |
| | | | 20 | | | | | 25 | | | | | 30 | |
| Gly | His | Ala | Thr | Arg | Val | Val | Tyr | Lys | Val | Pro | Glu | Glu | Pro | Pro |
| | | 35 | | | | | 40 | | | | | 45 | | |
| Asn | Thr | Leu | Ile | Gly | Ser | Leu | Ala | Ala | Asp | Tyr | Gly | Phe | Pro | Asp | Val |
| | 50 | | | | | 55 | | | | | 60 | | | | |
| Gly | His | Leu | Tyr | Lys | Leu | Glu | Val | Gly | Ala | Pro | Tyr | Leu | Arg | Val | Asp |

```
Gly Lys Thr Gly Asp Ile Phe Thr Thr Glu Thr Ser Ile Asp Arg Glu
                 85                  90                  95
Gly Leu Arg Glu Cys Gln Asn Gln Leu Pro Gly Asp Pro Cys Ile Leu
            100                 105                 110
Glu Phe Glu Val Ser Ile Thr Asp Leu Val Gln Asn Ala Ser Pro Arg
        115                 120                 125
Leu Leu Glu Gly Gln Ile Glu Val Gln Asp Ile Asn Asp Asn Thr Pro
130                 135                 140
Asn Phe Ala Ser Pro Val Ile Thr Leu Ala Ile Pro Glu Asn Thr Asn
145                 150                 155                 160
Ile Gly Ser Leu Phe Pro Ile Pro Leu Ala Ser Asp Arg Asp Ala Gly
                165                 170                 175
Pro Asn Gly Val Ala Ser Tyr Glu Leu Gln Val Ala Glu Asp Gln Glu
            180                 185                 190
Glu Lys Gln Pro Gln Leu Ile Val Met Gly Asn Leu Asp Arg Glu Arg
        195                 200                 205
Trp Asp Ser Tyr Asp Leu Thr Ile Lys Val Gln Asp Gly Gly Ser Pro
210                 215                 220
Pro Arg Ala Thr Ser Ala Leu Leu Arg Val Thr Val Leu Asp Thr Asn
225                 230                 235                 240
Asp Asn Ala Pro Lys Phe Glu Arg Pro Ser Tyr Glu Ala Glu Leu Ser
                245                 250                 255
Glu Asn Ser Pro Ile Gly His Ser Val Ile Gln Val Lys Ala Asn Asp
            260                 265                 270
Ser Asp Gln Gly Ala Asn Ala Glu Ile Glu Tyr Thr Phe His Gln Ala
        275                 280                 285
Pro Glu Val Val Arg Arg Leu Leu Arg Leu Asp Arg Asn Thr Gly Leu
290                 295                 300
Ile Thr Val Gln Gly Pro Val Asp Arg Glu Asp Leu Ser Thr Leu Arg
305                 310                 315                 320
Phe Ser Val Leu Ala Lys Asp Arg Gly Thr Asn Pro Lys Ser Ala Arg
                325                 330                 335
Ala Gln Val Val Val Thr Val Lys Asp Met Asn Asp Asn Ala Pro Thr
            340                 345                 350
Ile Glu Ile Arg Gly Ile Gly Leu Val Thr His Gln Asp Gly Met Ala
        355                 360                 365
Asn Ile Ser Glu Asp Val Ala Glu Glu Thr Ala Val Ala Leu Val Gln
370                 375                 380
Val Ser Asp Arg Asp Glu Gly Glu Asn Ala Ala Val Thr Cys Val Val
385                 390                 395                 400
Ala Gly Asp Val Pro Phe Gln Leu Arg Gln Ala Ser Glu Thr Gly Ser
                405                 410                 415
Asp Ser Lys Lys Lys Tyr Phe Leu Gln Thr Thr Thr Pro Leu Asp Tyr
            420                 425                 430
Glu Lys Val Lys Asp Tyr Thr Ile Glu Ile Val Ala Val Asp Ser Gly
        435                 440                 445
Asn Pro Pro Leu Ser Ser Thr Asn Ser Leu Lys Val Gln Val Val Asp
450                 455                 460
Val Asn Asp Asn Ala Pro Val Phe Thr Gln Ser Val Thr Glu Val Ala
465                 470                 475                 480
Phe Pro Glu Asn Asn Lys Pro Gly Glu Val Ile Ala Glu Ile Thr Ala
                485                 490                 495
```

```
Ser Asp Ala Asp Ser Gly Ser Asn Ala Glu Leu Val Tyr Ser Leu Glu
            500             505                 510

Pro Glu Pro Ala Ala Lys Gly Leu Phe Thr Ile Ser Pro Glu Thr Gly
        515             520                 525

Glu Ile Gln Val Lys Thr Ser Leu Asp Arg Glu Gln Arg Glu Ser Tyr
        530             535                 540

Glu Leu Lys Val Val Ala Ala Asp Arg Gly Ser Pro Ser Leu Gln Gly
545                 550             555                         560

Thr Ala Thr Val Leu Val Asn Val Leu Asp Cys Asn Asp Asn Asp Pro
                565             570                 575

Lys Phe Met Leu Ser Gly Tyr Asn Phe Ser Val Met Glu Asn Met Pro
            580             585                 590

Ala Leu Ser Pro Val Gly Met Val Thr Val Ile Asp Gly Asp Lys Gly
        595             600             605

Glu Asn Ala Gln Val Gln Leu Ser Val Glu Gln Asp Asn Gly Asp Phe
        610             615             620

Val Ile Gln Asn Gly Thr Gly Thr Ile Leu Ser Ser Leu Ser Phe Asp
625                 630             635                         640

Arg Glu Gln Gln Ser Thr Tyr Thr Phe Gln Leu Lys Ala Val Asp Gly
                645             650                 655

Gly Val Pro Pro Arg Ser Ala Tyr Val Gly Val Thr Ile Asn Val Leu
            660             665                 670

Asp Glu Asn Asp Asn Ala Pro Tyr Ile Thr Ala Pro Ser Asn Thr Ser
        675             680                 685

His Lys Leu Leu Thr Pro Gln Thr Arg Leu Gly Glu Thr Val Ser Gln
        690             695             700

Val Ala Ala Glu Asp Phe Asp Ser Gly Val Asn Ala Glu Leu Ile Tyr
705                 710             715                         720

Ser Ile Ala Gly Gly Asn Pro Tyr Gly Leu Phe Gln Ile Gly Ser His
                725             730                 735

Ser Gly Ala Ile Thr Leu Glu Lys Glu Ile Glu Arg Arg His His Gly
            740             745                 750

Leu His Arg Leu Val Val Lys Val Ser Asp Arg Gly Lys Pro Pro Arg
        755             760                 765

Tyr Gly Thr Ala Leu Val His Leu Tyr Val Asn Glu Thr Leu Ala Asn
    770             775                 780

Arg Thr Leu Leu Glu Thr Leu Leu Gly His Ser Leu Asp Thr Pro Leu
785                 790             795                         800

Asp Ile Asp Ile Ala Gly Asp Pro Glu Tyr Glu Arg Ser Lys Gln Arg
                805             810                 815

Gly Asn Ile Leu Phe Gly Val Val Ala Gly Val Val Ala Val Ala Leu
            820             825                 830

Leu Ile Ala Leu Ala Val Leu Val Arg Tyr Cys Arg Gln Arg Glu Ala
        835             840                 845

Lys Ser Gly Tyr Gln Ala Gly Lys Lys Glu Thr Lys Asp Leu Tyr Ala
    850             855                 860

Pro Lys Pro Ser Gly Lys Ala Ser Lys Gly Asn Lys Ser Lys Gly Lys
865                 870             875                         880

Lys Ser Lys Ser Pro Lys Pro Val Lys Pro Val Glu Asp Glu Asp Glu
                885             890                 895

Ala Gly Leu Gln Lys Ser Leu Lys Phe Asn Leu Met Ser Asp Ala Pro
            900             905                 910

Gly Asp Ser Pro Arg Ile His Leu Pro Leu Asn Tyr Pro Pro Gly Ser
        915             920                 925
```

| | | | | | | | | | | | | | | |
|---|---|---|---|---|---|---|---|---|---|---|---|---|---|---|
| Pro | Asp<br>930 | Leu | Gly | Arg | His | Tyr<br>935 | Arg | Ser | Asn | Ser | Pro<br>940 | Leu | Pro | Ser | Ile |
| Gln<br>945 | Leu | Gln | Pro | Gln | Ser<br>950 | Pro | Ser | Ala | Ser | Lys<br>955 | Lys | His | Gln | Val | Val<br>960 |
| Gln | Asp | Leu | Pro | Pro<br>965 | Ala | Asn | Thr | Phe | Val<br>970 | Gly | Thr | Gly | Asp<br>975 | Thr | Thr |
| Ser | Thr | Gly | Ser<br>980 | Glu | Gln | Tyr | Ser | Asp<br>985 | Tyr | Ser | Tyr | Arg<br>990 | Thr | Asn | Pro |
| Pro | Lys | Tyr<br>995 | Pro | Ser | Lys | Gln | Val<br>1000 | Gly | Gln | Pro | Phe | Gln<br>1005 | Leu | Ser | Thr |
| Pro | Gln<br>1010 | Pro | Leu | Pro | His | Pro<br>1015 | Tyr | His | Gly | Ala | Ile<br>1020 | Trp | Thr | Glu | Val |
| Trp | Glu<br>1025 | | | | | | | | | | | | | | |

( 2 ) INFORMATION FOR SEQ ID NO:96:

( i ) SEQUENCE CHARACTERISTICS:
        ( A ) LENGTH: 4705 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..2827

( x i ) SEQUENCE DESCRIPTION: SEQ ID NO:96:

```
CGAAAGCCAT GTCGGACTCG TCGCCCAGCG CCCAAGCGCT AACCCGCTGA AAGTTTCTCA        60

GCGAAATCTC AGGGACGATC TGGACCCCGC TGAGAGGAAC TGCTTTTGAG TGAG ATG         117
                                                             Met
                                                              1
```

| | | | | | | | | | | | | | | | | |
|---|---|---|---|---|---|---|---|---|---|---|---|---|---|---|---|---|
| GTC | CCA | GAG | GCC | TGG | AGG | AGC | GGA | CTG | GTA | AGC | ACC | GGG | AGG | GTA | GTG | 165 |
| Val | Pro | Glu | Ala<br>5 | Trp | Arg | Ser | Gly | Leu<br>10 | Val | Ser | Thr | Gly | Arg<br>15 | Val | Val | |
| GGA | GTT | TTG | CTT | CTG | CTT | GGT | GCC | TTG | AAC | AAG | GCT | TCC | ACG | GTC | ATT | 213 |
| Gly | Val | Leu<br>20 | Leu | Leu | Leu | Gly | Ala<br>25 | Leu | Asn | Lys | Ala | Ser<br>30 | Thr | Val | Ile | |
| CAC | TAT | GAG | ATC | CCG | GAG | GAA | AGA | GAG | AAG | GGT | TTC | GCT | GTG | GGC | AAC | 261 |
| His | Tyr<br>35 | Glu | Ile | Pro | Glu | Glu<br>40 | Arg | Glu | Lys | Gly | Phe<br>45 | Ala | Val | Gly | Asn | |
| GTG | GTC | GCG | AAC | CTT | GGT | TTG | GAT | CTC | GGT | AGC | CTC | TCA | GCC | CGC | AGG | 309 |
| Val<br>50 | Val | Ala | Asn | Leu | Gly<br>55 | Leu | Asp | Leu | Gly | Ser<br>60 | Leu | Ser | Ala | Arg | Arg<br>65 | |
| TTC | CCG | GTG | GTG | TCT | GGA | GCT | AGC | CGA | AGA | TTC | TTT | GAG | GTG | AAC | CGG | 357 |
| Phe | Pro | Val | Val | Ser<br>70 | Gly | Ala | Ser | Arg | Arg<br>75 | Phe | Phe | Glu | Val | Asn<br>80 | Arg | |
| GAG | ACC | GGA | GAG | ATG | TTT | GTG | AAC | GAC | CGT | CTG | GAT | CGA | GAG | GAG | CTG | 405 |
| Glu | Thr | Gly | Glu | Met<br>85 | Phe | Val | Asn | Asp | Arg<br>90 | Leu | Asp | Arg | Glu | Glu<br>95 | Leu | |
| TGT | GGG | ACA | CTG | CCC | TCT | TGC | ACT | GTA | ACT | CTG | GAG | TTG | GTA | GTG | GAG | 453 |
| Cys | Gly | Thr<br>100 | Leu | Pro | Ser | Cys | Thr<br>105 | Val | Thr | Leu | Glu | Leu<br>110 | Val | Val | Glu | |
| AAC | CCG | CTG | GAG | CTG | TTC | AGC | GTG | GAA | GTG | GTG | ATC | CAG | GAC | ATC | AAC | 501 |
| Asn | Pro<br>115 | Leu | Glu | Leu | Phe | Ser<br>120 | Val | Glu | Val | Val | Ile<br>125 | Gln | Asp | Ile | Asn | |
| GAC | AAC | AAT | CCT | GCT | TTC | CCT | ACC | CAG | GAA | ATG | AAA | TTG | GAG | ATT | AGC | 549 |
| Asp | Asn | Asn<br>130 | Pro | Ala | Phe | Pro<br>135 | Thr | Gln | Glu | Met | Lys<br>140 | Leu | Glu | Ile | Ser<br>145 | |

| | | | | | | | | | | | | | | | | |
|---|---|---|---|---|---|---|---|---|---|---|---|---|---|---|---|---|
| GAG | GCC | GTG | GCT | CCG | GGG | ACG | CGC | TTT | CCG | CTC | GAG | AGC | GCG | CAC | GAT | 597 |
| Glu | Ala | Val | Ala | Pro 150 | Gly | Thr | Arg | Phe | Pro 155 | Leu | Glu | Ser | Ala | His 160 | Asp | |
| CCC | GAT | CTG | GGA | AGC | AAC | TCT | TTA | CAA | ACC | TAT | GAG | CTG | AGC | CGA | AAT | 645 |
| Pro | Asp | Leu | Gly 165 | Ser | Asn | Ser | Leu | Gln 170 | Thr | Tyr | Glu | Leu | Ser 175 | Arg | Asn | |
| GAA | TAC | TTT | GCG | CTT | CGC | GTG | CAG | ACG | CGG | GAG | GAC | AGC | ACC | AAG | TAC | 693 |
| Glu | Tyr | Phe 180 | Ala | Leu | Arg | Val | Gln 185 | Thr | Arg | Glu | Asp | Ser 190 | Thr | Lys | Tyr | |
| GCG | GAG | CTG | GTG | TTG | GAG | CGC | GCC | CTG | GAC | CGA | GAA | CGG | GAG | CCT | AGT | 741 |
| Ala | Glu 195 | Leu | Val | Leu | Glu | Arg 200 | Ala | Leu | Asp | Arg | Glu 205 | Arg | Glu | Pro | Ser | |
| CTC | CAG | TTA | GTG | CTG | ACG | GCG | TTG | GAC | GGA | GGG | ACC | CCA | GCT | CTC | TCC | 789 |
| Leu 210 | Gln | Leu | Val | Leu | Thr 215 | Ala | Leu | Asp | Gly | Gly 220 | Thr | Pro | Ala | Leu | Ser 225 | |
| GCC | AGC | CTG | CCT | ATT | CAC | ATC | AAG | GTG | CTG | GAC | GCG | AAT | GAC | AAT | GCG | 837 |
| Ala | Ser | Leu | Pro | Ile 230 | His | Ile | Lys | Val | Leu 235 | Asp | Ala | Asn | Asp | Asn 240 | Ala | |
| CCT | GTC | TTC | AAC | CAG | TCC | TTG | TAC | CGG | GCG | CGC | GTT | CCT | GGA | GGA | TGC | 885 |
| Pro | Val | Phe | Asn 245 | Gln | Ser | Leu | Tyr | Arg 250 | Ala | Arg | Val | Pro | Gly 255 | Gly | Cys | |
| ACC | TCC | GGC | ACG | CGC | GTG | GTA | CAA | GTC | CTT | GCA | ACG | GAT | CTG | GAT | GAA | 933 |
| Thr | Ser | Gly 260 | Thr | Arg | Val | Val | Gln 265 | Val | Leu | Ala | Thr | Asp 270 | Leu | Asp | Glu | |
| GGC | CCC | AAC | GGT | GAA | ATT | ATT | TAC | TCC | TTC | GGC | AGC | CAC | AAC | CGC | GCC | 981 |
| Gly | Pro | Asn 275 | Gly | Glu | Ile | Ile | Tyr 280 | Ser | Phe | Gly | Ser | His 285 | Asn | Arg | Ala | |
| GGC | GTG | CGG | CAA | CTA | TTC | GCC | TTA | GAC | CTT | GTA | ACC | GGG | ATG | CTG | ACA | 1029 |
| Gly 290 | Val | Arg | Gln | Leu | Phe 295 | Ala | Leu | Asp | Leu | Val 300 | Thr | Gly | Met | Leu | Thr 305 | |
| ATC | AAG | GGT | CGG | CTG | GAC | TTC | GAG | GAC | ACC | AAA | CTC | CAT | GAG | ATT | TAC | 1077 |
| Ile | Lys | Gly | Arg | Leu 310 | Asp | Phe | Glu | Asp | Thr 315 | Lys | Leu | His | Glu | Ile 320 | Tyr | |
| ATC | CAG | GCC | AAA | GAC | AAG | GGC | GCC | AAT | CCC | GAA | GGA | GCA | CAT | TGC | AAA | 1125 |
| Ile | Gln | Ala | Lys 325 | Asp | Lys | Gly | Ala | Asn 330 | Pro | Glu | Gly | Ala | His 335 | Cys | Lys | |
| GTG | TTG | GTG | GAG | GTT | GTG | GAT | GTG | AAT | GAC | AAC | GCC | CCG | GAG | ATC | ACA | 1173 |
| Val | Leu | Val | Glu 340 | Val | Val | Asp | Val | Asn 345 | Asp | Asn | Ala | Pro | Glu 350 | Ile | Thr | |
| GTC | ACC | TCC | GTG | TAC | AGC | CCA | GTA | CCC | GAG | GAT | GCC | TCT | GGG | ACT | GTC | 1221 |
| Val | Thr | Ser 355 | Val | Tyr | Ser | Pro | Val 360 | Pro | Glu | Asp | Ala | Ser 365 | Gly | Thr | Val | |
| ATC | GCT | TTG | CTC | AGT | GTG | ACT | GAC | CTG | GAT | GCT | GGC | GAG | AAC | GGG | CTG | 1269 |
| Ile 370 | Ala | Leu | Leu | Ser | Val 375 | Thr | Asp | Leu | Asp | Ala 380 | Gly | Glu | Asn | Gly | Leu 385 | |
| GTG | ACC | TGC | GAA | GTT | CCA | CCG | GGT | CTC | CCT | TTC | AGC | CTT | ACT | TCT | TCC | 1317 |
| Val | Thr | Cys | Glu | Val 390 | Pro | Pro | Gly | Leu | Pro 395 | Phe | Ser | Leu | Thr | Ser 400 | Ser | |
| CTC | AAG | AAT | TAC | TTC | ACT | TTG | AAA | ACC | AGT | GCA | GAC | CTG | GAT | CGG | GAG | 1365 |
| Leu | Lys | Asn | Tyr 405 | Phe | Thr | Leu | Lys | Thr 410 | Ser | Ala | Asp | Leu | Asp 415 | Arg | Glu | |
| ACT | GTG | CCA | GAA | TAC | AAC | CTC | AGC | ATC | ACC | GCC | CGA | GAC | GCC | GGA | ACC | 1413 |
| Thr | Val | Pro 420 | Glu | Tyr | Asn | Leu | Ser 425 | Ile | Thr | Ala | Arg | Asp 430 | Ala | Gly | Thr | |
| CCT | TCC | CTC | TCA | GCC | CTT | ACA | ATA | GTG | CGT | GTT | CAA | GTG | TCC | GAC | ATC | 1461 |
| Pro | Ser | Leu 435 | Ser | Ala | Leu | Thr | Ile 440 | Val | Arg | Val | Gln | Val 445 | Ser | Asp | Ile | |
| AAT | GAC | AAC | CCT | CCA | CAA | TCT | TCT | CAA | TCT | TCC | TAC | GAC | GTT | TAC | ATT | 1509 |
| Asn | Asp | Asn 450 | Pro | Pro | Gln | Ser | Ser 455 | Gln | Ser | Ser | Tyr | Asp 460 | Val | Tyr | Ile 465 | |

| | | | | | | | | | | | | | | | | |
|---|---|---|---|---|---|---|---|---|---|---|---|---|---|---|---|---|
| GAA | GAA | AAC | AAC | CTC | CCC | GGG | GCT | CCA | ATA | CTA | AAC | CTA | AGT | GTC | TGG | 1557 |
| Glu | Glu | Asn | Asn | Leu<br>470 | Pro | Gly | Ala | Pro | Ile<br>475 | Leu | Asn | Leu | Ser | Val<br>480 | Trp | |
| GAC | CCC | GAC | GCC | CCG | CAG | AAT | GCT | CGG | CTT | TCT | TTC | TTT | CTC | TTG | GAG | 1605 |
| Asp | Pro | Asp | Ala<br>485 | Pro | Gln | Asn | Ala | Arg<br>490 | Leu | Ser | Phe | Phe | Leu<br>495 | Leu | Glu | |
| CAA | GGA | GCT | GAA | ACC | GGG | CTA | GTG | GGT | CGC | TAT | TTC | ACA | ATA | AAT | CGT | 1653 |
| Gln | Gly | Ala<br>500 | Glu | Thr | Gly | Leu | Val<br>505 | Gly | Arg | Tyr | Phe | Thr<br>510 | Ile | Asn | Arg | |
| GAC | AAT | GGC | ATA | GTG | TCA | TCC | TTA | GTG | CCC | CTA | GAC | TAT | GAG | GAT | CGG | 1701 |
| Asp | Asn | Gly<br>515 | Ile | Val | Ser | Ser<br>520 | Leu | Val | Pro | Leu | Asp<br>525 | Tyr | Glu | Asp | Arg | |
| CGG | GAA | TTT | GAA | TTA | ACA | GCT | CAT | ATC | AGC | GAT | GGG | GGC | ACC | CCG | GTC | 1749 |
| Arg<br>530 | Glu | Phe | Glu | Leu | Thr<br>535 | Ala | His | Ile | Ser | Asp<br>540 | Gly | Gly | Thr | Pro | Val<br>545 | |
| CTA | GCC | ACC | AAC | ATC | AGC | GTG | AAC | ATA | TTT | GTC | ACT | GAT | CGC | AAT | GAC | 1797 |
| Leu | Ala | Thr | Asn | Ile<br>550 | Ser | Val | Asn | Ile | Phe<br>555 | Val | Thr | Asp | Arg | Asn<br>560 | Asp | |
| AAT | GCC | CCC | CAG | GTC | CTA | TAT | CCT | CGG | CCA | GGT | GGG | AGC | TCG | GTG | GAG | 1845 |
| Asn | Ala | Pro | Gln<br>565 | Val | Leu | Tyr | Pro | Arg<br>570 | Pro | Gly | Gly | Ser | Ser<br>575 | Val | Glu | |
| ATG | CTG | CCT | CGA | GGT | ACC | TCA | GCT | GGC | CAC | CTA | GTG | TCA | CGG | GTG | GTA | 1893 |
| Met | Leu | Pro<br>580 | Arg | Gly | Thr | Ser | Ala<br>585 | Gly | His | Leu | Val | Ser<br>590 | Arg | Val | Val | |
| GGC | TGG | GAC | GCG | GAT | GCA | GGG | CAC | AAT | GCC | TGG | CTC | TCC | TAC | AGT | CTC | 1941 |
| Gly | Trp | Asp<br>595 | Ala | Asp | Ala | Gly | His<br>600 | Asn | Ala | Trp | Leu | Ser<br>605 | Tyr | Ser | Leu | |
| TTT | GGA | TCC | CCT | AAC | CAG | AGC | CTT | TTT | GCC | ATA | GGG | CTG | CAC | ACT | GGT | 1989 |
| Phe<br>610 | Gly | Ser | Pro | Asn | Gln<br>615 | Ser | Leu | Phe | Ala | Ile<br>620 | Gly | Leu | His | Thr | Gly<br>625 | |
| CAA | ATC | AGT | ACT | GCC | CGT | CCA | GTC | CAA | GAC | ACA | GAT | TCA | CCC | AGG | CAG | 2037 |
| Gln | Ile | Ser | Thr | Ala<br>630 | Arg | Pro | Val | Gln | Asp<br>635 | Thr | Asp | Ser | Pro | Arg<br>640 | Gln | |
| ACT | CTC | ACT | GTC | TTG | ATC | AAA | GAC | AAT | GGG | GAG | CCT | TCG | CTC | TCC | ACC | 2085 |
| Thr | Leu | Thr | Val<br>645 | Leu | Ile | Lys | Asp | Asn<br>650 | Gly | Glu | Pro | Ser | Leu | Ser<br>655 | Thr | |
| ACT | GCT | ACC | CTC | ACT | GTG | TCA | GTA | ACC | GAG | GAC | TCT | CCT | GAA | GCC | CGA | 2133 |
| Thr | Ala | Thr<br>660 | Leu | Thr | Val | Ser | Val<br>665 | Thr | Glu | Asp | Ser | Pro<br>670 | Glu | Ala | Arg | |
| GCC | GAG | TTC | CCC | TCT | GGC | TCT | GCC | CCC | CGG | GAG | CAG | AAA | AAA | AAT | CTC | 2181 |
| Ala | Glu | Phe<br>675 | Pro | Ser | Gly | Ser | Ala<br>680 | Pro | Arg | Glu | Gln | Lys<br>685 | Lys | Asn | Leu | |
| ACC | TTT | TAT | CTA | CTT | CTT | TCT | CTA | ATC | CTG | GTT | TCT | GTG | GGC | TTC | GTG | 2229 |
| Thr<br>690 | Phe | Tyr | Leu | Leu | Leu<br>695 | Ser | Leu | Ile | Leu | Val<br>700 | Ser | Val | Gly | Phe | Val<br>705 | |
| GTC | ACA | GTG | TTC | GGA | GTA | ATC | ATA | TTC | AAA | GTT | TAC | AAG | TGG | AAG | CAG | 2277 |
| Val | Thr | Val | Phe | Gly<br>710 | Val | Ile | Ile | Phe | Lys<br>715 | Val | Tyr | Lys | Trp | Lys<br>720 | Gln | |
| TCT | AGA | GAC | CTA | TAC | CGA | GCC | CCG | GTG | AGC | TCA | CTG | TAC | CGA | ACA | CCA | 2325 |
| Ser | Arg | Asp | Leu<br>725 | Tyr | Arg | Ala | Pro | Val<br>730 | Ser | Ser | Leu | Tyr | Arg<br>735 | Thr | Pro | |
| GGG | CCC | TCC | TTG | CAC | GCG | GAC | GCC | GTG | CGG | GGA | GGC | CTG | ATG | TCG | CCG | 2373 |
| Gly | Pro | Ser<br>740 | Leu | His | Ala | Asp | Ala<br>745 | Val | Arg | Gly | Gly | Leu<br>750 | Met | Ser | Pro | |
| CAC | CTT | TAC | CAT | CAG | GTG | TAT | CTC | ACC | ACG | GAC | TCC | CGC | CGC | AGC | GAC | 2421 |
| His | Leu | Tyr<br>755 | His | Gln | Val | Tyr | Leu<br>760 | Thr | Thr | Asp | Ser | Arg<br>765 | Arg | Ser | Asp | |
| CCG | CTG | CTG | AAG | AAA | CCT | GGT | GCA | GCC | AGT | CCA | CTG | GCC | AGC | CGC | CAG | 2469 |
| Pro<br>770 | Leu | Leu | Lys | Lys<br>775 | Pro | Gly | Ala | Ala | Ser<br>780 | Pro | Leu | Ala | Ser<br>785 | Arg | Gln | |

| | |
|---|---|
| AAC ACG CTG CGG AGC TGT GAT CCG GTG TTC TAT AGG CAG GTG TTG GGT<br>Asn Thr Leu Arg Ser Cys Asp Pro Val Phe Tyr Arg Gln Val Leu Gly<br>790 795 800 | 2517 |
| GCA GAG AGC GCC CCT CCC GGA CAG CAA GCC CCG CCC AAC ACG GAC TGG<br>Ala Glu Ser Ala Pro Pro Gly Gln Gln Ala Pro Pro Asn Thr Asp Trp<br>805 810 815 | 2565 |
| CGT TTC TCT CAG GCC CAG AGA CCC GGC ACC AGC GGC TCC CAA AAT GGC<br>Arg Phe Ser Gln Ala Gln Arg Pro Gly Thr Ser Gly Ser Gln Asn Gly<br>820 825 830 | 2613 |
| GAT GAC ACC GGC ACC TGG CCC AAC AAC CAG TTT GAC ACA GAG ATG CTG<br>Asp Asp Thr Gly Thr Trp Pro Asn Asn Gln Phe Asp Thr Glu Met Leu<br>835 840 845 | 2661 |
| CAA GCC ATG ATC TTG GCG TCC GCC AGT GAA GCT GCT GAT GGG AGC TCC<br>Gln Ala Met Ile Leu Ala Ser Ala Ser Glu Ala Ala Asp Gly Ser Ser<br>850 855 860 865 | 2709 |
| ACC CTG GGA GGG GGT GCC GGC ACC ATG GGA TTG AGC GCC CGC TAC GGA<br>Thr Leu Gly Gly Gly Ala Gly Thr Met Gly Leu Ser Ala Arg Tyr Gly<br>870 875 880 | 2757 |
| CCC CAG TTC ACC CTG CAG CAC GTG CCC GAC TAC CGC CAG AAT GTC TAC<br>Pro Gln Phe Thr Leu Gln His Val Pro Asp Tyr Arg Gln Asn Val Tyr<br>885 890 895 | 2805 |
| ATC CCA GGC AGC AAT GCA CAC T GACCAACGCA GCTGGCAAGC GGATGGCAAG<br>Ile Pro Gly Ser Asn Ala His<br>900 | 2857 |
| GCCCAGCAGG TGGCAATGGC AACAAGAAGA AGTCGGCAAG AAGGAGAAGA AGTAACATGG | 2917 |
| AGGCCAGGCC AAGAGCCACA GGGCAGCCTC TCCCCGAACC AGCCAGCTT CTCCTTACCT | 2977 |
| GCACCCAGGC CTCAGAGTTT CAGGGCTAAC CCCCAGAATA CTGGTAGGGG CCAAGGCATC | 3037 |
| TCCCTTGGAA ACAGAAACAA GTGCCATCAC ACCATCCCTT CCCCAGGTGT AATATCCAAA | 3097 |
| GCAGTTCCGC TGGGAACCCC ATCCAATCAG TGGCTGTACC CATTTGGGTA GTGGGGTTCA | 3157 |
| TGTAGACACC AAGAACCATT TGCCACACCC CGTTTAGTTA CAGCTGAACC CTCCATCTTC | 3217 |
| CAAATCAATC AGGCCCATCC ATCCATGCC TCCCTCCTCC CCACCCCACT CCAACAGTTC | 3277 |
| CTCTTTCCCG AGTAAGGTGG TTGGGGTGTT GAAGTACCAA GTAACCTACA AGCCTCCTAG | 3337 |
| TTCTGAAAAG TTGGAAGGGC ATCATGACCT CTTGGCCTCT CCTTTGATTC TCAATCTTCC | 3397 |
| CCCAAAGCAT GGTTTGGTGC CAGCCCCTTC ACCTCCTTCC AGAGCCCAAG ATCAATGCTC | 3457 |
| AAGTTTTGGA GGACATGATC ACCATCCCCA TGGTACTGAT GCTTGCTGGA TTTAGGGAGG | 3517 |
| GCATTTTGCT ACCAAGCCTC TTCCCAACGC CCTGGGACCA GTCTTCTGTT TTGTTTTTCA | 3577 |
| TTGTTTGAGC TTTCCACTGC ATGCCTTGAC TTCCCCCACC TCCTCCTCAA ACAAGAGACT | 3637 |
| CCACTGCATG TTCCAAGACA GTATGGGGTG GTAAGATAAG GAAGGGAAGT GTGTGGATGT | 3697 |
| GGATGGTGGG GGCATGGACA AAGCTTGACA CATCAAGTTA TCAAGGCCTT GGAGGAGGCT | 3757 |
| CTGTATGTCC TCAGGGGACT GACAACATCC TCCAGATTCC AGCCATAAAC CAATAACTAG | 3817 |
| GCTGGACCCT TCCCACTACA TAATAGGGCT CAGCCAGGCA GCCAGCTTTG GCTGAGCTA | 3877 |
| ACAGGACCAA TGGATTAACT GGCATTTCAG TCCAAGGAAG CTCGAAGCAG GTTTAGGACC | 3937 |
| AGGTCCCCTT GAGAGGTCAG AGGGGCCTCT GTGGGTGCTG GTACTCCAG AGGTGCCACT | 3997 |
| GGTGGAAGGG TCAGCGGAGC CCCAGCAGGA AGGGTGGGCC AGCCAGGCCA TTCTTAGTCC | 4057 |
| CTGGGTTGGG GAGGCAGGGA GCTAGGGCAG GGACCAAATG AACAGAAAGT CTCAGCCCAG | 4117 |
| GATGGGGCTT CTTCAACAGG CCCCTGCCCT CCTGAAGCCT CAGTCCTTCA CCTTGCCAGG | 4177 |
| TGCCGTTTCT CTTCCGTGAA GGCCACTGCC CAGGTCCCCA GTGCGCCCCC TAGTGGCCAT | 4237 |
| AGCCTGGTTA AAGTTCCCCA GTGCCTCCTT GTGATAGACC TTCTTCTCCC ACCCCCTTCT | 4297 |

```
GCCCCTGGGT CCCCGGCCAT CCAGCGGGGC TGCCAGAGAA CCCCAGACCT GCCCTTACAG    4357

TAGTGTAGCG CCCCCTCCCT CTTTCGGCTG GTGTAGAATA GCCAGTAGTG TAGTGCGGTG    4417

TGCTTTTACG TGATGGCGGG TGGGCAGCGG GCGGCGGCGT CCGCGCAGCC GTCTGTCCTT    4477

GATCTGCCCG CGGCGGCCCG TGTTGTGTTT TGTGCTGTGT CCAGCGCTAA GGCGACCCCC    4537

TCCCCCGTAC TGACTTCTCC TATAAGCGCT CTCTTCGCA  TAGTCACGTA GCTCCCACCC    4597

CACCCTCTTC CTGTGTCTCA CGCAAGTTTT ATACTCTAAT ATTTATATGG CTTTTTTTCT    4657

TCGACAAAAA AATAATAAAA CGTTCTTCT  GAAAAAAAAA AAAAAAA               4705
```

( 2 ) INFORMATION FOR SEQ ID NO:97:

( i ) SEQUENCE CHARACTERISTICS:
        ( A ) LENGTH: 904 amino acids
        ( B ) TYPE: amino acid
        ( D ) TOPOLOGY: linear ( i i ) MOLECULE TYPE: protein ( x i ) SEQUENCE DESCRIPTION: SEQ ID NO:97:

```
Met Val Pro Glu Ala Trp Arg Ser Gly Leu Val Ser Thr Gly Arg Val
 1               5                  10                  15

Val Gly Val Leu Leu Leu Leu Gly Ala Leu Asn Lys Ala Ser Thr Val
                20                  25                  30

Ile His Tyr Glu Ile Pro Glu Glu Arg Glu Lys Gly Phe Ala Val Gly
            35                  40                  45

Asn Val Val Ala Asn Leu Gly Leu Asp Leu Gly Ser Leu Ser Ala Arg
        50                  55                  60

Arg Phe Pro Val Val Ser Gly Ala Ser Arg Arg Phe Phe Glu Val Asn
65                  70                  75                  80

Arg Glu Thr Gly Glu Met Phe Val Asn Asp Arg Leu Asp Arg Glu Glu
                85                  90                  95

Leu Cys Gly Thr Leu Pro Ser Cys Thr Val Thr Leu Glu Leu Val Val
                100                 105                 110

Glu Asn Pro Leu Glu Leu Phe Ser Val Glu Val Val Ile Gln Asp Ile
            115                 120                 125

Asn Asp Asn Asn Pro Ala Phe Pro Thr Gln Glu Met Lys Leu Glu Ile
        130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
            180                 185                 190

Tyr Ala Glu Leu Val Leu Glu Arg Ala Leu Asp Arg Glu Arg Glu Pro
        195                 200                 205

Ser Leu Gln Leu Val Leu Thr Ala Leu Asp Gly Gly Thr Pro Ala Leu
210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
            260                 265                 270

Glu Gly Pro Asn Gly Glu Ile Ile Tyr Ser Phe Gly Ser His Asn Arg
        275                 280                 285
```

```
Ala  Gly  Val  Arg  Gln  Leu  Phe  Ala  Leu  Asp  Leu  Val  Thr  Gly  Met  Leu
     290                 295                 300

Thr  Ile  Lys  Gly  Arg  Leu  Asp  Phe  Glu  Asp  Thr  Lys  Leu  His  Glu  Ile
305                      310                 315                           320

Tyr  Ile  Gln  Ala  Lys  Asp  Lys  Gly  Ala  Asn  Pro  Glu  Gly  Ala  His  Cys
                    325                      330                      335

Lys  Val  Leu  Val  Glu  Val  Val  Asp  Val  Asn  Asp  Asn  Ala  Pro  Glu  Ile
               340                 345                      350

Thr  Val  Thr  Ser  Val  Tyr  Ser  Pro  Val  Pro  Glu  Asp  Ala  Ser  Gly  Thr
          355                 360                      365

Val  Ile  Ala  Leu  Leu  Ser  Val  Thr  Asp  Leu  Asp  Ala  Gly  Glu  Asn  Gly
     370                 375                      380

Leu  Val  Thr  Cys  Glu  Val  Pro  Pro  Gly  Leu  Pro  Phe  Ser  Leu  Thr  Ser
385                 390                      395                           400

Ser  Leu  Lys  Asn  Tyr  Phe  Thr  Leu  Lys  Thr  Ser  Ala  Asp  Leu  Asp  Arg
                    405                 410                      415

Glu  Thr  Val  Pro  Glu  Tyr  Asn  Leu  Ser  Ile  Thr  Ala  Arg  Asp  Ala  Gly
               420                 425                      430

Thr  Pro  Ser  Leu  Ser  Ala  Leu  Thr  Ile  Val  Arg  Val  Gln  Val  Ser  Asp
          435                      440                 445

Ile  Asn  Asp  Asn  Pro  Pro  Gln  Ser  Gln  Ser  Ser  Tyr  Asp  Val  Tyr
     450                      455                 460

Ile  Glu  Glu  Asn  Asn  Leu  Pro  Gly  Ala  Pro  Ile  Leu  Asn  Leu  Ser  Val
465                 470                      475                           480

Trp  Asp  Pro  Asp  Ala  Pro  Gln  Asn  Ala  Arg  Leu  Ser  Phe  Phe  Leu  Leu
               485                      490                           495

Glu  Gln  Gly  Ala  Glu  Thr  Gly  Leu  Val  Gly  Arg  Tyr  Phe  Thr  Ile  Asn
               500                 505                      510

Arg  Asp  Asn  Gly  Ile  Val  Ser  Ser  Leu  Val  Pro  Leu  Asp  Tyr  Glu  Asp
          515                 520                      525

Arg  Arg  Glu  Phe  Glu  Leu  Thr  Ala  His  Ile  Ser  Asp  Gly  Gly  Thr  Pro
     530                 535                      540

Val  Leu  Ala  Thr  Asn  Ile  Ser  Val  Asn  Ile  Phe  Val  Thr  Asp  Arg  Asn
545                 550                 555                           560

Asp  Asn  Ala  Pro  Gln  Val  Leu  Tyr  Pro  Arg  Pro  Gly  Gly  Ser  Ser  Val
                    565                 570                      575

Glu  Met  Leu  Pro  Arg  Gly  Thr  Ser  Ala  Gly  His  Leu  Val  Ser  Arg  Val
               580                 585                      590

Val  Gly  Trp  Asp  Ala  Asp  Ala  Gly  His  Asn  Ala  Trp  Leu  Ser  Tyr  Ser
          595                      600                 605

Leu  Phe  Gly  Ser  Pro  Asn  Gln  Ser  Leu  Phe  Ala  Ile  Gly  Leu  His  Thr
     610                 615                      620

Gly  Gln  Ile  Ser  Thr  Ala  Arg  Pro  Val  Gln  Asp  Thr  Asp  Ser  Pro  Arg
625                      630                 635                           640

Gln  Thr  Leu  Thr  Val  Leu  Ile  Lys  Asp  Asn  Gly  Glu  Pro  Ser  Leu  Ser
               645                 650                      655

Thr  Thr  Ala  Thr  Leu  Thr  Val  Ser  Val  Thr  Glu  Asp  Ser  Pro  Glu  Ala
               660                 665                      670

Arg  Ala  Glu  Phe  Pro  Ser  Gly  Ser  Ala  Pro  Arg  Glu  Gln  Lys  Lys  Asn
          675                 680                      685

Leu  Thr  Phe  Tyr  Leu  Leu  Leu  Ser  Leu  Ile  Leu  Val  Ser  Val  Gly  Phe
     690                 695                      700

Val  Val  Thr  Val  Phe  Gly  Val  Ile  Ile  Phe  Lys  Val  Tyr  Lys  Trp  Lys
```

| 705 | | | | | 710 | | | | | 715 | | | | | 720 |
|---|---|---|---|---|---|---|---|---|---|---|---|---|---|---|---|

Gln Ser Arg Asp Leu Tyr Arg Ala Pro Val Ser Ser Leu Tyr Arg Thr
                  725                    730                 735

Pro Gly Pro Ser Leu His Ala Asp Ala Val Arg Gly Gly Leu Met Ser
                  740                    745                 750

Pro His Leu Tyr His Gln Val Tyr Leu Thr Thr Asp Ser Arg Arg Ser
        755                    760                    765

Asp Pro Leu Leu Lys Lys Pro Gly Ala Ala Ser Pro Leu Ala Ser Arg
770                      775                  780

Gln Asn Thr Leu Arg Ser Cys Asp Pro Val Phe Tyr Arg Gln Val Leu
785                    790                795                800

Gly Ala Glu Ser Ala Pro Pro Gly Gln Gln Ala Pro Pro Asn Thr Asp
                805                    810                815

Trp Arg Phe Ser Gln Ala Gln Arg Pro Gly Thr Ser Gly Ser Gln Asn
            820                    825                830

Gly Asp Asp Thr Gly Thr Trp Pro Asn Asn Gln Phe Asp Thr Glu Met
            835                    840                845

Leu Gln Ala Met Ile Leu Ala Ser Ala Ser Glu Ala Ala Asp Gly Ser
850                      855                860

Ser Thr Leu Gly Gly Gly Ala Gly Thr Met Gly Leu Ser Ala Arg Tyr
865                    870                875                880

Gly Pro Gln Phe Thr Leu Gln His Val Pro Asp Tyr Arg Gln Asn Val
            885                    890                895

Tyr Ile Pro Gly Ser Asn Ala His
            900

( 2 ) INFORMATION FOR SEQ ID NO:98:

( i ) SEQUENCE CHARACTERISTICS:
        ( A ) LENGTH: 556 amino acids
        ( B ) TYPE: amino acid
        ( D ) TOPOLOGY: linear ( i i ) MOLECULE TYPE: protein ( x i ) SEQUENCE DESCRIPTION: SEQ ID NO:98:

Asp Trp Val Ile Pro Pro Ile Asn Leu Pro Glu Asn Ser Arg Gly Pro
1                5                    10                15

Phe Pro Gln Glu Leu Val Arg Ile Arg Ser Asp Arg Asp Lys Asn Leu
                20                    25                30

Ser Leu Arg Tyr Thr Val Thr Gly Pro Gly Ala Asp Gln Pro Pro Thr
          35                    40                  45

Gly Ile Phe Ile Ile Asn Pro Ile Ser Gly Gln Leu Ser Val Thr Lys
    50                    55                    60

Pro Leu Asp Arg Glu Gln Ile Ala Arg Phe His Leu Arg Ala His Ala
65                      70                75                80

Val Asp Ile Asn Gly Asn Gln Val Glu Asn Pro Ile Asp Ile Val Ile
                85                    90                95

Asn Val Ile Asp Met Asn Asp Asn Arg Pro Glu Phe Leu His Gln Val
            100                    105              110

Trp Asn Gly Ser Val Pro Glu Gly Ser Lys Pro Gly Thr Tyr Val Met
            115                    120              125

Thr Val Thr Ala Ile Asp Ala Asp Asp Pro Asn Ala Leu Asn Gly Met
        130                    135                140

Leu Arg Tyr Arg Ile Leu Ser Gln Ala Pro Ser Thr Pro Ser Pro Asn
145                      150                155                160

```
Met  Phe  Thr  Ile  Asn  Asn  Glu  Thr  Gly  Asp  Ile  Ile  Thr  Val  Ala  Ala
               165                 170                           175

Gly  Leu  Asp  Arg  Glu  Lys  Val  Gln  Gln  Tyr  Thr  Leu  Ile  Ile  Gln  Ala
               180                 185                           190

Thr  Asp  Met  Glu  Gly  Asn  Pro  Thr  Tyr  Gly  Leu  Ser  Asn  Thr  Ala  Thr
               195                 200                           205

Ala  Val  Ile  Thr  Val  Thr  Asp  Val  Asn  Asp  Asn  Pro  Pro  Glu  Phe  Thr
          210                 215                      220

Ala  Met  Thr  Phe  Tyr  Gly  Glu  Val  Pro  Glu  Asn  Arg  Val  Asp  Ile  Ile
225                      230                 235                           240

Val  Ala  Asn  Leu  Thr  Val  Thr  Asp  Lys  Asp  Gln  Pro  His  Thr  Pro  Ala
               245                 250                           255

Trp  Asn  Ala  Val  Thr  Arg  Ile  Ser  Gly  Gly  Asp  Pro  Thr  Gly  Arg  Phe
               260                 265                           270

Ala  Ile  Gln  Thr  Asp  Pro  Asn  Ser  Asn  Asp  Gly  Leu  Val  Thr  Val  Val
               275                 280                           285

Lys  Pro  Ile  Asp  Phe  Glu  Thr  Asn  Arg  Met  Phe  Val  Leu  Thr  Val  Ala
          290                 295                      300

Ala  Glu  Asn  Gln  Val  Pro  Leu  Ala  Lys  Gly  Ile  Gln  His  Pro  Pro  Gln
305                      310                 315                           320

Ser  Thr  Ala  Thr  Val  Ser  Val  Thr  Val  Ile  Asp  Val  Asn  Glu  Asn  Pro
               325                 330                           335

Tyr  Phe  Ala  Pro  Asn  Pro  Lys  Ile  Ile  Arg  Gln  Glu  Glu  Gly  Leu  His
               340                 345                           350

Ala  Gly  Thr  Met  Leu  Thr  Thr  Phe  Thr  Ala  Gly  Asp  Pro  Asp  Arg  Tyr
          355                 360                      365

Met  Gln  Gln  Asn  Ile  Arg  Tyr  Thr  Lys  Leu  Ser  Asp  Pro  Ala  Asn  Trp
370                      375                 380

Leu  Lys  Ile  Asp  Pro  Val  Asn  Gly  Gln  Ile  Thr  Thr  Ile  Ala  Val  Leu
385                      390                 395                           400

Asp  Arg  Glu  Ser  Pro  Asn  Val  Lys  Asn  Asn  Ile  Tyr  Asn  Ala  Thr  Phe
               405                 410                           415

Leu  Ala  Ser  Asp  Asn  Gly  Ile  Pro  Pro  Met  Ser  Gly  Thr  Gly  Thr  Leu
               420                 425                           430

Gln  Ile  Tyr  Leu  Leu  Asp  Ile  Asn  Asp  Asn  Ala  Pro  Gln  Val  Leu  Pro
          435                 440                      445

Gln  Glu  Ala  Glu  Thr  Cys  Glu  Thr  Pro  Asp  Pro  Asn  Ser  Ile  Asn  Ile
450                      455                 460

Thr  Thr  Ala  Leu  Asp  Tyr  Asp  Ile  Asp  Pro  Asn  Ala  Gly  Pro  Phe  Ala
465                      470                 475                           480

Tyr  Asp  Leu  Pro  Leu  Ser  Pro  Val  Thr  Ile  Lys  Arg  Asn  Trp  Thr  Ile
               485                 490                           495

Thr  Arg  Leu  Asn  Gly  Asp  Phe  Ala  Gln  Leu  Asn  Leu  Lys  Ile  Lys  Phe
               500                 505                           510

Leu  Glu  Ala  Gly  Ile  Tyr  Glu  Val  Pro  Ile  Ile  Ile  Thr  Asp  Ser  Gly
               515                 520                           525

Asn  Pro  Pro  Lys  Ser  Asn  Lys  Ser  Ile  Leu  Arg  Val  Arg  Val  Cys  Gln
               530                 535                           540

Cys  Asp  Phe  Asn  Gly  Asp  Cys  Thr  Asp  Val  Asp  Arg
545                      550                 555
```

( 2 ) INFORMATION FOR SEQ ID NO:99:

( i ) SEQUENCE CHARACTERISTICS:

( A ) LENGTH: 105 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:99:

```
Glu Asp Thr Val Tyr Ser Phe Asp Ile Pro Glu Asn Ala Gln Arg Gly
 1               5                  10                      15

Tyr Gln Val Gly Gln Ile Val Ala Arg Asp Ala Asp Leu Gly Gln Asn
             20                  25                  30

Ala Gln Leu Ser Tyr Gly Val Val Ser Asp Trp Ala Asn Asp Val Phe
         35                  40                  45

Ser Leu Asn Pro Gln Thr Gly Met Leu Thr Leu Thr Ala Arg Leu Asp
     50                  55                  60

Tyr Glu Glu Val Gln His Tyr Ile Leu Ile Val Gln Ala Gln Asp Asn
 65                  70                  75                      80

Gly Gln Pro Ser Leu Ser Thr Thr Ile Thr Val Tyr Cys Asn Val Leu
                 85                  90                  95

Asp Leu Asn Asp Asn Ala Pro Ile Phe
                100             105
```

(2) INFORMATION FOR SEQ ID NO:100:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:100:

```
Asp Xaa Asp Xaa Gly Xaa Asn
 1               5
```

(2) INFORMATION FOR SEQ ID NO:101:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:101:

```
Ala Xaa Asp Xaa Gly Xaa Pro
 1               5
```

(2) INFORMATION FOR SEQ ID NO:102:

(i) SEQUENCE CHARACTERISTICS:
(A) LENGTH: 4650 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 495..4103

(xi) SEQUENCE DESCRIPTION: SEQ ID NO:102:

CCTCTATTCG ACATTCTCTT TGGATTGTTT TGCTATAACT TGAAATTTGG GATGTCACAA    60

| | |
|---|---|
| ACGAAACTGT CATCTGTTTC CGCCAAACTG TGGTTCTGCT AATCTCCCAG GCTGGCAGCA | 120 |
| TTGGAGACTT GCTGACTTCT TTCATCCCCC ACTCTTTTCA CCTGAAATTC CTTTCCTTGG | 180 |
| TTTTGCTCTA AGTCCTATGC TTCAGTCAGG GGCCAACCAA ATCTCACTGC CTCCTTTTTA | 240 |
| TCATGAAGCC TTTGATCACT GATAGTTCTT TTTATATCTT GAAAAATCAC CCTTCCCAGT | 300 |
| ACAGTTAATA TTTAGTATCT CTACTCATCT TGGCACTTAC TCACAGCTCC ATAATTCAGT | 360 |
| CGTTTTCGTA CCTCTTCATG GTGATGGGGA GCCCTTTGGA GGTGGTGACT GTGCTTTATA | 420 |
| CTCCTCATGA TGCTTCACAT GTGGCAGGCG TGGAGTGCCC GGAGGCGGCC CTCCTGATTC | 480 |

```
TGGGGCCTCC CAGG ATG GAG CCC CTG AGG CAC AGC CCA GGC CCT GGG GGG                530
              Met Glu Pro Leu Arg His Ser Pro Gly Pro Gly Gly
               1               5                    10

CAA CGG CTA CTG CTG CCC TCC ATG CTG CTA GCA CTG CTG CTC CTG CTG           578
Gln Arg Leu Leu Leu Pro Ser Met Leu Leu Ala Leu Leu Leu Leu Leu
         15                  20                  25

GCT CCA TCC CCA GGC CAC GCC ACT CGG GTA GTG TAC AAG GTG CCG GAG           626
Ala Pro Ser Pro Gly His Ala Thr Arg Val Val Tyr Lys Val Pro Glu
         30                  35                  40

GAA CAG CCA CCC AAC ACC CTC ATT GGG AGC CTC GCA GCC GAC TAT GGT           674
Glu Gln Pro Pro Asn Thr Leu Ile Gly Ser Leu Ala Ala Asp Tyr Gly
 45                  50                  55                  60

TTT CCA GAT GTG GGG CAC CTG TAC AAG CTA GAG GTG GGT GCC CCG TAC           722
Phe Pro Asp Val Gly His Leu Tyr Lys Leu Glu Val Gly Ala Pro Tyr
                 65                  70                  75

CTT CGC GTG GAT GGC AAG ACA GGT GAC ATT TTC ACC ACC GAG ACC TCC           770
Leu Arg Val Asp Gly Lys Thr Gly Asp Ile Phe Thr Thr Glu Thr Ser
             80                  85                  90

ATC GAC CGT GAG GGG CTC CGT GAA TGC CAG AAC CAG CTC CCT GGT GAT           818
Ile Asp Arg Glu Gly Leu Arg Glu Cys Gln Asn Gln Leu Pro Gly Asp
         95                 100                 105

CCC TGC ATC CTG GAG TTT GAG GTA TCT ATC ACA GAC CTC GTG CAG AAT           866
Pro Cys Ile Leu Glu Phe Glu Val Ser Ile Thr Asp Leu Val Gln Asn
        110                 115                 120

GCG AGC CCC CGG CTG CTA GAG GGC CAG ATA GAA GTA CAA GAC ATC AAT           914
Ala Ser Pro Arg Leu Leu Glu Gly Gln Ile Glu Val Gln Asp Ile Asn
125                 130                 135                 140

GAC AAC ACA CCC AAC TTC GCC TCA CCA GTC ATC ACT CTG GCC ATC CCT           962
Asp Asn Thr Pro Asn Phe Ala Ser Pro Val Ile Thr Leu Ala Ile Pro
                145                 150                 155

GAG AAC ACC AAC ATC GGC TCA CTC TTC CCC ATC CCG CTG GCT TCA GAC          1010
Glu Asn Thr Asn Ile Gly Ser Leu Phe Pro Ile Pro Leu Ala Ser Asp
            160                 165                 170

CGT GAT GCT GGT CCC AAC GGT GTG GCA TCC TAT GAG CTG CAG GTG GCA          1058
Arg Asp Ala Gly Pro Asn Gly Val Ala Ser Tyr Glu Leu Gln Val Ala
        175                 180                 185

GAG GAC CAG GAG GAG AAG CAA CCA CAG CTC ATT GTG ATG GGC AAC CTG          1106
Glu Asp Gln Glu Glu Lys Gln Pro Gln Leu Ile Val Met Gly Asn Leu
190                 195                 200

GAC CGT GAG CGC TGG GAC TCC TAT GAC CTC ACC ATC AAG GTG CAG GAT          1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG          1202
Gly Gly Ser Pro Pro Arg Ala Thr Ser Ala Leu Leu Arg Val Thr Val
                225                 230                 235

CTT GAC ACC AAT GAC AAC GCC CCC AAG TTT GAG CGG CCC TCC TAT GAG          1250
Leu Asp Thr Asn Asp Asn Ala Pro Lys Phe Glu Arg Pro Ser Tyr Glu
            240                 245                 250

GCC GAA CTA TCT GAG AAT AGC CCC ATA GGC CAC TCG GTC ATC CAG GTG          1298
Ala Glu Leu Ser Glu Asn Ser Pro Ile Gly His Ser Val Ile Gln Val
```

-continued

|  |  |  |  |  |  |  |  |  |  |  |  |  |  |  |  |  |
|---|---|---|---|---|---|---|---|---|---|---|---|---|---|---|---|---|
|  |  |  | 255 |  |  |  |  | 260 |  |  |  |  | 265 |  |  |  |
| AAG | GCC | AAT | GAC | TCA | GAC | CAA | GGT | GCC | AAT | GCA | GAA | ATC | GAA | TAC | ACA | 1346 |
| Lys | Ala | Asn | Asp | Ser | Asp | Gln | Gly | Ala | Asn | Ala | Glu | Ile | Glu | Tyr | Thr |  |
|  |  | 270 |  |  |  | 275 |  |  |  |  | 280 |  |  |  |  |  |
| TTC | CAC | CAG | GCG | CCC | GAA | GTT | GTG | AGG | CGT | CTT | CTT | CGA | CTG | GAC | AGG | 1394 |
| Phe | His | Gln | Ala | Pro | Glu | Val | Val | Arg | Arg | Leu | Leu | Arg | Leu | Asp | Arg |  |
| 285 |  |  |  |  | 290 |  |  |  |  | 295 |  |  |  |  | 300 |  |
| AAC | ACT | GGA | CTT | ATC | ACT | GTT | CAG | GGC | CCG | GTG | GAC | CGT | GAG | GAC | CTA | 1442 |
| Asn | Thr | Gly | Leu | Ile | Thr | Val | Gln | Gly | Pro | Val | Asp | Arg | Glu | Asp | Leu |  |
|  |  |  |  | 305 |  |  |  |  | 310 |  |  |  |  | 315 |  |  |
| AGC | ACC | CTG | CGC | TTC | TCA | GTG | CTT | GCT | AAG | GAC | CGA | GGC | ACC | AAC | CCC | 1490 |
| Ser | Thr | Leu | Arg | Phe | Ser | Val | Leu | Ala | Lys | Asp | Arg | Gly | Thr | Asn | Pro |  |
|  |  |  | 320 |  |  |  |  | 325 |  |  |  |  | 330 |  |  |  |
| AAG | AGT | GCC | CGT | GCC | CAG | GTG | GTT | GTG | ACC | GTG | AAG | GAC | ATG | AAT | GAC | 1538 |
| Lys | Ser | Ala | Arg | Ala | Gln | Val | Val | Val | Thr | Val | Lys | Asp | Met | Asn | Asp |  |
|  |  | 335 |  |  |  |  | 340 |  |  |  |  | 345 |  |  |  |  |
| AAT | GCC | CCC | ACC | ATT | GAG | ATC | CGG | GGC | ATA | GGG | CTA | GTG | ACT | CAT | CAA | 1586 |
| Asn | Ala | Pro | Thr | Ile | Glu | Ile | Arg | Gly | Ile | Gly | Leu | Val | Thr | His | Gln |  |
| 350 |  |  |  |  | 355 |  |  |  |  | 360 |  |  |  |  |  |  |
| GAT | GGG | ATG | GCT | AAC | ATC | TCA | GAG | GAT | GTG | GCA | GAG | GAG | ACA | GCT | GTG | 1634 |
| Asp | Gly | Met | Ala | Asn | Ile | Ser | Glu | Asp | Val | Ala | Glu | Glu | Thr | Ala | Val |  |
| 365 |  |  |  | 370 |  |  |  |  | 375 |  |  |  |  |  | 380 |  |
| GCC | CTG | GTG | CAG | GTG | TCT | GAC | CGA | GAT | GAG | GGA | GAG | AAT | GCA | GCT | GTC | 1682 |
| Ala | Leu | Val | Gln | Val | Ser | Asp | Arg | Asp | Glu | Gly | Glu | Asn | Ala | Ala | Val |  |
|  |  |  |  | 385 |  |  |  |  | 390 |  |  |  |  | 395 |  |  |
| ACC | TGT | GTG | GTG | GCA | GGT | GAT | GTG | CCC | TTC | CAG | CTG | CGC | CAG | GCC | AGT | 1730 |
| Thr | Cys | Val | Val | Ala | Gly | Asp | Val | Pro | Phe | Gln | Leu | Arg | Gln | Ala | Ser |  |
|  |  |  | 400 |  |  |  |  | 405 |  |  |  |  | 410 |  |  |  |
| GAG | ACA | GGC | AGT | GAC | AGC | AAG | AAG | AAG | TAT | TTC | CTG | CAG | ACT | ACC | ACC | 1778 |
| Glu | Thr | Gly | Ser | Asp | Ser | Lys | Lys | Lys | Tyr | Phe | Leu | Gln | Thr | Thr | Thr |  |
|  |  | 415 |  |  |  |  | 420 |  |  |  |  | 425 |  |  |  |  |
| CCG | CTA | GAC | TAC | GAG | AAG | GTC | AAA | GAC | TAC | ACC | ATT | GAG | ATT | GTG | GCT | 1826 |
| Pro | Leu | Asp | Tyr | Glu | Lys | Val | Lys | Asp | Tyr | Thr | Ile | Glu | Ile | Val | Ala |  |
|  | 430 |  |  |  |  | 435 |  |  |  |  | 440 |  |  |  |  |  |
| GTG | GAC | TCT | GGC | AAC | CCC | CCA | CTC | TCC | AGC | ACT | AAC | TCC | CTC | AAG | GTG | 1874 |
| Val | Asp | Ser | Gly | Asn | Pro | Pro | Leu | Ser | Ser | Thr | Asn | Ser | Leu | Lys | Val |  |
| 445 |  |  |  |  | 450 |  |  |  |  | 455 |  |  |  |  | 460 |  |
| CAG | GTG | GTG | GAC | GTC | AAT | GAC | AAC | GCA | CCT | GTC | TTC | ACT | CAG | AGT | GTC | 1922 |
| Gln | Val | Val | Asp | Val | Asn | Asp | Asn | Ala | Pro | Val | Phe | Thr | Gln | Ser | Val |  |
|  |  |  |  | 465 |  |  |  |  | 470 |  |  |  |  | 475 |  |  |
| ACT | GAG | GTC | GCC | TTC | CCG | GAA | AAC | AAC | AAG | CCT | GGT | GAA | GTG | ATT | GCT | 1970 |
| Thr | Glu | Val | Ala | Phe | Pro | Glu | Asn | Asn | Lys | Pro | Gly | Glu | Val | Ile | Ala |  |
|  |  |  | 480 |  |  |  |  | 485 |  |  |  |  | 490 |  |  |  |
| GAG | ATC | ACT | GCC | AGT | GAT | GCT | GAC | TCT | GGC | TCT | AAT | GCT | GAG | CTG | GTT | 2018 |
| Glu | Ile | Thr | Ala | Ser | Asp | Ala | Asp | Ser | Gly | Ser | Asn | Ala | Glu | Leu | Val |  |
|  |  | 495 |  |  |  |  | 500 |  |  |  |  | 505 |  |  |  |  |
| TAC | TCT | CTG | GAG | CCT | GAG | CCG | GCT | GCT | AAG | GGC | CTC | TTC | ACC | ATC | TCA | 2066 |
| Tyr | Ser | Leu | Glu | Pro | Glu | Pro | Ala | Ala | Lys | Gly | Leu | Phe | Thr | Ile | Ser |  |
| 510 |  |  |  |  | 515 |  |  |  |  | 520 |  |  |  |  |  |  |
| CCC | GAG | ACT | GGA | GAG | ATC | CAG | GTG | AAG | ACA | TCT | CTG | GAT | CGG | GAA | CAG | 2114 |
| Pro | Glu | Thr | Gly | Glu | Ile | Gln | Val | Lys | Thr | Ser | Leu | Asp | Arg | Glu | Gln |  |
| 525 |  |  |  |  | 530 |  |  |  |  | 535 |  |  |  |  | 540 |  |
| CGG | GAG | AGC | TAT | GAG | TTG | AAG | GTG | GTG | GCA | GCT | GAC | CGG | GGC | AGT | CCT | 2162 |
| Arg | Glu | Ser | Tyr | Glu | Leu | Lys | Val | Val | Ala | Ala | Asp | Arg | Gly | Ser | Pro |  |
|  |  |  |  | 545 |  |  |  |  | 550 |  |  |  |  | 555 |  |  |
| AGC | CTC | CAG | GGC | ACA | GCC | ACT | GTC | CTT | GTC | AAT | GTG | CTG | GAC | TGC | AAT | 2210 |
| Ser | Leu | Gln | Gly | Thr | Ala | Thr | Val | Leu | Val | Asn | Val | Leu | Asp | Cys | Asn |  |
|  |  |  | 560 |  |  |  |  | 565 |  |  |  |  | 570 |  |  |  |
| GAC | AAT | GAC | CCC | AAA | TTT | ATG | CTG | AGT | GGC | TAC | AAC | TTC | TCA | GTG | ATG | 2258 |
| Asp | Asn | Asp | Pro | Lys | Phe | Met | Leu | Ser | Gly | Tyr | Asn | Phe | Ser | Val | Met |  |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 575 |     |     |     | 580 |     |     |     | 585 |     |     |     |     |      |
| GAG | AAC | ATG | CCA | GCA | CTG | AGT | CCA | GTG | GGC | ATG | GTG | ACT | GTC | ATT | GAT | 2306 |
| Glu | Asn | Met | Pro | Ala | Leu | Ser | Pro | Val | Gly | Met | Val | Thr | Val | Ile | Asp |      |
|     | 590 |     |     |     |     | 595 |     |     |     | 600 |     |     |     |     |     |      |
| GGA | GAC | AAG | GGG | GAG | AAT | GCC | CAG | GTG | CAG | CTC | TCA | GTG | GAG | CAG | GAC | 2354 |
| Gly | Asp | Lys | Gly | Glu | Asn | Ala | Gln | Val | Gln | Leu | Ser | Val | Glu | Gln | Asp |      |
| 605 |     |     |     |     | 610 |     |     |     | 615 |     |     |     |     |     | 620 |      |
| AAC | GGT | GAC | TTT | GTT | ATC | CAG | AAT | GGC | ACA | GGC | ACC | ATC | CTA | TCC | AGC | 2402 |
| Asn | Gly | Asp | Phe | Val | Ile | Gln | Asn | Gly | Thr | Gly | Thr | Ile | Leu | Ser | Ser |      |
|     |     |     |     | 625 |     |     |     |     | 630 |     |     |     |     | 635 |     |      |
| CTG | AGC | TTT | GAT | CGA | GAG | CAA | CAA | AGC | ACC | TAC | ACC | TTC | CAG | CTG | AAG | 2450 |
| Leu | Ser | Phe | Asp | Arg | Glu | Gln | Gln | Ser | Thr | Tyr | Thr | Phe | Gln | Leu | Lys |      |
|     |     |     | 640 |     |     |     |     | 645 |     |     |     |     | 650 |     |     |      |
| GCA | GTG | GAT | GGT | GGC | GTC | CCA | CCT | CGC | TCA | GCT | TAC | GTT | GGT | GTC | ACC | 2498 |
| Ala | Val | Asp | Gly | Gly | Val | Pro | Pro | Arg | Ser | Ala | Tyr | Val | Gly | Val | Thr |      |
|     |     | 655 |     |     |     |     | 660 |     |     |     |     | 665 |     |     |     |      |
| ATC | AAT | GTG | CTG | GAC | GAG | AAT | GAC | AAC | GCA | CCC | TAT | ATC | ACT | GCC | CCT | 2546 |
| Ile | Asn | Val | Leu | Asp | Glu | Asn | Asp | Asn | Ala | Pro | Tyr | Ile | Thr | Ala | Pro |      |
|     | 670 |     |     |     |     | 675 |     |     |     |     | 680 |     |     |     |     |      |
| TCT | AAC | ACC | TCT | CAC | AAG | CTG | CTG | ACC | CCC | CAG | ACA | CGT | CTT | GGT | GAG | 2594 |
| Ser | Asn | Thr | Ser | His | Lys | Leu | Leu | Thr | Pro | Gln | Thr | Arg | Leu | Gly | Glu |      |
| 685 |     |     |     |     | 690 |     |     |     |     | 695 |     |     |     |     | 700 |      |
| ACG | GTC | AGC | CAG | GTG | GCA | GCC | GAG | GAC | TTT | GAC | TCT | GGT | GTC | AAT | GCC | 2642 |
| Thr | Val | Ser | Gln | Val | Ala | Ala | Glu | Asp | Phe | Asp | Ser | Gly | Val | Asn | Ala |      |
|     |     |     |     | 705 |     |     |     |     | 710 |     |     |     |     | 715 |     |      |
| GAG | CTG | ATC | TAC | AGC | ATT | GCA | GGT | GGC | AAC | CCT | TAT | GGA | CTC | TTC | CAG | 2690 |
| Glu | Leu | Ile | Tyr | Ser | Ile | Ala | Gly | Gly | Asn | Pro | Tyr | Gly | Leu | Phe | Gln |      |
|     |     |     | 720 |     |     |     |     | 725 |     |     |     |     | 730 |     |     |      |
| ATT | GGG | TCA | CAT | TCA | GGT | GCC | ATC | ACC | CTG | GAG | AAG | GAG | ATT | GAG | CGG | 2738 |
| Ile | Gly | Ser | His | Ser | Gly | Ala | Ile | Thr | Leu | Glu | Lys | Glu | Ile | Glu | Arg |      |
|     |     | 735 |     |     |     |     | 740 |     |     |     |     | 745 |     |     |     |      |
| CGC | CAC | CAT | GGG | CTA | CAC | CGC | CTG | GTG | GTG | AAG | GTC | AGT | GAC | CGC | GGC | 2786 |
| Arg | His | His | Gly | Leu | His | Arg | Leu | Val | Val | Lys | Val | Ser | Asp | Arg | Gly |      |
|     | 750 |     |     |     |     | 755 |     |     |     |     | 760 |     |     |     |     |      |
| AAG | CCC | CCA | CGC | TAT | GGC | ACA | GCC | TTG | GTC | CAT | CTT | TAT | GTC | AAT | GAG | 2834 |
| Lys | Pro | Pro | Arg | Tyr | Gly | Thr | Ala | Leu | Val | His | Leu | Tyr | Val | Asn | Glu |      |
| 765 |     |     |     |     | 770 |     |     |     |     | 775 |     |     |     |     | 780 |      |
| ACT | CTG | GCC | AAC | CGC | ACG | CTG | CTG | GAG | ACC | CTC | CTG | GGC | CAC | AGC | CTG | 2882 |
| Thr | Leu | Ala | Asn | Arg | Thr | Leu | Leu | Glu | Thr | Leu | Leu | Gly | His | Ser | Leu |      |
|     |     |     |     | 785 |     |     |     |     | 790 |     |     |     |     | 795 |     |      |
| GAC | ACG | CCG | CTG | GAT | ATT | GAC | ATT | GCT | GGG | GAT | CCA | GAA | TAT | GAG | CGC | 2930 |
| Asp | Thr | Pro | Leu | Asp | Ile | Asp | Ile | Ala | Gly | Asp | Pro | Glu | Tyr | Glu | Arg |      |
|     |     |     | 800 |     |     |     |     | 805 |     |     |     |     | 810 |     |     |      |
| TCC | AAG | CAG | CGT | GGC | AAC | ATT | CTC | TTT | GGT | GTG | GTG | GCT | GGT | GTG | GTG | 2978 |
| Ser | Lys | Gln | Arg | Gly | Asn | Ile | Leu | Phe | Gly | Val | Val | Ala | Gly | Val | Val |      |
|     |     | 815 |     |     |     |     | 820 |     |     |     |     | 825 |     |     |     |      |
| GCC | GTG | GCC | TTG | CTC | ATC | GCC | CTG | GCG | GTT | CTT | GTG | CGC | TAC | TGC | AGA | 3026 |
| Ala | Val | Ala | Leu | Leu | Ile | Ala | Leu | Ala | Val | Leu | Val | Arg | Tyr | Cys | Arg |      |
|     | 830 |     |     |     |     | 835 |     |     |     |     | 840 |     |     |     |     |      |
| CAG | CGG | GAG | GCC | AAA | AGT | GGT | TAC | CAG | GCT | GGT | AAG | AAG | GAG | ACC | AAG | 3074 |
| Gln | Arg | Glu | Ala | Lys | Ser | Gly | Tyr | Gln | Ala | Gly | Lys | Lys | Glu | Thr | Lys |      |
| 845 |     |     |     |     | 850 |     |     |     |     | 855 |     |     |     |     | 860 |      |
| GAC | CTG | TAT | GCC | CCC | AAG | CCC | AGT | GGC | AAG | GCC | TCC | AAG | GGA | AAC | AAA | 3122 |
| Asp | Leu | Tyr | Ala | Pro | Lys | Pro | Ser | Gly | Lys | Ala | Ser | Lys | Gly | Asn | Lys |      |
|     |     |     |     | 865 |     |     |     |     | 870 |     |     |     |     | 875 |     |      |
| AGC | AAA | GGC | AAG | AAG | AGC | AAG | TCC | CCA | AAG | CCC | GTG | AAG | CCA | GTG | GAG | 3170 |
| Ser | Lys | Gly | Lys | Lys | Ser | Lys | Ser | Pro | Lys | Pro | Val | Lys | Pro | Val | Glu |      |
|     |     |     | 880 |     |     |     |     | 885 |     |     |     |     | 890 |     |     |      |
| GAC | GAG | GAT | GAG | GCC | GGG | CTG | CAG | AAG | TCC | CTC | AAG | TTC | AAC | CTG | ATG | 3218 |
| Asp | Glu | Asp | Glu | Ala | Gly | Leu | Gln | Lys | Ser | Leu | Lys | Phe | Asn | Leu | Met |      |

|     |     |     |     |     | 895 |     |     |     | 900 |     |     |     |     | 905 |     |      |
|-----|-----|-----|-----|-----|-----|-----|-----|-----|-----|-----|-----|-----|-----|-----|-----|------|
| AGC | GAT | GCC | CCT | GGG | GAC | AGT | CCC | CGC | ATC | CAC | CTG | CCC | CTC | AAC | TAC | 3266 |
| Ser | Asp | Ala | Pro | Gly | Asp | Ser | Pro | Arg | Ile | His | Leu | Pro | Leu | Asn | Tyr |      |
| Ser | Asp | Ala | 910 | Gly | Asp | Ser | Pro | Arg | 915 | His | Leu | Pro | 920 | Asn | Tyr |      |

CCA CCA GGC AGC CCT GAC CTG GGC CGC CAC TAT CGC TCT AAC TCC CCA  3314
Pro Pro Gly Ser Pro Asp Leu Gly Arg His Tyr Arg Ser Asn Ser Pro
925             930                 935                     940

CTG CCT TCC ATC CAG CTG CAG CCC CAG TCA CCC TCA GCC TCC AAG AAG  3362
Leu Pro Ser Ile Gln Leu Gln Pro Gln Ser Pro Ser Ala Ser Lys Lys
                945                 950                 955

CAC CAG GTG GTA CAG GAC CTG CCA CCT GCA AAC ACA TTC GTG GGC ACC  3410
His Gln Val Val Gln Asp Leu Pro Pro Ala Asn Thr Phe Val Gly Thr
            960                 965                 970

GGG GAC ACC ACG TCC ACG GGC TCT GAG CAG TAC TCC GAC TAC AGC TAC  3458
Gly Asp Thr Thr Ser Thr Gly Ser Glu Gln Tyr Ser Asp Tyr Ser Tyr
        975                 980                 985

CGC ACC AAC CCC CCC AAA TAC CCC AGC AAG CAG TTA CCT CAC CGC CGC  3506
Arg Thr Asn Pro Pro Lys Tyr Pro Ser Lys Gln Leu Pro His Arg Arg
        990                 995                 1000

GTC ACC TTC TCG GCC ACC AGC CAG GCC CAG GAG CTG CAG GAC CCA TCC  3554
Val Thr Phe Ser Ala Thr Ser Gln Ala Gln Glu Leu Gln Asp Pro Ser
1005                1010                1015                1020

CAG CAC AGT TAC TAT GAC AGT GGC CTG GAG GAG TCT GAG ACG CCG TCC  3602
Gln His Ser Tyr Tyr Asp Ser Gly Leu Glu Glu Ser Glu Thr Pro Ser
                1025                1030                1035

AGC AAG TCA TCC TCA GGG CCT CGA CTC GGT CCC CTG GCC CTG CCT GAG  3650
Ser Lys Ser Ser Ser Gly Pro Arg Leu Gly Pro Leu Ala Leu Pro Glu
            1040                1045                1050

GAT CAC TAT GAG CGC ACC ACC CCT GAT GGC AGC ATA GGA GAG ATG GAG  3698
Asp His Tyr Glu Arg Thr Thr Pro Asp Gly Ser Ile Gly Glu Met Glu
        1055                1060                1065

CAC CCC GAG AAT GAC CTT CGC CCT TTG CCT GAT GTC GCC ATG ACA GGC  3746
His Pro Glu Asn Asp Leu Arg Pro Leu Pro Asp Val Ala Met Thr Gly
        1070                1075                1080

ACA TGT ACC CGG GAG TGC AGT GAG TTT GGC CAC TCT GAC ACA TGC TGG  3794
Thr Cys Thr Arg Glu Cys Ser Glu Phe Gly His Ser Asp Thr Cys Trp
1085                1090                1095                1100

ATG CCT GGC CAG TCA TCT CCC AGC CGC CGG ACC AAG AGC AGC GCC CTC  3842
Met Pro Gly Gln Ser Ser Pro Ser Arg Arg Thr Lys Ser Ser Ala Leu
                1105                1110                1115

AAA CTC TCC ACC TTC ATG CCT TAC CAG GAC CGA GGA GGG CAG GAG CCT  3890
Lys Leu Ser Thr Phe Met Pro Tyr Gln Asp Arg Gly Gly Gln Glu Pro
            1120                1125                1130

GCG GGC GCC GGC AGC CCC AGC CCC CCG GAA GAC CGG AAC ACC AAA ACG  3938
Ala Gly Ala Gly Ser Pro Ser Pro Pro Glu Asp Arg Asn Thr Lys Thr
        1135                1140                1145

GCC CCC GTG CGC CTC CTG CCC TCC TAC AGT GCC TTC TCC CAC AGT AGC  3986
Ala Pro Val Arg Leu Leu Pro Ser Tyr Ser Ala Phe Ser His Ser Ser
1150                1155                1160

CAT GAT TCC TGC AAG GAC TCG GCC ACC TTG GAG GAA ATC CCC CTG ACC  4034
His Asp Ser Cys Lys Asp Ser Ala Thr Leu Glu Glu Ile Pro Leu Thr
1165                1170                1175                1180

CAG ACC TCG GAC TTC CCA CCC GCA GCC ACA CCG GCA TCT GCC CAG ACG  4082
Gln Thr Ser Asp Phe Pro Pro Ala Ala Thr Pro Ala Ser Ala Gln Thr
                1185                1190                1195

GCC AAG CGC GAG ATC TAC CTG TGAGCCCCT ACTGGCCGGC CCCCCTCCCC  4133
Ala Lys Arg Glu Ile Tyr Leu
                1200

CAGCGCCGGC CAGCTCCCAA ATGCCCATTC CAGGGCCTCA CTCTCCACCC CTTCAGCGTG  4193

| | | | | |
|---|---|---|---|---|
| GACTTCCTGC | CAGGGCCCAA | GTGGGGGTAT | CACTGACCTC | ATGACCACGC | TGGCCCTTCT | 4253 |
| CCCATGCAGG | GTCCAGGTCC | TCTCCCCTCA | TTTCCATCTC | CCAGCCCAGG | GGCCCCTTCC | 4313 |
| CCTTTATGGG | GCTTCCCCCA | GCTGATGCCC | AAGAGGGCTC | CTCTGCAATG | ACTGGGCTCC | 4373 |
| TTCCCTTGAC | TTCCAGGGAG | CACCCCCTCG | ATTTGGGCAG | ATGGTGGAGT | CAAGGGTGGG | 4433 |
| CAGCGTACTT | CTAACTCATT | GTTTCCCTCA | TGGCCGACCA | GGGCGGGGAT | AGCATGCCCA | 4493 |
| ATTTTAGCCC | TGAAGCAGGG | CTGAACTGGG | GAGCCCCTTT | CCCTGGGAGC | TCCAGAGGA | 4553 |
| AACTCTTGAC | CACCAGTGGC | TCCCTGAAGG | GCTTTTGTTA | CCAAAGGTGG | GGTAGGGACG | 4613 |
| GGGGTGGGAG | TGGAGCGGAG | GCCTTGTTTT | CCCGTGG | | | 4650 |

(2) INFORMATION FOR SEQ ID NO:103:

(i) SEQUENCE CHARACTERISTICS:
 (A) LENGTH: 1203 amino acids
 (B) TYPE: amino acid
 (D) TOPOLOGY: linear (ii) MOLECULE TYPE: protein (xi) SEQUENCE DESCRIPTION: SEQ ID NO:103:

```
Met Glu Pro Leu Arg His Ser Pro Gly Pro Gly Gly Gln Arg Leu Leu
 1               5                  10                  15

Leu Pro Ser Met Leu Ala Leu Leu Leu Leu Ala Pro Ser Pro
                20                  25                  30

Gly His Ala Thr Arg Val Val Tyr Lys Val Pro Glu Glu Gln Pro Pro
            35                  40                  45

Asn Thr Leu Ile Gly Ser Leu Ala Ala Asp Tyr Gly Phe Pro Asp Val
    50                  55                  60

Gly His Leu Tyr Lys Leu Glu Val Gly Ala Pro Tyr Leu Arg Val Asp
65                  70                  75                  80

Gly Lys Thr Gly Asp Ile Phe Thr Thr Glu Thr Ser Ile Asp Arg Glu
                85                  90                  95

Gly Leu Arg Glu Cys Gln Asn Gln Leu Pro Gly Asp Pro Cys Ile Leu
            100                 105                 110

Glu Phe Glu Val Ser Ile Thr Asp Leu Val Gln Asn Ala Ser Pro Arg
        115                 120                 125

Leu Leu Glu Gly Gln Ile Glu Val Gln Asp Ile Asn Asp Asn Thr Pro
    130                 135                 140

Asn Phe Ala Ser Pro Val Ile Thr Leu Ala Ile Pro Glu Asn Thr Asn
145                 150                 155                 160

Ile Gly Ser Leu Phe Pro Ile Pro Leu Ala Ser Asp Arg Asp Ala Gly
                165                 170                 175

Pro Asn Gly Val Ala Ser Tyr Glu Leu Gln Val Ala Glu Asp Gln Glu
            180                 185                 190

Glu Lys Gln Pro Gln Leu Ile Val Met Gly Asn Leu Asp Arg Glu Arg
        195                 200                 205

Trp Asp Ser Tyr Asp Leu Thr Ile Lys Val Gln Asp Gly Gly Ser Pro
    210                 215                 220

Pro Arg Ala Thr Ser Ala Leu Leu Arg Val Thr Val Leu Asp Thr Asn
225                 230                 235                 240

Asp Asn Ala Pro Lys Phe Glu Arg Pro Ser Tyr Glu Ala Glu Leu Ser
                245                 250                 255

Glu Asn Ser Pro Ile Gly His Ser Val Ile Gln Val Lys Ala Asn Asp
            260                 265                 270

Ser Asp Gln Gly Ala Asn Ala Glu Ile Glu Tyr Thr Phe His Gln Ala
```

```
              275                    280                      285
Pro  Glu  Val  Val  Arg  Arg  Leu  Leu  Arg  Leu  Asp  Arg  Asn  Thr  Gly  Leu
          290                    295                      300
Ile  Thr  Val  Gln  Gly  Pro  Val  Asp  Arg  Glu  Asp  Leu  Ser  Thr  Leu  Arg
305                 310                      315                           320
Phe  Ser  Val  Leu  Ala  Lys  Asp  Arg  Gly  Thr  Asn  Pro  Lys  Ser  Ala  Arg
                    325                      330                      335
Ala  Gln  Val  Val  Val  Thr  Val  Lys  Asp  Met  Asn  Asp  Asn  Ala  Pro  Thr
                    340                      345                      350
Ile  Glu  Ile  Arg  Gly  Ile  Gly  Leu  Val  Thr  His  Gln  Asp  Gly  Met  Ala
                    355                      360                      365
Asn  Ile  Ser  Glu  Asp  Val  Ala  Glu  Glu  Thr  Ala  Val  Ala  Leu  Val  Gln
          370                      375                      380
Val  Ser  Asp  Arg  Asp  Glu  Gly  Glu  Asn  Ala  Ala  Val  Thr  Cys  Val  Val
385                           390                      395                400
Ala  Gly  Asp  Val  Pro  Phe  Gln  Leu  Arg  Gln  Ala  Ser  Glu  Thr  Gly  Ser
                    405                      410                      415
Asp  Ser  Lys  Lys  Lys  Tyr  Phe  Leu  Gln  Thr  Thr  Thr  Pro  Leu  Asp  Tyr
                    420                      425                      430
Glu  Lys  Val  Lys  Asp  Tyr  Thr  Ile  Glu  Ile  Val  Ala  Val  Asp  Ser  Gly
          435                      440                      445
Asn  Pro  Pro  Leu  Ser  Ser  Thr  Asn  Ser  Leu  Lys  Val  Gln  Val  Val  Asp
     450                      455                      460
Val  Asn  Asp  Asn  Ala  Pro  Val  Phe  Thr  Gln  Ser  Val  Thr  Glu  Val  Ala
465                      470                      475                      480
Phe  Pro  Glu  Asn  Asn  Lys  Pro  Gly  Glu  Val  Ile  Ala  Glu  Ile  Thr  Ala
                         485                      490                      495
Ser  Asp  Ala  Asp  Ser  Gly  Ser  Asn  Ala  Glu  Leu  Val  Tyr  Ser  Leu  Glu
                    500                      505                      510
Pro  Glu  Pro  Ala  Ala  Lys  Gly  Leu  Phe  Thr  Ile  Ser  Pro  Glu  Thr  Gly
               515                      520                      525
Glu  Ile  Gln  Val  Lys  Thr  Ser  Leu  Asp  Arg  Glu  Gln  Arg  Glu  Ser  Tyr
     530                         535                      540
Glu  Leu  Lys  Val  Val  Ala  Ala  Asp  Arg  Gly  Ser  Pro  Ser  Leu  Gln  Gly
545                      550                      555                      560
Thr  Ala  Thr  Val  Leu  Val  Asn  Val  Leu  Asp  Cys  Asn  Asp  Asn  Asp  Pro
                    565                      570                      575
Lys  Phe  Met  Leu  Ser  Gly  Tyr  Asn  Phe  Ser  Val  Met  Glu  Asn  Met  Pro
                    580                      585                      590
Ala  Leu  Ser  Pro  Val  Gly  Met  Val  Thr  Val  Ile  Asp  Gly  Asp  Lys  Gly
               595                      600                      605
Glu  Asn  Ala  Gln  Val  Gln  Leu  Ser  Val  Glu  Gln  Asp  Asn  Gly  Asp  Phe
          610                      615                      620
Val  Ile  Gln  Asn  Gly  Thr  Gly  Thr  Ile  Leu  Ser  Ser  Leu  Ser  Phe  Asp
625                      630                      635                      640
Arg  Glu  Gln  Gln  Ser  Thr  Tyr  Thr  Phe  Gln  Leu  Lys  Ala  Val  Asp  Gly
                    645                      650                      655
Gly  Val  Pro  Pro  Arg  Ser  Ala  Tyr  Val  Gly  Val  Thr  Ile  Asn  Val  Leu
               660                      665                      670
Asp  Glu  Asn  Asp  Asn  Ala  Pro  Tyr  Ile  Thr  Ala  Pro  Ser  Asn  Thr  Ser
          675                      680                      685
His  Lys  Leu  Leu  Thr  Pro  Gln  Thr  Arg  Leu  Gly  Glu  Thr  Val  Ser  Gln
     690                      695                      700
```

```
Val Ala Ala Glu Asp Phe Asp Ser Gly Val Asn Ala Glu Leu Ile Tyr
705                 710                 715                 720

Ser Ile Ala Gly Gly Asn Pro Tyr Gly Leu Phe Gln Ile Gly Ser His
                725                 730                 735

Ser Gly Ala Ile Thr Leu Glu Lys Glu Ile Glu Arg Arg His His Gly
            740                 745                 750

Leu His Arg Leu Val Val Lys Val Ser Asp Arg Gly Lys Pro Pro Arg
        755                 760                 765

Tyr Gly Thr Ala Leu Val His Leu Tyr Val Asn Glu Thr Leu Ala Asn
    770                 775                 780

Arg Thr Leu Leu Glu Thr Leu Leu Gly His Ser Leu Asp Thr Pro Leu
785                 790                 795                 800

Asp Ile Asp Ile Ala Gly Asp Pro Glu Tyr Glu Arg Ser Lys Gln Arg
                805                 810                 815

Gly Asn Ile Leu Phe Gly Val Val Ala Gly Val Val Ala Val Ala Leu
            820                 825                 830

Leu Ile Ala Leu Ala Val Leu Val Arg Tyr Cys Arg Gln Arg Glu Ala
        835                 840                 845

Lys Ser Gly Tyr Gln Ala Gly Lys Lys Glu Thr Lys Asp Leu Tyr Ala
    850                 855                 860

Pro Lys Pro Ser Gly Lys Ala Ser Lys Gly Asn Lys Ser Lys Gly Lys
865                 870                 875                 880

Lys Ser Lys Ser Pro Lys Pro Val Lys Pro Val Glu Asp Glu Asp Glu
                885                 890                 895

Ala Gly Leu Gln Lys Ser Leu Lys Phe Asn Leu Met Ser Asp Ala Pro
            900                 905                 910

Gly Asp Ser Pro Arg Ile His Leu Pro Leu Asn Tyr Pro Pro Gly Ser
        915                 920                 925

Pro Asp Leu Gly Arg His Tyr Arg Ser Asn Ser Pro Leu Pro Ser Ile
    930                 935                 940

Gln Leu Gln Pro Gln Ser Pro Ser Ala Ser Lys Lys His Gln Val Val
945                 950                 955                 960

Gln Asp Leu Pro Pro Ala Asn Thr Phe Val Gly Thr Gly Asp Thr Thr
                965                 970                 975

Ser Thr Gly Ser Glu Gln Tyr Ser Asp Tyr Ser Tyr Arg Thr Asn Pro
            980                 985                 990

Pro Lys Tyr Pro Ser Lys Gln Leu Pro His Arg Arg Val Thr Phe Ser
        995                 1000                1005

Ala Thr Ser Gln Ala Gln Glu Leu Gln Asp Pro Ser Gln His Ser Tyr
    1010                1015                1020

Tyr Asp Ser Gly Leu Glu Glu Ser Glu Thr Pro Ser Ser Lys Ser Ser
1025                1030                1035                1040

Ser Gly Pro Arg Leu Gly Pro Leu Ala Leu Pro Glu Asp His Tyr Glu
                1045                1050                1055

Arg Thr Thr Pro Asp Gly Ser Ile Gly Glu Met Glu His Pro Glu Asn
            1060                1065                1070

Asp Leu Arg Pro Leu Pro Asp Val Ala Met Thr Gly Thr Cys Thr Arg
        1075                1080                1085

Glu Cys Ser Glu Phe Gly His Ser Asp Thr Cys Trp Met Pro Gly Gln
    1090                1095                1100

Ser Ser Pro Ser Arg Arg Thr Lys Ser Ser Ala Leu Lys Leu Ser Thr
1105                1110                1115                1120

Phe Met Pro Tyr Gln Asp Arg Gly Gly Gln Glu Pro Ala Gly Ala Gly
                1125                1130                1135
```

-continued

```
Ser  Pro  Ser  Pro  Pro  Glu  Asp  Arg  Asn  Thr  Lys  Thr  Ala  Pro  Val  Arg
          1140                    1145                    1150

Leu  Leu  Pro  Ser  Tyr  Ser  Ala  Phe  Ser  His  Ser  Ser  His  Asp  Ser  Cys
          1155                    1160                    1165

Lys  Asp  Ser  Ala  Thr  Leu  Glu  Glu  Ile  Pro  Leu  Thr  Gln  Thr  Ser  Asp
     1170                    1175                    1180

Phe  Pro  Pro  Ala  Ala  Thr  Pro  Ala  Ser  Ala  Gln  Thr  Ala  Lys  Arg  Glu
1185                    1190                    1195                    1200

Ile  Tyr  Leu
```

( 2 ) INFORMATION FOR SEQ ID NO:104:

( i ) SEQUENCE CHARACTERISTICS:
    ( A ) LENGTH: 2789 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 115..2622

( x i ) SEQUENCE DESCRIPTION: SEQ ID NO:104:

```
CGAAAGCCAT GTCGGACTCG TCGCCCAGCG CCCAAGCGCT AACCCGCTGA AAGTTTCTCA        60

GCGAAATCTC AGGGACGATC TGGACCCCGC TGAGAGGAAC TGCTTTTGAG TGAG ATG        117
                                                              Met
                                                               1

GTC  CCA  GAG  GCC  TGG  AGG  AGC  GGA  CTG  GTA  AGC  ACC  GGG  AGG  GTA  GTG    165
Val  Pro  Glu  Ala  Trp  Arg  Ser  Gly  Leu  Val  Ser  Thr  Gly  Arg  Val  Val
                    5                    10                        15

GGA  GTT  TTG  CTT  CTG  CTT  GGT  GCC  TTG  AAC  AAG  GCT  TCC  ACG  GTC  ATT    213
Gly  Val  Leu  Leu  Leu  Leu  Gly  Ala  Leu  Asn  Lys  Ala  Ser  Thr  Val  Ile
          20                        25                        30

CAC  TAT  GAG  ATC  CCG  GAG  GAA  AGA  GAG  AAG  GGT  TTC  GCT  GTG  GGC  AAC    261
His  Tyr  Glu  Ile  Pro  Glu  Glu  Arg  Glu  Lys  Gly  Phe  Ala  Val  Gly  Asn
     35                        40                        45

GTG  GTC  GCG  AAC  CTT  GGT  TTG  GAT  CTC  GGT  AGC  CTC  TCA  GCC  CGC  AGG    309
Val  Val  Ala  Asn  Leu  Gly  Leu  Asp  Leu  Gly  Ser  Leu  Ser  Ala  Arg  Arg
50                        55                        60                        65

TTC  CCG  GTG  GTG  TCT  GGA  GCT  AGC  CGA  AGA  TTC  TTT  GAG  GTG  AAC  CGG    357
Phe  Pro  Val  Val  Ser  Gly  Ala  Ser  Arg  Arg  Phe  Phe  Glu  Val  Asn  Arg
                    70                        75                        80

GAG  ACC  GGA  GAG  ATG  TTT  GTG  AAC  GAC  CGT  CTG  GAT  CGA  GAG  GAG  CTG    405
Glu  Thr  Gly  Glu  Met  Phe  Val  Asn  Asp  Arg  Leu  Asp  Arg  Glu  Glu  Leu
                    85                        90                        95

TGT  GGG  ACA  CTG  CCC  TCT  TGC  ACT  GTA  ACT  CTG  GAG  TTG  GTA  GTG  GAG    453
Cys  Gly  Thr  Leu  Pro  Ser  Cys  Thr  Val  Thr  Leu  Glu  Leu  Val  Val  Glu
          100                        105                        110

AAC  CCG  CTG  GAG  CTG  TTC  AGC  GTG  GAA  GTG  GTG  ATC  CAG  GAC  ATC  AAC    501
Asn  Pro  Leu  Glu  Leu  Phe  Ser  Val  Glu  Val  Val  Ile  Gln  Asp  Ile  Asn
     115                        120                        125

GAC  AAC  AAT  CCT  GCT  TTC  CCT  ACC  CAG  GAA  ATG  AAA  TTG  GAG  ATT  AGC    549
Asp  Asn  Asn  Pro  Ala  Phe  Pro  Thr  Gln  Glu  Met  Lys  Leu  Glu  Ile  Ser
130                        135                        140                        145

GAG  GCC  GTG  GCT  CCG  GGG  ACG  CGC  TTT  CCG  CTC  GAG  AGC  GCG  CAC  GAT    597
Glu  Ala  Val  Ala  Pro  Gly  Thr  Arg  Phe  Pro  Leu  Glu  Ser  Ala  His  Asp
                    150                        155                        160

CCC  GAT  CTG  GGA  AGC  AAC  TCT  TTA  CAA  ACC  TAT  GAG  CTG  AGC  CGA  AAT    645
Pro  Asp  Leu  Gly  Ser  Asn  Ser  Leu  Gln  Thr  Tyr  Glu  Leu  Ser  Arg  Asn
```

|     |     |     |     |     | 165 |     |     |     |     | 170 |     |     |     |     | 175 |     |      |
|-----|-----|-----|-----|-----|-----|-----|-----|-----|-----|-----|-----|-----|-----|-----|-----|-----|------|
| GAA | TAC | TTT | GCG | CTT | CGC | GTG | CAG | ACG | CGG | GAG | GAC | AGC | ACC | AAG | TAC |     | 693  |
| Glu | Tyr | Phe | Ala | Leu | Arg | Val | Gln | Thr | Arg | Glu | Asp | Ser | Thr | Lys | Tyr |     |      |
|     |     | 180 |     |     |     |     | 185 |     |     |     |     | 190 |     |     |     |     |      |

| GCG | GAG | CTG | GTG | TTG | GAG | CGC | GCC | CTG | GAC | CGA | GAA | CGG | GAG | CCT | AGT | 741 |
|-----|-----|-----|-----|-----|-----|-----|-----|-----|-----|-----|-----|-----|-----|-----|-----|-----|
| Ala | Glu | Leu | Val | Leu | Glu | Arg | Ala | Leu | Asp | Arg | Glu | Arg | Glu | Pro | Ser |     |
| 195 |     |     |     |     | 200 |     |     |     |     | 205 |     |     |     |     |     |     |

| CTC | CAG | TTA | GTG | CTG | ACG | GCG | TTG | GAC | GGA | GGG | ACC | CCA | GCT | CTC | TCC | 789 |
|-----|-----|-----|-----|-----|-----|-----|-----|-----|-----|-----|-----|-----|-----|-----|-----|-----|
| Leu | Gln | Leu | Val | Leu | Thr | Ala | Leu | Asp | Gly | Gly | Thr | Pro | Ala | Leu | Ser |     |
| 210 |     |     |     |     | 215 |     |     |     |     | 220 |     |     |     |     | 225 |     |

| GCC | AGC | CTG | CCT | ATT | CAC | ATC | AAG | GTG | CTG | GAC | GCG | AAT | GAC | AAT | GCG | 837 |
|-----|-----|-----|-----|-----|-----|-----|-----|-----|-----|-----|-----|-----|-----|-----|-----|-----|
| Ala | Ser | Leu | Pro | Ile | His | Ile | Lys | Val | Leu | Asp | Ala | Asn | Asp | Asn | Ala |     |
|     |     |     |     | 230 |     |     |     |     | 235 |     |     |     |     | 240 |     |     |

| CCT | GTC | TTC | AAC | CAG | TCC | TTG | TAC | CGG | GCG | CGC | GTT | CCT | GGA | GGA | TGC | 885 |
|-----|-----|-----|-----|-----|-----|-----|-----|-----|-----|-----|-----|-----|-----|-----|-----|-----|
| Pro | Val | Phe | Asn | Gln | Ser | Leu | Tyr | Arg | Ala | Arg | Val | Pro | Gly | Gly | Cys |     |
|     |     |     | 245 |     |     |     |     | 250 |     |     |     |     | 255 |     |     |     |

| ACC | TCC | GGC | ACG | CGC | GTG | GTA | CAA | GTC | CTT | GCA | ACG | GAT | CTG | GAT | GAA | 933 |
|-----|-----|-----|-----|-----|-----|-----|-----|-----|-----|-----|-----|-----|-----|-----|-----|-----|
| Thr | Ser | Gly | Thr | Arg | Val | Val | Gln | Val | Leu | Ala | Thr | Asp | Leu | Asp | Glu |     |
|     |     | 260 |     |     |     |     | 265 |     |     |     |     | 270 |     |     |     |     |

| GGC | CCC | AAC | GGT | GAA | ATT | ATT | TAC | TCC | TTC | GGC | AGC | CAC | AAC | CGC | GCC | 981 |
|-----|-----|-----|-----|-----|-----|-----|-----|-----|-----|-----|-----|-----|-----|-----|-----|-----|
| Gly | Pro | Asn | Gly | Glu | Ile | Ile | Tyr | Ser | Phe | Gly | Ser | His | Asn | Arg | Ala |     |
|     | 275 |     |     |     |     | 280 |     |     |     |     | 285 |     |     |     |     |     |

| GGC | GTG | CGG | CAA | CTA | TTC | GCC | TTA | GAC | CTT | GTA | ACC | GGG | ATG | CTG | ACA | 1029 |
|-----|-----|-----|-----|-----|-----|-----|-----|-----|-----|-----|-----|-----|-----|-----|-----|------|
| Gly | Val | Arg | Gln | Leu | Phe | Ala | Leu | Asp | Leu | Val | Thr | Gly | Met | Leu | Thr |      |
| 290 |     |     |     |     | 295 |     |     |     |     | 300 |     |     |     |     | 305 |      |

| ATC | AAG | GGT | CGG | CTG | GAC | TTC | GAG | GAC | ACC | AAA | CTC | CAT | GAG | ATT | TAC | 1077 |
|-----|-----|-----|-----|-----|-----|-----|-----|-----|-----|-----|-----|-----|-----|-----|-----|------|
| Ile | Lys | Gly | Arg | Leu | Asp | Phe | Glu | Asp | Thr | Lys | Leu | His | Glu | Ile | Tyr |      |
|     |     |     |     | 310 |     |     |     |     | 315 |     |     |     |     | 320 |     |      |

| ATC | CAG | GCC | AAA | GAC | AAG | GGC | GCC | AAT | CCC | GAA | GGA | GCA | CAT | TGC | AAA | 1125 |
|-----|-----|-----|-----|-----|-----|-----|-----|-----|-----|-----|-----|-----|-----|-----|-----|------|
| Ile | Gln | Ala | Lys | Asp | Lys | Gly | Ala | Asn | Pro | Glu | Gly | Ala | His | Cys | Lys |      |
|     |     |     | 325 |     |     |     |     | 330 |     |     |     |     | 335 |     |     |      |

| GTG | TTG | GTG | GAG | GTT | GTG | GAT | GTG | AAT | GAC | AAC | GCC | CCG | GAG | ATC | ACA | 1173 |
|-----|-----|-----|-----|-----|-----|-----|-----|-----|-----|-----|-----|-----|-----|-----|-----|------|
| Val | Leu | Val | Glu | Val | Val | Asp | Val | Asn | Asp | Asn | Ala | Pro | Glu | Ile | Thr |      |
|     |     | 340 |     |     |     |     | 345 |     |     |     |     | 350 |     |     |     |      |

| GTC | ACC | TCC | GTG | TAC | AGC | CCA | GTA | CCC | GAG | GAT | GCC | TCT | GGG | ACT | GTC | 1221 |
|-----|-----|-----|-----|-----|-----|-----|-----|-----|-----|-----|-----|-----|-----|-----|-----|------|
| Val | Thr | Ser | Val | Tyr | Ser | Pro | Val | Pro | Glu | Asp | Ala | Ser | Gly | Thr | Val |      |
|     | 355 |     |     |     |     | 360 |     |     |     |     | 365 |     |     |     |     |      |

| ATC | GCT | TTG | CTC | AGT | GTG | ACT | GAC | CTG | GAT | GCT | GGC | GAG | AAC | GGG | CTG | 1269 |
|-----|-----|-----|-----|-----|-----|-----|-----|-----|-----|-----|-----|-----|-----|-----|-----|------|
| Ile | Ala | Leu | Leu | Ser | Val | Thr | Asp | Leu | Asp | Ala | Gly | Glu | Asn | Gly | Leu |      |
| 370 |     |     |     |     | 375 |     |     |     |     | 380 |     |     |     |     | 385 |      |

| GTG | ACC | TGC | GAA | GTT | CCA | CCG | GGT | CTC | CCT | TTC | AGC | CTT | ACT | TCT | TCC | 1317 |
|-----|-----|-----|-----|-----|-----|-----|-----|-----|-----|-----|-----|-----|-----|-----|-----|------|
| Val | Thr | Cys | Glu | Val | Pro | Pro | Gly | Leu | Pro | Phe | Ser | Leu | Thr | Ser | Ser |      |
|     |     |     |     | 390 |     |     |     |     | 395 |     |     |     |     | 400 |     |      |

| CTC | AAG | AAT | TAC | TTC | ACT | TTG | AAA | ACC | AGT | GCA | GAC | CTG | GAT | CGG | GAG | 1365 |
|-----|-----|-----|-----|-----|-----|-----|-----|-----|-----|-----|-----|-----|-----|-----|-----|------|
| Leu | Lys | Asn | Tyr | Phe | Thr | Leu | Lys | Thr | Ser | Ala | Asp | Leu | Asp | Arg | Glu |      |
|     |     |     |     | 405 |     |     |     |     | 410 |     |     |     |     | 415 |     |      |

| ACT | GTG | CCA | GAA | TAC | AAC | CTC | AGC | ATC | ACC | GCC | CGA | GAC | GCC | GGA | ACC | 1413 |
|-----|-----|-----|-----|-----|-----|-----|-----|-----|-----|-----|-----|-----|-----|-----|-----|------|
| Thr | Val | Pro | Glu | Tyr | Asn | Leu | Ser | Ile | Thr | Ala | Arg | Asp | Ala | Gly | Thr |      |
|     |     | 420 |     |     |     |     | 425 |     |     |     |     | 430 |     |     |     |      |

| CCT | TCC | CTC | TCA | GCC | CTT | ACA | ATA | GTG | CGT | GTT | CAA | GTG | TCC | GAC | ATC | 1461 |
|-----|-----|-----|-----|-----|-----|-----|-----|-----|-----|-----|-----|-----|-----|-----|-----|------|
| Pro | Ser | Leu | Ser | Ala | Leu | Thr | Ile | Val | Arg | Val | Gln | Val | Ser | Asp | Ile |      |
|     | 435 |     |     |     |     | 440 |     |     |     |     | 445 |     |     |     |     |      |

| AAT | GAC | AAC | CCT | CCA | CAA | TCT | TCT | CAA | TCT | TCC | TAC | GAC | GTT | TAC | ATT | 1509 |
|-----|-----|-----|-----|-----|-----|-----|-----|-----|-----|-----|-----|-----|-----|-----|-----|------|
| Asn | Asp | Asn | Pro | Pro | Gln | Ser | Ser | Gln | Ser | Ser | Tyr | Asp | Val | Tyr | Ile |      |
| 450 |     |     |     |     | 455 |     |     |     |     | 460 |     |     |     |     | 465 |      |

| GAA | GAA | AAC | AAC | CTC | CCC | GGG | GCT | CCA | ATA | CTA | AAC | CTA | AGT | GTC | TGG | 1557 |
|-----|-----|-----|-----|-----|-----|-----|-----|-----|-----|-----|-----|-----|-----|-----|-----|------|
| Glu | Glu | Asn | Asn | Leu | Pro | Gly | Ala | Pro | Ile | Leu | Asn | Leu | Ser | Val | Trp |      |
|     |     |     |     | 470 |     |     |     |     | 475 |     |     |     |     | 480 |     |      |

| GAC | CCC | GAC | GCC | CCG | CAG | AAT | GCT | CGG | CTT | TCT | TTC | TTT | CTC | TTG | GAG | 1605 |
|-----|-----|-----|-----|-----|-----|-----|-----|-----|-----|-----|-----|-----|-----|-----|-----|------|
| Asp | Pro | Asp | Ala | Pro | Gln | Asn | Ala | Arg | Leu | Ser | Phe | Phe | Leu | Leu | Glu |      |

|       |       |       |       |       |       |       |       |       |       |       |       |       |       |       |       |      |
|---|---|---|---|---|---|---|---|---|---|---|---|---|---|---|---|---|
|       |       |       |       | 485   |       |       |       |       | 490   |       |       |       |       | 495   |       |      |
| CAA   | GGA   | GCT   | GAA   | ACC   | GGG   | CTA   | GTG   | GGT   | CGC   | TAT   | TTC   | ACA   | ATA   | AAT   | CGT   | 1653 |
| Gln   | Gly   | Ala   | Glu   | Thr   | Gly   | Leu   | Val   | Gly   | Arg   | Tyr   | Phe   | Thr   | Ile   | Asn   | Arg   |      |
|       |       | 500   |       |       |       |       | 505   |       |       |       |       | 510   |       |       |       |      |
| GAC   | AAT   | GGC   | ATA   | GTG   | TCA   | TCC   | TTA   | GTG   | CCC   | CTA   | GAC   | TAT   | GAG   | GAT   | CGG   | 1701 |
| Asp   | Asn   | Gly   | Ile   | Val   | Ser   | Ser   | Leu   | Val   | Pro   | Leu   | Asp   | Tyr   | Glu   | Asp   | Arg   |      |
|       |       | 515   |       |       |       |       | 520   |       |       |       |       | 525   |       |       |       |      |
| CGG   | GAA   | TTT   | GAA   | TTA   | ACA   | GCT   | CAT   | ATC   | AGC   | GAT   | GGG   | GGC   | ACC   | CCG   | GTC   | 1749 |
| Arg   | Glu   | Phe   | Glu   | Leu   | Thr   | Ala   | His   | Ile   | Ser   | Asp   | Gly   | Gly   | Thr   | Pro   | Val   |      |
| 530   |       |       |       |       | 535   |       |       |       |       | 540   |       |       |       |       | 545   |      |
| CTA   | GCC   | ACC   | AAC   | ATC   | AGC   | GTG   | AAC   | ATA   | TTT   | GTC   | ACT   | GAT   | CGC   | AAT   | GAC   | 1797 |
| Leu   | Ala   | Thr   | Asn   | Ile   | Ser   | Val   | Asn   | Ile   | Phe   | Val   | Thr   | Asp   | Arg   | Asn   | Asp   |      |
|       |       |       |       | 550   |       |       |       |       | 555   |       |       |       |       | 560   |       |      |
| AAT   | GCC   | CCC   | CAG   | GTC   | CTA   | TAT   | CCT   | CGG   | CCA   | GGT   | GGG   | AGC   | TCG   | GTG   | GAG   | 1845 |
| Asn   | Ala   | Pro   | Gln   | Val   | Leu   | Tyr   | Pro   | Arg   | Pro   | Gly   | Gly   | Ser   | Ser   | Val   | Glu   |      |
|       |       |       | 565   |       |       |       |       | 570   |       |       |       |       | 575   |       |       |      |
| ATG   | CTG   | CCT   | CGA   | GGT   | ACC   | TCA   | GCT   | GGC   | CAC   | CTA   | GTG   | TCA   | CGG   | GTG   | GTA   | 1893 |
| Met   | Leu   | Pro   | Arg   | Gly   | Thr   | Ser   | Ala   | Gly   | His   | Leu   | Val   | Ser   | Arg   | Val   | Val   |      |
|       |       | 580   |       |       |       |       | 585   |       |       |       |       | 590   |       |       |       |      |
| GGC   | TGG   | GAC   | GCG   | GAT   | GCA   | GGG   | CAC   | AAT   | GCC   | TGG   | CTC   | TCC   | TAC   | AGT   | CTC   | 1941 |
| Gly   | Trp   | Asp   | Ala   | Asp   | Ala   | Gly   | His   | Asn   | Ala   | Trp   | Leu   | Ser   | Tyr   | Ser   | Leu   |      |
|       |       | 595   |       |       |       |       | 600   |       |       |       |       | 605   |       |       |       |      |
| TTT   | GGA   | TCC   | CCT   | AAC   | CAG   | AGC   | CTT   | TTT   | GCC   | ATA   | GGG   | CTG   | CAC   | ACT   | GGT   | 1989 |
| Phe   | Gly   | Ser   | Pro   | Asn   | Gln   | Ser   | Leu   | Phe   | Ala   | Ile   | Gly   | Leu   | His   | Thr   | Gly   |      |
| 610   |       |       |       |       | 615   |       |       |       |       | 620   |       |       |       |       | 625   |      |
| CAA   | ATC   | AGT   | ACT   | GCC   | CGT   | CCA   | GTC   | CAA   | GAC   | ACA   | GAT   | TCA   | CCC   | AGG   | CAG   | 2037 |
| Gln   | Ile   | Ser   | Thr   | Ala   | Arg   | Pro   | Val   | Gln   | Asp   | Thr   | Asp   | Ser   | Pro   | Arg   | Gln   |      |
|       |       |       |       | 630   |       |       |       |       | 635   |       |       |       |       | 640   |       |      |
| ACT   | CTC   | ACT   | GTC   | TTG   | ATC   | AAA   | GAC   | AAT   | GGG   | GAG   | CCT   | TCG   | CTC   | TCC   | ACC   | 2085 |
| Thr   | Leu   | Thr   | Val   | Leu   | Ile   | Lys   | Asp   | Asn   | Gly   | Glu   | Pro   | Ser   | Leu   | Ser   | Thr   |      |
|       |       |       | 645   |       |       |       |       | 650   |       |       |       |       | 655   |       |       |      |
| ACT   | GCT   | ACC   | CTC   | ACT   | GTG   | TCA   | GTA   | ACC   | GAG   | GAC   | TCT   | CCT   | GAA   | GCC   | CGA   | 2133 |
| Thr   | Ala   | Thr   | Leu   | Thr   | Val   | Ser   | Val   | Thr   | Glu   | Asp   | Ser   | Pro   | Glu   | Ala   | Arg   |      |
|       |       | 660   |       |       |       |       | 665   |       |       |       |       | 670   |       |       |       |      |
| GCC   | GAG   | TTC   | CCC   | TCT   | GGC   | TCT   | GCC   | CCC   | CGG   | GAG   | CAG   | AAA   | AAA   | AAT   | CTC   | 2181 |
| Ala   | Glu   | Phe   | Pro   | Ser   | Gly   | Ser   | Ala   | Pro   | Arg   | Glu   | Gln   | Lys   | Lys   | Asn   | Leu   |      |
| 675   |       |       |       |       | 680   |       |       |       |       | 685   |       |       |       |       |       |      |
| ACC   | TTT   | TAT   | CTA   | CTT   | CTT   | TCT   | CTA   | ATC   | CTG   | GTT   | TCT   | GTG   | GGC   | TTC   | GTG   | 2229 |
| Thr   | Phe   | Tyr   | Leu   | Leu   | Leu   | Ser   | Leu   | Ile   | Leu   | Val   | Ser   | Val   | Gly   | Phe   | Val   |      |
| 690   |       |       |       | 695   |       |       |       |       | 700   |       |       |       |       | 705   |       |      |
| GTC   | ACA   | GTG   | TTC   | GGA   | GTA   | ATC   | ATA   | TTC   | AAA   | GTT   | TAC   | AAG   | TGG   | AAG   | CAG   | 2277 |
| Val   | Thr   | Val   | Phe   | Gly   | Val   | Ile   | Ile   | Phe   | Lys   | Val   | Tyr   | Lys   | Trp   | Lys   | Gln   |      |
|       |       |       |       | 710   |       |       |       |       | 715   |       |       |       | 720   |       |       |      |
| TCT   | AGA   | GAC   | CTA   | TAC   | CGA   | GCC   | CCG   | GTG   | AGC   | TCA   | CTG   | TAC   | CGA   | ACA   | CCA   | 2325 |
| Ser   | Arg   | Asp   | Leu   | Tyr   | Arg   | Ala   | Pro   | Val   | Ser   | Ser   | Leu   | Tyr   | Arg   | Thr   | Pro   |      |
|       |       |       |       | 725   |       |       |       |       | 730   |       |       |       |       | 735   |       |      |
| GGG   | CCC   | TCC   | TTG   | CAC   | GCG   | GAC   | GCC   | GTG   | CGG   | GGA   | GGC   | CTG   | ATG   | TCG   | CCG   | 2373 |
| Gly   | Pro   | Ser   | Leu   | His   | Ala   | Asp   | Ala   | Val   | Arg   | Gly   | Gly   | Leu   | Met   | Ser   | Pro   |      |
|       |       |       | 740   |       |       |       |       | 745   |       |       |       |       | 750   |       |       |      |
| CAC   | CTT   | TAC   | CAT   | CAG   | GTG   | TAT   | CTC   | ACC   | ACG   | GAC   | TCC   | CGC   | CGC   | AGC   | GAC   | 2421 |
| His   | Leu   | Tyr   | His   | Gln   | Val   | Tyr   | Leu   | Thr   | Thr   | Asp   | Ser   | Arg   | Arg   | Ser   | Asp   |      |
|       |       | 755   |       |       |       |       | 760   |       |       |       |       | 765   |       |       |       |      |
| CCG   | CTG   | CTG   | AAG   | AAA   | CCT   | GGT   | GCA   | GCC   | AGT   | CCA   | CTG   | GCC   | AGC   | CGC   | CAG   | 2469 |
| Pro   | Leu   | Leu   | Lys   | Lys   | Pro   | Gly   | Ala   | Ala   | Ser   | Pro   | Leu   | Ala   | Ser   | Arg   | Gln   |      |
| 770   |       |       |       |       | 775   |       |       |       |       | 780   |       |       |       |       | 785   |      |
| AAC   | ACG   | CTG   | CGG   | AGC   | TGT   | GAT   | CCG   | GTG   | TTC   | TAT   | AGG   | CAG   | GTG   | TTG   | GGT   | 2517 |
| Asn   | Thr   | Leu   | Arg   | Ser   | Cys   | Asp   | Pro   | Val   | Phe   | Tyr   | Arg   | Gln   | Val   | Leu   | Gly   |      |
|       |       |       |       | 790   |       |       |       |       | 795   |       |       |       |       | 800   |       |      |
| GCA   | GAG   | AGC   | GCC   | CCT   | CCC   | GGA   | CAG   | GTA   | AGG   | TTT   | AGC   | AAG   | TCA   | TGC   | TTG   | 2565 |
| Ala   | Glu   | Ser   | Ala   | Pro   | Pro   | Gly   | Gln   | Val   | Arg   | Phe   | Ser   | Lys   | Ser   | Cys   | Leu   |      |

|   |   |   |   |   | 805 |   |   |   |   | 810 |   |   |   |   | 815 |   |   |   |      |
|---|---|---|---|---|-----|---|---|---|---|-----|---|---|---|---|-----|---|---|---|------|
| ACC | CTG | TTA | GTG | CCT | TTT | TAT | TCC | TAC | ATC | ATA | TTG | AGA | AGG | CTG | GAG |   |   |   | 2613 |
| Thr | Leu | Leu | Val | Pro | Phe | Tyr | Ser | Tyr | Ile | Ile | Leu | Arg | Arg | Leu | Glu |   |   |   |      |
|     |     | 820 |     |     |     |     | 825 |     |     |     |     | 830 |     |     |     |   |   |   |      |

CTG TTT TTT TAGTGATGAA GATGTTTCC TGGTGATGCA TTCACACTTT 2662
Leu Phe Phe
835

CAACTGGCTC TTCCTAGATC AAAGTTAGTG CCTTTGTGAG ATGGTGGCCT GCCAGAGTGT 2722

GGTTTGTGGT CCCATTTCAG GGGGAAGATA CTTGACTCAT CTGTGGACCT AATTCACATC 2782

CTCAGCG 2789

( 2 ) INFORMATION FOR SEQ ID NO:105:

( i ) SEQUENCE CHARACTERISTICS:
( A ) LENGTH: 836 amino acids
( B ) TYPE: amino acid
( D ) TOPOLOGY: linear ( i i ) MOLECULE TYPE: protein ( x i ) SEQUENCE DESCRIPTION: SEQ ID NO:105:

Met Val Pro Glu Ala Trp Arg Ser Gly Leu Val Ser Thr Gly Arg Val
1               5                   10                  15

Val Gly Val Leu Leu Leu Leu Gly Ala Leu Asn Lys Ala Ser Thr Val
            20                  25                  30

Ile His Tyr Glu Ile Pro Glu Glu Arg Glu Lys Gly Phe Ala Val Gly
        35                  40                  45

Asn Val Val Ala Asn Leu Gly Leu Asp Leu Gly Ser Leu Ser Ala Arg
    50                  55                  60

Arg Phe Pro Val Val Ser Gly Ala Ser Arg Arg Phe Phe Glu Val Asn
65                  70                  75                  80

Arg Glu Thr Gly Glu Met Phe Val Asn Asp Arg Leu Asp Arg Glu Glu
                85                  90                  95

Leu Cys Gly Thr Leu Pro Ser Cys Thr Val Thr Leu Glu Leu Val Val
            100                 105                 110

Glu Asn Pro Leu Glu Leu Phe Ser Val Glu Val Val Ile Gln Asp Ile
        115                 120                 125

Asn Asp Asn Asn Pro Ala Phe Pro Thr Gln Glu Met Lys Leu Glu Ile
    130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
            180                 185                 190

Tyr Ala Glu Leu Val Leu Glu Arg Ala Leu Asp Arg Glu Arg Glu Pro
        195                 200                 205

Ser Leu Gln Leu Val Leu Thr Ala Leu Asp Gly Gly Thr Pro Ala Leu
    210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
            260                 265                 270

Glu Gly Pro Asn Gly Glu Ile Ile Tyr Ser Phe Gly Ser His Asn Arg

|     |     |     |     |     |     |     |     |     |     |     |     |     |     |     |
|-----|-----|-----|-----|-----|-----|-----|-----|-----|-----|-----|-----|-----|-----|-----|
|     |     | 275 |     |     |     |     | 280 |     |     |     |     | 285 |     |     |
| Ala | Gly | Val | Arg | Gln | Leu | Phe | Ala | Leu | Asp | Leu | Val | Thr | Gly | Met | Leu |
|     | 290 |     |     |     | 295 |     |     |     | 300 |     |     |     |     |     |
| Thr | Ile | Lys | Gly | Arg | Leu | Asp | Phe | Glu | Asp | Thr | Lys | Leu | His | Glu | Ile |
| 305 |     |     |     | 310 |     |     |     | 315 |     |     |     |     |     | 320 |
| Tyr | Ile | Gln | Ala | Lys | Asp | Lys | Gly | Ala | Asn | Pro | Glu | Gly | Ala | His | Cys |
|     |     |     |     | 325 |     |     |     | 330 |     |     |     |     |     | 335 |
| Lys | Val | Leu | Val | Glu | Val | Val | Asp | Val | Asn | Asp | Asn | Ala | Pro | Glu | Ile |
|     |     |     | 340 |     |     |     | 345 |     |     |     | 350 |     |     |     |
| Thr | Val | Thr | Ser | Val | Tyr | Ser | Pro | Val | Pro | Glu | Asp | Ala | Ser | Gly | Thr |
|     |     | 355 |     |     |     | 360 |     |     |     |     | 365 |     |     |     |
| Val | Ile | Ala | Leu | Leu | Ser | Val | Thr | Asp | Leu | Asp | Ala | Gly | Glu | Asn | Gly |
|     | 370 |     |     |     | 375 |     |     |     | 380 |     |     |     |     |     |
| Leu | Val | Thr | Cys | Glu | Val | Pro | Pro | Gly | Leu | Pro | Phe | Ser | Leu | Thr | Ser |
| 385 |     |     |     | 390 |     |     |     | 395 |     |     |     |     |     | 400 |
| Ser | Leu | Lys | Asn | Tyr | Phe | Thr | Leu | Lys | Thr | Ser | Ala | Asp | Leu | Asp | Arg |
|     |     |     |     | 405 |     |     |     | 410 |     |     |     |     |     | 415 |
| Glu | Thr | Val | Pro | Glu | Tyr | Asn | Leu | Ser | Ile | Thr | Ala | Arg | Asp | Ala | Gly |
|     |     |     | 420 |     |     |     | 425 |     |     |     | 430 |     |     |     |
| Thr | Pro | Ser | Leu | Ser | Ala | Leu | Thr | Ile | Val | Arg | Val | Gln | Val | Ser | Asp |
|     |     | 435 |     |     |     | 440 |     |     |     |     | 445 |     |     |     |
| Ile | Asn | Asp | Asn | Pro | Pro | Gln | Ser | Ser | Gln | Ser | Ser | Tyr | Asp | Val | Tyr |
|     | 450 |     |     |     | 455 |     |     |     | 460 |     |     |     |     |     |
| Ile | Glu | Glu | Asn | Asn | Leu | Pro | Gly | Ala | Pro | Ile | Leu | Asn | Leu | Ser | Val |
| 465 |     |     |     | 470 |     |     |     | 475 |     |     |     |     |     | 480 |
| Trp | Asp | Pro | Asp | Ala | Pro | Gln | Asn | Ala | Arg | Leu | Ser | Phe | Phe | Leu | Leu |
|     |     |     |     | 485 |     |     |     | 490 |     |     |     |     |     | 495 |
| Glu | Gln | Gly | Ala | Glu | Thr | Gly | Leu | Val | Gly | Arg | Tyr | Phe | Thr | Ile | Asn |
|     |     |     | 500 |     |     |     | 505 |     |     |     | 510 |     |     |     |
| Arg | Asp | Asn | Gly | Ile | Val | Ser | Ser | Leu | Val | Pro | Leu | Asp | Tyr | Glu | Asp |
|     |     | 515 |     |     |     | 520 |     |     |     |     | 525 |     |     |     |
| Arg | Arg | Glu | Phe | Glu | Leu | Thr | Ala | His | Ile | Ser | Asp | Gly | Gly | Thr | Pro |
|     | 530 |     |     |     | 535 |     |     |     | 540 |     |     |     |     |     |
| Val | Leu | Ala | Thr | Asn | Ile | Ser | Val | Asn | Ile | Phe | Val | Thr | Asp | Arg | Asn |
| 545 |     |     |     | 550 |     |     |     | 555 |     |     |     |     |     | 560 |
| Asp | Asn | Ala | Pro | Gln | Val | Leu | Tyr | Pro | Arg | Pro | Gly | Gly | Ser | Ser | Val |
|     |     |     |     | 565 |     |     |     | 570 |     |     |     |     |     | 575 |
| Glu | Met | Leu | Pro | Arg | Gly | Thr | Ser | Ala | Gly | His | Leu | Val | Ser | Arg | Val |
|     |     |     | 580 |     |     |     | 585 |     |     |     | 590 |     |     |     |
| Val | Gly | Trp | Asp | Ala | Asp | Ala | Gly | His | Asn | Ala | Trp | Leu | Ser | Tyr | Ser |
|     |     | 595 |     |     |     | 600 |     |     |     |     | 605 |     |     |     |
| Leu | Phe | Gly | Ser | Pro | Asn | Gln | Ser | Leu | Phe | Ala | Ile | Gly | Leu | His | Thr |
|     | 610 |     |     |     | 615 |     |     |     | 620 |     |     |     |     |     |
| Gly | Gln | Ile | Ser | Thr | Ala | Arg | Pro | Val | Gln | Asp | Thr | Asp | Ser | Pro | Arg |
| 625 |     |     |     | 630 |     |     |     | 635 |     |     |     |     |     | 640 |
| Gln | Thr | Leu | Thr | Val | Leu | Ile | Lys | Asp | Asn | Gly | Glu | Pro | Ser | Leu | Ser |
|     |     |     |     | 645 |     |     |     | 650 |     |     |     |     |     | 655 |
| Thr | Thr | Ala | Thr | Leu | Thr | Val | Ser | Val | Thr | Glu | Asp | Ser | Pro | Glu | Ala |
|     |     |     | 660 |     |     |     | 665 |     |     |     | 670 |     |     |     |
| Arg | Ala | Glu | Phe | Pro | Ser | Gly | Ser | Ala | Pro | Arg | Glu | Gln | Lys | Lys | Asn |
|     |     | 675 |     |     |     | 680 |     |     |     |     | 685 |     |     |     |
| Leu | Thr | Phe | Tyr | Leu | Leu | Leu | Ser | Leu | Ile | Leu | Val | Ser | Val | Gly | Phe |
|     | 690 |     |     |     | 695 |     |     |     | 700 |     |     |     |     |     |

| | | | | | | | | | | | | | | | |
|---|---|---|---|---|---|---|---|---|---|---|---|---|---|---|---|
| Val | Val | Thr | Val | Phe | Gly | Val | Ile | Ile | Phe | Lys | Val | Tyr | Lys | Trp | Lys |
| 705 | | | | 710 | | | | 715 | | | | | | | 720 |
| Gln | Ser | Arg | Asp | Leu | Tyr | Arg | Ala | Pro | Val | Ser | Ser | Leu | Tyr | Arg | Thr |
| | | | 725 | | | | | 730 | | | | | 735 | | |
| Pro | Gly | Pro | Ser | Leu | His | Ala | Asp | Ala | Val | Arg | Gly | Gly | Leu | Met | Ser |
| | | | 740 | | | | | 745 | | | | | 750 | | |
| Pro | His | Leu | Tyr | His | Gln | Val | Tyr | Leu | Thr | Thr | Asp | Ser | Arg | Arg | Ser |
| | | 755 | | | | | 760 | | | | | 765 | | | |
| Asp | Pro | Leu | Leu | Lys | Lys | Pro | Gly | Ala | Ala | Ser | Pro | Leu | Ala | Ser | Arg |
| | 770 | | | | 775 | | | | | 780 | | | | | |
| Gln | Asn | Thr | Leu | Arg | Ser | Cys | Asp | Pro | Val | Phe | Tyr | Arg | Gln | Val | Leu |
| 785 | | | | | 790 | | | | 795 | | | | | | 800 |
| Gly | Ala | Glu | Ser | Ala | Pro | Pro | Gly | Gln | Val | Arg | Phe | Ser | Lys | Ser | Cys |
| | | | 805 | | | | | 810 | | | | | 815 | | |
| Leu | Thr | Leu | Leu | Val | Pro | Phe | Tyr | Ser | Tyr | Ile | Ile | Leu | Arg | Arg | Leu |
| | | | 820 | | | | | 825 | | | | | 830 | | |
| Glu | Leu | Phe | Phe | | | | | | | | | | | | |
| | | 835 | | | | | | | | | | | | | |

( 2 ) INFORMATION FOR SEQ ID NO:106:

( i ) SEQUENCE CHARACTERISTICS:
        ( A ) LENGTH: 2751 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..2160

( x i ) SEQUENCE DESCRIPTION: SEQ ID NO:106:

```
CGAAAGCCAT GTCGGACTCG TCGCCCAGCG CCCAAGCGCT AACCCGCTGA AAGTTTCTCA         60

GCGAAATCTC AGGGACGATC TGGACCCCGC TGAGAGGAAC TGCTTTTGAG TGAG ATG         117
                                                              Met
                                                              1
```

| | | | | | | | | | | | | | | | | |
|---|---|---|---|---|---|---|---|---|---|---|---|---|---|---|---|---|
| GTC | CCA | GAG | GCC | TGG | AGG | AGC | GGA | CTG | GTA | AGC | ACC | GGG | AGG | GTA | GTG | 165 |
| Val | Pro | Glu | Ala | Trp | Arg | Ser | Gly | Leu | Val | Ser | Thr | Gly | Arg | Val | Val | |
| | | | | 5 | | | | | 10 | | | | | 15 | | |
| GGA | GTT | TTG | CTT | CTG | CTT | GGT | GCC | TTG | AAC | AAG | GCT | TCC | ACG | GTC | ATT | 213 |
| Gly | Val | Leu | Leu | Leu | Leu | Gly | Ala | Leu | Asn | Lys | Ala | Ser | Thr | Val | Ile | |
| | | | 20 | | | | | 25 | | | | | 30 | | | |
| CAC | TAT | GAG | ATC | CCG | GAG | GAA | AGA | GAG | AAG | GGT | TTC | GCT | GTG | GGC | AAC | 261 |
| His | Tyr | Glu | Ile | Pro | Glu | Glu | Arg | Glu | Lys | Gly | Phe | Ala | Val | Gly | Asn | |
| | | 35 | | | | | 40 | | | | | 45 | | | | |
| GTG | GTC | GCG | AAC | CTT | GGT | TTG | GAT | CTC | GGT | AGC | CTC | TCA | GCC | CGC | AGG | 309 |
| Val | Val | Ala | Asn | Leu | Gly | Leu | Asp | Leu | Gly | Ser | Leu | Ser | Ala | Arg | Arg | |
| 50 | | | | | 55 | | | | | 60 | | | | | 65 | |
| TTC | CCG | GTG | GTG | TCT | GGA | GCT | AGC | CGA | AGA | TTC | TTT | GAG | GTG | AAC | CGG | 357 |
| Phe | Pro | Val | Val | Ser | Gly | Ala | Ser | Arg | Arg | Phe | Phe | Glu | Val | Asn | Arg | |
| | | | | 70 | | | | | 75 | | | | | 80 | | |
| GAG | ACC | GGA | GAG | ATG | TTT | GTG | AAC | GAC | CGT | CTG | GAT | CGA | GAG | GAG | CTG | 405 |
| Glu | Thr | Gly | Glu | Met | Phe | Val | Asn | Asp | Arg | Leu | Asp | Arg | Glu | Glu | Leu | |
| | | | | 85 | | | | | 90 | | | | | 95 | | |
| TGT | GGG | ACA | CTG | CCC | TCT | TGC | ACT | GTA | ACT | CTG | GAG | TTG | GTA | GTG | GAG | 453 |
| Cys | Gly | Thr | Leu | Pro | Ser | Cys | Thr | Val | Thr | Leu | Glu | Leu | Val | Val | Glu | |
| | | | 100 | | | | | 105 | | | | | 110 | | | |
| AAC | CCG | CTG | GAG | CTG | TTC | AGC | GTG | GAA | GTG | GTG | ATC | CAG | GAC | ATC | AAC | 501 |
| Asn | Pro | Leu | Glu | Leu | Phe | Ser | Val | Glu | Val | Val | Ile | Gln | Asp | Ile | Asn | |

```
            115                      120                          125
GAC  AAC  AAT  CCT  GCT  TTC  CCT  ACC  CAG  GAA  ATG  AAA  TTG  GAG  ATT  AGC      549
Asp  Asn  Asn  Pro  Ala  Phe  Pro  Thr  Gln  Glu  Met  Lys  Leu  Glu  Ile  Ser
130                 135                      140                      145

GAG  GCC  GTG  GCT  CCG  GGG  ACG  CGC  TTT  CCG  CTC  GAG  AGC  GCG  CAC  GAT      597
Glu  Ala  Val  Ala  Pro  Gly  Thr  Arg  Phe  Pro  Leu  Glu  Ser  Ala  His  Asp
                    150                      155                      160

CCC  GAT  CTG  GGA  AGC  AAC  TCT  TTA  CAA  ACC  TAT  GAG  CTG  AGC  CGA  AAT      645
Pro  Asp  Leu  Gly  Ser  Asn  Ser  Leu  Gln  Thr  Tyr  Glu  Leu  Ser  Arg  Asn
                    165                      170                      175

GAA  TAC  TTT  GCG  CTT  CGC  GTG  CAG  ACG  CGG  GAG  GAC  AGC  ACC  AAG  TAC      693
Glu  Tyr  Phe  Ala  Leu  Arg  Val  Gln  Thr  Arg  Glu  Asp  Ser  Thr  Lys  Tyr
               180                      185                      190

GCG  GAG  CTG  GTG  TTG  GAG  CGC  GCC  CTG  GAC  CGA  GAA  CGG  GAG  CCT  AGT      741
Ala  Glu  Leu  Val  Leu  Glu  Arg  Ala  Leu  Asp  Arg  Glu  Arg  Glu  Pro  Ser
          195                      200                      205

CTC  CAG  TTA  GTG  CTG  ACG  GCG  TTG  GAC  GGA  GGG  ACC  CCA  GCT  CTC  TCC      789
Leu  Gln  Leu  Val  Leu  Thr  Ala  Leu  Asp  Gly  Gly  Thr  Pro  Ala  Leu  Ser
210                 215                      220                      225

GCC  AGC  CTG  CCT  ATT  CAC  ATC  AAG  GTG  CTG  GAC  GCG  AAT  GAC  AAT  GCG      837
Ala  Ser  Leu  Pro  Ile  His  Ile  Lys  Val  Leu  Asp  Ala  Asn  Asp  Asn  Ala
                    230                      235                      240

CCT  GTC  TTC  AAC  CAG  TCC  TTG  TAC  CGG  GCG  CGC  GTT  CCT  GGA  GGA  TGC      885
Pro  Val  Phe  Asn  Gln  Ser  Leu  Tyr  Arg  Ala  Arg  Val  Pro  Gly  Gly  Cys
               245                      250                      255

ACC  TCC  GGC  ACG  CGC  GTG  GTA  CAA  GTC  CTT  GCA  ACG  GAT  CTG  GAT  GAA      933
Thr  Ser  Gly  Thr  Arg  Val  Val  Gln  Val  Leu  Ala  Thr  Asp  Leu  Asp  Glu
          260                      265                      270

GGC  CCC  AAC  GGT  GAA  ATT  ATT  TAC  TCC  TTC  GGC  AGC  CAC  AAC  CGC  GCC      981
Gly  Pro  Asn  Gly  Glu  Ile  Ile  Tyr  Ser  Phe  Gly  Ser  His  Asn  Arg  Ala
275                 280                      285

GGC  GTG  CGG  CAA  CTA  TTC  GCC  TTA  GAC  CTT  GTA  ACC  GGG  ATG  CTG  ACA     1029
Gly  Val  Arg  Gln  Leu  Phe  Ala  Leu  Asp  Leu  Val  Thr  Gly  Met  Leu  Thr
290                 295                      300                      305

ATC  AAG  GGT  CGG  CTG  GAC  TTC  GAG  GAC  ACC  AAA  CTC  CAT  GAG  ATT  TAC     1077
Ile  Lys  Gly  Arg  Leu  Asp  Phe  Glu  Asp  Thr  Lys  Leu  His  Glu  Ile  Tyr
                    310                      315                      320

ATC  CAG  GCC  AAA  GAC  AAG  GGC  GCC  AAT  CCC  GAA  GGA  GCA  CAT  TGC  AAA     1125
Ile  Gln  Ala  Lys  Asp  Lys  Gly  Ala  Asn  Pro  Glu  Gly  Ala  His  Cys  Lys
               325                      330                      335

GTG  TTG  GTG  GAG  GTT  GTG  GAT  GTG  AAT  GAC  AAC  GCC  CCG  GAG  ATC  ACA     1173
Val  Leu  Val  Glu  Val  Val  Asp  Val  Asn  Asp  Asn  Ala  Pro  Glu  Ile  Thr
          340                      345                      350

GTC  ACC  TCC  GTG  TAC  AGC  CCA  GTA  CCC  GAG  GAT  GCC  TCT  GGG  ACT  GTC     1221
Val  Thr  Ser  Val  Tyr  Ser  Pro  Val  Pro  Glu  Asp  Ala  Ser  Gly  Thr  Val
355                 360                      365

ATC  GCT  TTG  CTC  AGT  GTG  ACT  GAC  CTG  GAT  GCT  GGC  GAG  AAC  GGG  CTG     1269
Ile  Ala  Leu  Leu  Ser  Val  Thr  Asp  Leu  Asp  Ala  Gly  Glu  Asn  Gly  Leu
370                 375                      380                      385

GTG  ACC  TGC  GAA  GTT  CCA  CCG  GGT  CTC  CCT  TTC  AGC  CTT  ACT  TCT  TCC     1317
Val  Thr  Cys  Glu  Val  Pro  Pro  Gly  Leu  Pro  Phe  Ser  Leu  Thr  Ser  Ser
                    390                      395                      400

CTC  AAG  AAT  TAC  TTC  ACT  TTG  AAA  ACC  AGT  GCA  GAC  CTG  GAT  CGG  GAG     1365
Leu  Lys  Asn  Tyr  Phe  Thr  Leu  Lys  Thr  Ser  Ala  Asp  Leu  Asp  Arg  Glu
               405                      410                      415

ACT  GTG  CCA  GAA  TAC  AAC  CTC  AGC  ATC  ACC  GCC  CGA  GAC  GCC  GGA  ACC     1413
Thr  Val  Pro  Glu  Tyr  Asn  Leu  Ser  Ile  Thr  Ala  Arg  Asp  Ala  Gly  Thr
          420                      425                      430

CCT  TCC  CTC  TCA  GCC  CTT  ACA  ATA  GTG  CGT  GTT  CAA  GTG  TCC  GAC  ATC     1461
Pro  Ser  Leu  Ser  Ala  Leu  Thr  Ile  Val  Arg  Val  Gln  Val  Ser  Asp  Ile
```

-continued

|     |     |     |     | 435 |     |     |     |     | 440 |     |     |     |     | 445 |     |      |
|-----|-----|-----|-----|-----|-----|-----|-----|-----|-----|-----|-----|-----|-----|-----|-----|------|
| AAT | GAC | AAC | CCT | CCA | CAA | TCT | TCT | CAA | TCT | TCC | TAC | GAC | GTT | TAC | ATT | 1509 |
| Asn | Asp | Asn | Pro | Pro | Gln | Ser | Ser | Gln | Ser | Ser | Tyr | Asp | Val | Tyr | Ile |      |
| 450 |     |     |     |     | 455 |     |     |     |     | 460 |     |     |     |     | 465 |      |
| GAA | GAA | AAC | AAC | CTC | CCC | GGG | GCT | CCA | ATA | CTA | AAC | CTA | AGT | GTC | TGG | 1557 |
| Glu | Glu | Asn | Asn | Leu | Pro | Gly | Ala | Pro | Ile | Leu | Asn | Leu | Ser | Val | Trp |      |
|     |     |     |     |     | 470 |     |     |     |     | 475 |     |     |     |     | 480 |      |
| GAC | CCC | GAC | GCC | CCG | CAG | AAT | GCT | CGG | CTT | TCT | TTC | TTT | CTC | TTG | GAG | 1605 |
| Asp | Pro | Asp | Ala | Pro | Gln | Asn | Ala | Arg | Leu | Ser | Phe | Phe | Leu | Leu | Glu |      |
|     |     |     |     | 485 |     |     |     |     | 490 |     |     |     |     | 495 |     |      |
| CAA | GGA | GCT | GAA | ACC | GGG | CTA | GTG | GGT | CGC | TAT | TTC | ACA | ATA | AAT | CGT | 1653 |
| Gln | Gly | Ala | Glu | Thr | Gly | Leu | Val | Gly | Arg | Tyr | Phe | Thr | Ile | Asn | Arg |      |
|     |     |     | 500 |     |     |     |     | 505 |     |     |     |     | 510 |     |     |      |
| GAC | AAT | GGC | ATA | GTG | TCA | TCC | TTA | GTG | CCC | CTA | GAC | TAT | GAG | GAT | CGG | 1701 |
| Asp | Asn | Gly | Ile | Val | Ser | Ser | Leu | Val | Pro | Leu | Asp | Tyr | Glu | Asp | Arg |      |
|     | 515 |     |     |     |     | 520 |     |     |     |     | 525 |     |     |     |     |      |
| CGG | GAA | TTT | GAA | TTA | ACA | GCT | CAT | ATC | AGC | GAT | GGG | GGC | ACC | CCG | GTC | 1749 |
| Arg | Glu | Phe | Glu | Leu | Thr | Ala | His | Ile | Ser | Asp | Gly | Gly | Thr | Pro | Val |      |
| 530 |     |     |     |     | 535 |     |     |     |     | 540 |     |     |     |     | 545 |      |
| CTA | GCC | ACC | AAC | ATC | AGC | GTG | AAC | ATA | TTT | GTC | ACT | GAT | CGC | AAT | GAC | 1797 |
| Leu | Ala | Thr | Asn | Ile | Ser | Val | Asn | Ile | Phe | Val | Thr | Asp | Arg | Asn | Asp |      |
|     |     |     |     | 550 |     |     |     |     | 555 |     |     |     |     | 560 |     |      |
| AAT | GCC | CCC | CAG | GTC | CTA | TAT | CCT | CGG | CCA | GGT | GGG | AGC | TCG | GTG | GAG | 1845 |
| Asn | Ala | Pro | Gln | Val | Leu | Tyr | Pro | Arg | Pro | Gly | Gly | Ser | Ser | Val | Glu |      |
|     |     |     | 565 |     |     |     |     | 570 |     |     |     |     | 575 |     |     |      |
| ATG | CTG | CCT | CGA | GGT | ACC | TCA | GCT | GGC | CAC | CTA | GTG | TCA | CGG | GTG | GTA | 1893 |
| Met | Leu | Pro | Arg | Gly | Thr | Ser | Ala | Gly | His | Leu | Val | Ser | Arg | Val | Val |      |
|     |     › | 580 |     |     |     |     | 585 |     |     |     |     | 590 |     |     |     |      |
| GGC | TGG | GAC | GCG | GAT | GCA | GGG | CAC | AAT | GCC | TGG | CTC | TCC | TAC | AGT | CTC | 1941 |
| Gly | Trp | Asp | Ala | Asp | Ala | Gly | His | Asn | Ala | Trp | Leu | Ser | Tyr | Ser | Leu |      |
| 595 |     |     |     |     | 600 |     |     |     |     | 605 |     |     |     |     |     |      |
| TTT | GGA | TCC | CCT | AAC | CAG | AGC | CTT | TTT | GCC | ATA | GGG | CTG | CAC | ACT | GGT | 1989 |
| Phe | Gly | Ser | Pro | Asn | Gln | Ser | Leu | Phe | Ala | Ile | Gly | Leu | His | Thr | Gly |      |
| 610 |     |     |     |     | 615 |     |     |     |     | 620 |     |     |     |     | 625 |      |
| CAA | ATC | AGT | ACT | GCC | CGT | CCA | GTC | CAA | GAC | ACA | GAT | TCA | CCC | AGG | CAG | 2037 |
| Gln | Ile | Ser | Thr | Ala | Arg | Pro | Val | Gln | Asp | Thr | Asp | Ser | Pro | Arg | Gln |      |
|     |     |     |     | 630 |     |     |     |     | 635 |     |     |     |     | 640 |     |      |
| ACT | CTC | ACT | GTC | TTG | ATC | AAA | GAC | AAT | GGG | GAG | CCT | TCG | CTC | TCC | ACC | 2085 |
| Thr | Leu | Thr | Val | Leu | Ile | Lys | Asp | Asn | Gly | Glu | Pro | Ser | Leu | Ser | Thr |      |
|     |     |     | 645 |     |     |     |     | 650 |     |     |     |     | 655 |     |     |      |
| ACT | GCT | ACC | CTC | ACT | GTG | TCA | GTA | ACC | GAG | GAC | TCT | CCT | GAA | GCC | CGA | 2133 |
| Thr | Ala | Thr | Leu | Thr | Val | Ser | Val | Thr | Glu | Asp | Ser | Pro | Glu | Ala | Arg |      |
|     |     | 660 |     |     |     |     | 665 |     |     |     |     | 670 |     |     |     |      |
| GCC | GAG | TTC | CCC | TCT | GGC | TCT | GCC | AGT | TAAACCTTCT | | | | TTAATTATGG | | | 2180 |
| Ala | Glu | Phe | Pro | Ser | Gly | Ser | Ala | Ser |     |     |     |     |     |     |     |      |
|     | 675 |     |     |     |     | 680 |     |     |     |     |     |     |     |     |     |      |

| ATTAGCCATT | AACATTTTTG | AAACGTGGAC | CATTTAACCT | CGGCCTACCC | CCTCCAACTG | 2240 |
| TCCTGGTGAT | GAGTTCATTA | GCTAAGTTAA | ATTAATTGAA | CTTTGATCTA | AACCAAAACA | 2300 |
| AATCAGGAAA | ATAAAGCTGT | AAAGGAACTT | ATCAAGCATT | CCAAACCAA  | CTAGAAATTA | 2360 |
| CTTGAAGTTT | CGAGTGAGCA | TTGCCTGTGC | CAGTATTCTT | CATTATAGGA | TTATAAACTC | 2420 |
| GTTTTTTTCC | CAAAGCGCAT | GTCTACGCCA | GGCAGAGGAG | TAATTATTCA | GCCAATTTCA | 2480 |
| TGGATGTAAC | GATGGATATA | AATAATTGAT | AGCACCTAGA | GGCTTCCAGT | TGGGTGGAA  | 2540 |
| GGCTAAAAGT | AGAGGGGAAC | TCACTCACTT | GAGAAATGAT | ATTTAAGTGA | ATAAATAGTT | 2600 |
| CTCTTCTATG | AAACTATTAC | TATTTAGTTC | TCTGGAAAAC | TTAAGTGTAT | AATGATTAG  | 2660 |
| AACATCAAAT | CCTAAGTAAA | GAAATGACAT | TTTAAATATA | AAAAGCCAAA | CTTTAAATAA | 2720 |

ATCATAGAGA CCTCAGACAT AATATAGGAA A 2751

( 2 ) INFORMATION FOR SEQ ID NO:107:

( i ) SEQUENCE CHARACTERISTICS:
  ( A ) LENGTH: 682 amino acids
  ( B ) TYPE: amino acid
  ( D ) TOPOLOGY: linear ( i i ) MOLECULE TYPE: protein ( x i ) SEQUENCE DESCRIPTION: SEQ ID NO:107:

| Met | Val | Pro | Glu | Ala | Trp | Arg | Ser | Gly | Leu | Val | Ser | Thr | Gly | Arg | Val |
|---|---|---|---|---|---|---|---|---|---|---|---|---|---|---|---|
| 1 | | | | 5 | | | | | 10 | | | | | 15 | |
| Val | Gly | Val | Leu | Leu | Leu | Leu | Gly | Ala | Leu | Asn | Lys | Ala | Ser | Thr | Val |
| | | | 20 | | | | | 25 | | | | | 30 | | |
| Ile | His | Tyr | Glu | Ile | Pro | Glu | Glu | Arg | Glu | Lys | Gly | Phe | Ala | Val | Gly |
| | | 35 | | | | | 40 | | | | | 45 | | | |
| Asn | Val | Val | Ala | Asn | Leu | Gly | Leu | Asp | Leu | Gly | Ser | Leu | Ser | Ala | Arg |
| | 50 | | | | | 55 | | | | | 60 | | | | |
| Arg | Phe | Pro | Val | Val | Ser | Gly | Ala | Ser | Arg | Arg | Phe | Phe | Glu | Val | Asn |
| 65 | | | | | 70 | | | | | 75 | | | | | 80 |
| Arg | Glu | Thr | Gly | Glu | Met | Phe | Val | Asn | Asp | Arg | Leu | Asp | Arg | Glu | Glu |
| | | | | 85 | | | | | 90 | | | | | 95 | |
| Leu | Cys | Gly | Thr | Leu | Pro | Ser | Cys | Thr | Val | Thr | Leu | Glu | Leu | Val | Val |
| | | | 100 | | | | | 105 | | | | | 110 | | |
| Glu | Asn | Pro | Leu | Glu | Leu | Phe | Ser | Val | Glu | Val | Val | Ile | Gln | Asp | Ile |
| | | 115 | | | | | 120 | | | | | 125 | | | |
| Asn | Asp | Asn | Asn | Pro | Ala | Phe | Pro | Thr | Gln | Glu | Met | Lys | Leu | Glu | Ile |
| | 130 | | | | | 135 | | | | | 140 | | | | |
| Ser | Glu | Ala | Val | Ala | Pro | Gly | Thr | Arg | Phe | Pro | Leu | Glu | Ser | Ala | His |
| 145 | | | | | 150 | | | | | 155 | | | | | 160 |
| Asp | Pro | Asp | Leu | Gly | Ser | Asn | Ser | Leu | Gln | Thr | Tyr | Glu | Leu | Ser | Arg |
| | | | | 165 | | | | | 170 | | | | | 175 | |
| Asn | Glu | Tyr | Phe | Ala | Leu | Arg | Val | Gln | Thr | Arg | Glu | Asp | Ser | Thr | Lys |
| | | | 180 | | | | | 185 | | | | | 190 | | |
| Tyr | Ala | Glu | Leu | Val | Leu | Glu | Arg | Ala | Leu | Asp | Arg | Glu | Arg | Glu | Pro |
| | | 195 | | | | | 200 | | | | | 205 | | | |
| Ser | Leu | Gln | Leu | Val | Leu | Thr | Ala | Leu | Asp | Gly | Gly | Thr | Pro | Ala | Leu |
| | 210 | | | | | 215 | | | | | 220 | | | | |
| Ser | Ala | Ser | Leu | Pro | Ile | His | Ile | Lys | Val | Leu | Asp | Ala | Asn | Asp | Asn |
| 225 | | | | | 230 | | | | | 235 | | | | | 240 |
| Ala | Pro | Val | Phe | Asn | Gln | Ser | Leu | Tyr | Arg | Ala | Arg | Val | Pro | Gly | Gly |
| | | | | 245 | | | | | 250 | | | | | 255 | |
| Cys | Thr | Ser | Gly | Thr | Arg | Val | Val | Gln | Val | Leu | Ala | Thr | Asp | Leu | Asp |
| | | | 260 | | | | | 265 | | | | | 270 | | |
| Glu | Gly | Pro | Asn | Gly | Glu | Ile | Ile | Tyr | Ser | Phe | Gly | Ser | His | Asn | Arg |
| | | 275 | | | | | 280 | | | | | 285 | | | |
| Ala | Gly | Val | Arg | Gln | Leu | Phe | Ala | Leu | Asp | Leu | Val | Thr | Gly | Met | Leu |
| | 290 | | | | | 295 | | | | | 300 | | | | |
| Thr | Ile | Lys | Gly | Arg | Leu | Asp | Phe | Glu | Asp | Thr | Lys | Leu | His | Glu | Ile |
| 305 | | | | | 310 | | | | | 315 | | | | | 320 |
| Tyr | Ile | Gln | Ala | Lys | Asp | Lys | Gly | Ala | Asn | Pro | Glu | Gly | Ala | His | Cys |
| | | | | 325 | | | | | 330 | | | | | 335 | |
| Lys | Val | Leu | Val | Glu | Val | Val | Asp | Val | Asn | Asp | Asn | Ala | Pro | Glu | Ile |
| | | | 340 | | | | | 345 | | | | | 350 | | |

| | | | | | | | | | | | | | | |
|---|---|---|---|---|---|---|---|---|---|---|---|---|---|---|
| Thr | Val | Thr 355 | Ser | Val | Tyr | Ser | Pro 360 | Val | Pro | Glu | Asp | Ala 365 | Ser | Gly | Thr |
| Val | Ile 370 | Ala | Leu | Leu | Ser | Val 375 | Thr | Asp | Leu | Asp | Ala 380 | Gly | Glu | Asn | Gly |
| Leu 385 | Val | Thr | Cys | Glu | Val 390 | Pro | Pro | Gly | Leu | Pro 395 | Phe | Ser | Leu | Thr | Ser 400 |
| Ser | Leu | Lys | Asn | Tyr 405 | Phe | Thr | Leu | Lys | Thr 410 | Ser | Ala | Asp | Leu | Asp 415 | Arg |
| Glu | Thr | Val | Pro 420 | Glu | Tyr | Asn | Leu | Ser 425 | Ile | Thr | Ala | Arg | Asp 430 | Ala | Gly |
| Thr | Pro | Ser 435 | Leu | Ser | Ala | Leu | Thr 440 | Ile | Val | Arg | Val | Gln 445 | Val | Ser | Asp |
| Ile | Asn 450 | Asp | Asn | Pro | Pro | Gln 455 | Ser | Ser | Gln | Ser | Ser 460 | Tyr | Asp | Val | Tyr |
| Ile 465 | Glu | Glu | Asn | Asn | Leu 470 | Pro | Gly | Ala | Pro | Ile 475 | Leu | Asn | Leu | Ser | Val 480 |
| Trp | Asp | Pro | Asp | Ala 485 | Pro | Gln | Asn | Ala | Arg 490 | Leu | Ser | Phe | Phe | Leu 495 | Leu |
| Glu | Gln | Gly | Ala 500 | Glu | Thr | Gly | Leu | Val 505 | Gly | Arg | Tyr | Phe | Thr 510 | Ile | Asn |
| Arg | Asp | Asn 515 | Gly | Ile | Val | Ser | Ser 520 | Leu | Val | Pro | Leu | Asp 525 | Tyr | Glu | Asp |
| Arg | Arg 530 | Glu | Phe | Glu | Leu | Thr 535 | Ala | His | Ile | Ser | Asp 540 | Gly | Gly | Thr | Pro |
| Val 545 | Leu | Ala | Thr | Asn | Ile 550 | Ser | Val | Asn | Ile | Phe 555 | Val | Thr | Asp | Arg | Asn 560 |
| Asp | Asn | Ala | Pro | Gln 565 | Val | Leu | Tyr | Pro | Arg 570 | Pro | Gly | Gly | Ser | Ser 575 | Val |
| Glu | Met | Leu | Pro 580 | Arg | Gly | Thr | Ser | Ala 585 | Gly | His | Leu | Val | Ser 590 | Arg | Val |
| Val | Gly | Trp 595 | Asp | Ala | Asp | Ala | Gly 600 | His | Asn | Ala | Trp | Leu 605 | Ser | Tyr | Ser |
| Leu | Phe 610 | Gly | Ser | Pro | Asn | Gln 615 | Ser | Leu | Phe | Ala | Ile 620 | Gly | Leu | His | Thr |
| Gly 625 | Gln | Ile | Ser | Thr | Ala 630 | Arg | Pro | Val | Gln | Asp 635 | Thr | Asp | Ser | Pro | Arg 640 |
| Gln | Thr | Leu | Thr | Val 645 | Leu | Ile | Lys | Asp | Asn 650 | Gly | Glu | Pro | Ser | Leu 655 | Ser |
| Thr | Thr | Ala | Thr 660 | Leu | Thr | Val | Ser | Val 665 | Thr | Glu | Asp | Ser | Pro 670 | Glu | Ala |
| Arg | Ala | Glu 675 | Phe | Pro | Ser | Gly | Ser 680 | Ala | Ser | | | | | | |